US012790335B2

United States Patent

(12) United States Patent
Calvo et al.

(10) Patent No.: US 12,790,335 B2
(45) Date of Patent: Nov. 10, 2026

(54) CD206 MODULATORS THEIR USE AND METHODS FOR PREPARATION

(71) Applicant: The United States of America, As Represented by the Secretary, Dept. of Health and Human Services, Bethesda, MD (US)

(72) Inventors: Raul Rolando Calvo, Rockville, MD (US); Bolormaa Baljinnyam, Rockville, MD (US); Andres Eduardo Dulcey, Rockville, MD (US); Udo Rudloff, Bethesda, MD (US); Mark James Henderson, Bethesda, MD (US); Juan Jose Marugan, Bethesda, MD (US); Xin Hu, Bethesda, MD (US); Noel Terrence Southall, Bethesda, MD (US); Rushikesh Vilas Sable, Bethesda, MD (US)

(73) Assignee: The United States of America as Represented by the Secretary, Department of Health and Human Services, Bethesda, MD (US)

( * ) Notice: Subject to any disclaimer, the term of this patent is extended or adjusted under 35 U.S.C. 154(b) by 813 days.

(21) Appl. No.: 17/787,313

(22) PCT Filed: Dec. 16, 2020

(86) PCT No.: PCT/US2020/065238

§ 371 (c)(1),
(2) Date: Jun. 18, 2022

(87) PCT Pub. No.: WO2021/126923

PCT Pub. Date: Jun. 24, 2021

(65) Prior Publication Data

US 2023/0056497 A1 Feb. 23, 2023

Related U.S. Application Data

(60) Provisional application No. 62/950,488, filed on Dec. 19, 2019.

(51) Int. Cl.
*C07D 487/04* (2006.01)
*A61P 35/00* (2006.01)
(Continued)

(52) U.S. Cl.
CPC ............ *C07D 487/04* (2013.01); *A61P 35/00* (2018.01); *C07D 307/80* (2013.01); *C07D 471/04* (2013.01)

(58) Field of Classification Search
CPC ..... A61P 35/00; C07D 487/04; C07D 307/80; C07D 471/04
See application file for complete search history.

(56) References Cited

U.S. PATENT DOCUMENTS

| | | | |
|---|---|---|---|
| 2005/0009876 | A1 | 1/2005 | Bhagwat |
| 2014/0371199 | A1 | 12/2014 | Nacro |

FOREIGN PATENT DOCUMENTS

| | | | |
|---|---|---|---|
| EP | 2818471 A1 | 12/2014 | |
| WO | 0210137 A2 | 2/2002 | |

(Continued)

OTHER PUBLICATIONS

Hanahan, Douglas, and Robert A. Weinberg. "The Hallmarks of Cancer." Cell 100, No. 1 (2000): 57-70 (Year: 2000).*

(Continued)

*Primary Examiner* — James H Alstrum-Acevedo
*Assistant Examiner* — Carolyn L. Ladd
(74) *Attorney, Agent, or Firm* — McDonnell Boehnen Hulbert & Berghoff LLP

(57) ABSTRACT

Compounds of Formula I, Formula II, and Formula III and the pharmaceutically acceptable salts thereof are disclosed. The variables X, a, b, c, d, $R^{1-4}$, $R^{10-15}$ and $R^{17-22}$ are disclosed herein. The compounds are useful for treating cancer disorders, especially those involving M2 phenotype of macrophages. Pharmaceutical compositions containing compounds of Formula I or Formula II or Formula III and methods of treatment comprising administering compounds of Formula I and Formula II and Formula III are also disclosed.

(I)

(II)

(III)

(Continued)

17 Claims, 22 Drawing Sheets

(51) Int. Cl.
*C07D 307/80* (2006.01)
*C07D 471/04* (2006.01)

(56) References Cited

FOREIGN PATENT DOCUMENTS

| | | | |
|---|---|---|---|
| WO | 2006/018727 | A2 | 2/2006 |
| WO | 2006018735 | A2 | 2/2006 |
| WO | 2006058007 | A2 | 6/2006 |
| WO | 2009/086303 | A2 | 7/2009 |
| WO | 2011/014462 | A1 | 2/2011 |
| WO | 2013024002 | A1 | 2/2013 |
| WO | 2016089977 | A1 | 6/2016 |
| WO | 2017/040993 | A1 | 3/2017 |

OTHER PUBLICATIONS

Tanaka et al "CD206 expression in induced microglia-like cells from peripheral blood as a surrogate biomarker for the specific immune microenvironment of neurosurgical diseases including glioma." Frontiers in Immunology 12 (2021): 670131 (Year: 2021).*

Zhao, Zhixun, Yanwei Yang, Zheng Liu, Haipeng Chen, Xu Guan, Zheng Jiang, Ming Yang et al. "Prognostic and immunotherapeutic significance of mannose receptor C type II in 33 cancers: An integrated analysis." Frontiers in Molecular Biosciences 9 (2022): 951636 (Year: 2022).*

Balan, Dharvind, Nirmala Chandralega Kampan, Magdalena Plebanski, and Nor Haslinda Abd Aziz. "Unlocking ovarian cancer heterogeneity: advancing immunotherapy through single-cell transcriptomics." Frontiers in Oncology 14 (2024): 1388663) (Year: 2024).*

Fang et al. "Prognostic significance of CD163+ and/or CD206+ tumor-associated macrophages is linked to their spatial distribution and tumor-infiltrating lymphocytes in breast cancer." Cancers 16, No. 11 (2024): 2147 (Year: 2024).*

John Hopkins Medicine, "Brain Tumor Types," https://www.hopkinsmedicine.org/health/conditions-and-diseases/brain-tumor/brain-tumor-types#:~:text=There%20are%20more%20than%20120,cells%20they%20are%20made%20of, Accessed: Jul. 30, 2025 (Year: 2025).*

The Leukaemia Foundation, "Types of blood cancer," https://www.leukaemia.org.au/blood-cancer/types-of-blood-cancer/#:~:text=With%20over%20120%20different%20types%20of%20blood,and%20blood%20disorders%2C%20including%20diagnosis%20and%20treatment, Accessed: Jul. 31, 2025 (Year: 2025).*

Xu, Chenchen, Jiyu Chen, Mi Tan, and Qingqing Tan. "The role of macrophage polarization in ovarian cancer: From molecular mechanism to therapeutic potentials." Frontiers in Immunology 16 (2025): 1543096 (Year: 2025).*

Jerome et al., "Continued exploration of the triazolopyridine scaffold as a platform for p38 MAP kinase inhibition", Biorganic & Medicinal Chemistry Letters, 2010, 20(2), 469-473.

Glaffig et al., "A Synthetic MUCI Anticancer Vaccine Containing Mannose Ligands for Targeting Macrophages and Dendritic Cells", Chemmedchem, 2018, 13(1), 25-29.

Matthews, et al., "Design and evaluation of 3,6-di(hetero)aryl imidazo[1,2-a]pyrazines as inhibitors of checkpoint and other kinases", Bioorganic & Medicinal Chemistry Letters, 20(14), pp. 4045-4049, Jul. 15, 2010.

J.M. Jaynes et al., "Mannose receptor (CD206) activation in tumor-associated macrophages enhances adaptive and innate antitumor immune responses," HHS Public Access Author Manuscript No. 1633113, published as Sci Transl Med, 12(530), Feb. 12, 2020.

J.W. Lee et al., "Genetically Engineered Mouse Models of Pancreatic Cancer: The KPC Model (LSL-KrasG12D/+;LSL-Trp53R172H/+;Pdx-1-Cre), Its Variants and Their Application in Immuno-oncology Drug Discovery," Author Manuscript, published as Curr Protoc Pharmacol., 73:14.39.1-14.39.20 (2017).

W.W. Overwijk et al., "B16 as a Mouse Model for Human Melanoma," Author Manuscript, published as Curr Protoc Immunol., Unit-20.1 (2001).

* cited by examiner

DOTTED ARROW INDICATES CLOSED CONFIRMATION OF CD206 AND SOLID ARROW INDICATES OPEN CONFIRMATION OF CD206

COMPOUND 28

CD206 MODULATORS THEIR USE AND METHODS FOR PREPARATION

CROSS-REFERENCE TO RELATED APPLICATIONS

This application is the US national phase under 35 U.S.C. § 371 of International Application No. PCT/US2020/065238 filed 16 Dec. 2020, which claims priority to U.S. Provisional Application Ser. No. 62/950,488 filed 19 Dec. 2019, the contents of which are incorporated herein by reference in their entirety.

STATEMENT OF GOVERNMENT SUPPORT

This invention was made in part with government support from the National Institutes of Health under Grant No. ZIA-BC011267. The government has certain rights in this invention.

BACKGROUND OF THE INVENTION

1. Field of the Invention

The present invention is directed to immunotherapy drugs, and more particularly to compounds that modulate CD206 as well as their use and methods for preparation.

2. Brief Description of the Related Art

Pancreatic cancer is a disease in which malignant (cancerous) cells form in the tissues of the pancreas. Pancreatic cancer often has a poor prognosis, even when diagnosed early. Pancreatic cancer typically spreads rapidly and is seldom detected in its early stages, which is a major reason why it's a leading cause of cancer death. Pancreatic cancer is the fourth leading cause of cancer death in both men and women in the United States of America (U.S.), with more than 44,000 deaths annually. Pancreatic cancer is expected to rank second in all cancer-related deaths in the United States by 2030. Furthermore, the 5-year survival rate of pancreatic cancer in the U.S. ranks lowest among solid organ tumors. There is no reliable screening test for the early detection of pancreatic cancer. Signs and symptoms may not appear until pancreatic cancer is quite advanced, and complete surgical removal isn't possible.

Standard treatment of pancreatic cancer, including surgery, radiation therapy, and chemotherapy largely show limited efficacy. Indeed, approved treatments including gemcitabine, folfirinox, the combination of gemcitabine and abraxane, and the combination of gemcitabine and erlotinib, improve survival by a few to several months, at best. Newer therapies have not demonstrated much more success, possibly due to the thick stroma, a unique immune infiltrate characterized by a paucity of cytotoxic tumor-infiltrating T cells, a high number of immune suppressive pro-tumor myeloid cells, and the relative absence of abundant vessels in the pancreas. Pancreatic ductal adenocarcinoma (PDA) accounts for >90% of pancreatic cancer cases, with a five-year survival rate of 6%.

Recent advances in immunotherapy have transformed the care of many cancer patients. However, these positive findings are limited to immunologically 'hot' cancers whereas in the greater majority of solid organ cancers, like pancreatic cancer, which are classified as immunologically 'cold', the promise of immunotherapy via T cell activation has so far largely evaded patients. These tumors create an immune milieu which excludes cytotoxic T cells or induces an exhausted T cell phenotype through an abundance of immune evasive cues frequently involving innate immune cells. Strategies that reinvigorate innate immune cells are underrepresented within current immuno-oncology therapies.

Tumor cells attract and reprogram innate immune cells including tumor-associated macrophages (TAMs) to support tumor growth and metastatic spread. While the dichotomous M1 versus M2 classification omits to capture the ontogeny and tissue-specific cues of TAMs, in general terms, M1-like TAMs are proposed the more common phenotype in early tumor stages, while M2 TAMs are more prominent in more evolved cancers. $CD206^{high}$ M2 TAMs harness tumor growth via the excretion of cancer-promoting factors or via promotion of angiogenesis, nurturing of cancer stem cells, or the generation of an immune-evasive microenvironment.

CD206 is a member of the large C-type lectin receptor family which can target and modulate the M2 macrophages. CD206 via its eight carbohydrate recognition domains is involved in recognition and binding of mannan and fucose carbohydrate residues from microbial organisms, or via its fibronectin domain II as a scavenger receptor in the phagocytosis of collagen fragments generated during tissue injury and wound healing. Ligand binding or low pH induces 'rolling-in' (via multiple Ca+-dependent intramolecular interactions between the carbohydrate recognition domains) and the closed ('active') form of the receptor which triggers in M2 macrophages, among other signaling cascades, via GRB2-mediated activation of small Rho-GTPases NF-kB signaling activation and induction of phagocytosis and autophagy.

TAMs express scavenger receptors such as CD206 which facilitate tumor angiogenesis, tumor cell migration, maintenance of an EMT-like phenotype of cancer cells, and metastasis. $CD206^{high}$ expression has been associated with poor clinical outcomes in pancreatic cancer and other solid organ cancers. Selective depletion of M2 tumor associated macrophages may improve anti-tumor immunity and cancer outcome.

Using a synthetic host defense peptide design known to regulate innate immune function via binding to C-type lectin receptors (RP-182) it was previously shown that binding to amino acid carbohydrate recognition domain 5 (CRD5) sequence NFGDLVSIQSESEKK of the CD206 receptor: (1) activates a program of phagocytosis and autophagy in M2 macrophages leading to metabolic reprogramming and a M1-like phenotype of these cells as well as, (2) intracellular signaling activation of NF-kB leading to selective killing via autocrine TNFalpha-mediated caspase 8 and 3 activation of $CD206^{high}$ M2 macrophages (U.S. Pat. No. 10,016,480). However, the unfavorable pharmacokinetic (PK) properties of the peptide-based innate immune regulator hinder clinical prospects of synthetic peptides like RP-182. Therefore, small molecule modulators of CD206 are highly desired.

SUMMARY OF THE INVENTION

Described herein are small molecule modulators targeting the CD206 receptor, their methods of manufacture, compositions containing the described compounds, and methods of using the described compounds.

In a first aspect, a compound of Formula I and the pharmaceutically acceptable salts of a compound of Formula I is provided.

Formula I

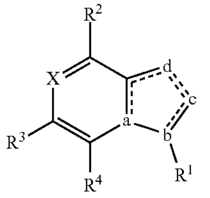

Within Formula I the following conditions are met.

Each bond shown as a solid line and a dashed line together, ⎓, can be a single bond, double, or aromatic bond.

$R^1$ is hydrogen, halogen, hydroxyl, cyano, —$CO_2H$, $C_1$-$C_6$alkyl, $C_2$-$C_6$alkenyl, $C_2$-$C_6$alkynyl, $C_1$-$C_6$alkoxy, —($C_0$-$C_6$alkyl)cycloalkyl, $C_1$-$C_6$haloalkyl, —($C_0$-$C_6$alkyl)phenyl, —($C_0$-$C_6$alkyl)aryl, —($C_0$-$C_6$alkyl)heteroaryl, —C(O)$C_1$-$C_6$alkyl, —C(O)$NR^8R^9$, —($C_0$-$C_6$alkyl)$NR^5R^6$, —$CO_2R^6$, —$C_6H_4$—$R^7$, and a monocyclic or bicyclic heterocycle of 4 to 10 ring atoms having 1, 2, or 3 ring atoms independently chosen from N, S and O.

$R^2$, $R^3$, and $R^4$ are each independently chosen at each occurrence from hydrogen, halogen, hydroxyl, cyano, —$CO_2H$, $C_1$-$C_6$alkyl, $C_2$-$C_6$alkenyl, $C_2$-$C_6$alkynyl, $C_1$-$C_6$alkoxy, —($C_0$-$C_6$alkyl)cycloalkyl, $C_1$-$C_6$haloalkyl, —($C_0$-$C_6$alkyl)phenyl, —($C_0$-$C_6$alkyl)aryl, —($C_0$-$C_6$alkyl)heteroaryl, —C(O)$C_1$-$C_6$alkyl, —C(O)$NR^5R^6$, ($C_0$-$C_6$alkyl)$NR^8R^9$, —$CO_2R^6$, and —$C_6H_4$—$R^7$.

a, b, c, d, and X are each independently chosen at each occurrence from N, C, and CH.

$R^5$, and $R^6$ are each independently chosen at each occurrence from hydrogen, halogen, hydroxy, $C_1$-$C_6$alkyl, $C_1$-$C_6$haloalkyl, $C_1$-$C_6$hydroxyalkyl, $C_1$-$C_6$alkoxy, a substituted or unsubstituted —($C_0$-$C_6$alkyl)cycloalkyl, —($C_0$-$C_6$alkyl)phenyl, —($C_0$-$C_6$alkyl)aryl, —($C_0$-$C_6$alkyl)heteroaryl, —C(O)$C_1$-$C_6$alkyl, —C(O)($C_0$-$C_6$alkyl)phenyl, —($C_0$-$C_6$alkyl)$NR^8R^9$, —C(O)($C_0$-$C_6$alkyl)aryl, —C(O)($C_0$-$C_6$alkyl)heteroaryl, and a 4- to 7-membered heterocycloalkyl ring having 1, 2, or 3 ring atoms independently chosen from N, O, and S.

Any $R^5$ and $R^6$ bound to the same nitrogen atom may be taken together to form a 4- to 7-membered monocyclic heterocycloalkyl ring or 6- to 11-membered bridged bicyclic heterocycloalkyl ring, which heterocycloalkyl ring contains 0, 1, or 2 additional heteroatoms chosen from N, O, S, S(O), and $SO_2$ which heterocycloalkyl ring is optionally substituted at any carbon or hetero ring atom with halogen, hydroxyl, cyano, oxo, dioxo, $C_1$-$C_6$alkyl, $C_1$-$C_6$alkoxy, $C_1$-$C_6$haloalkyl, —($C_0$-$C_6$alkyl)cycloalkyl, —($C_0$-$C_6$alkyl)phenyl, —($C_0$-$C_6$alkyl)aryl, —($C_0$-$C_6$alkyl)$CO_2R^8$, —($C_0$-$C_6$alkyl)C(O)$NR^8R^9$, —($C_1$-$C_6$alkyl)$OR^8$, —C(O)$C_1$-$C_6$alkyl, —($C_0$-$C_6$alkyl)$NR^8R^9$, or —C(O)($C_0$-$C_6$alkyl)$NR^8R^9$.

$R^7$ is hydrogen, halogen, hydroxyl, cyano, —$CO_2H$, $C_1$-$C_6$alkyl, $C_2$-$C_6$alkenyl, $C_2$-$C_6$alkynyl, $C_1$-$C_6$alkoxy, $C_1$-$C_6$haloalkyl, —($C_0$-$C_6$alkyl)cycloalkyl, —($C_0$-$C_6$alkyl)phenyl, —($C_0$-$C_6$alkyl)aryl, —($C_0$-$C_6$alkyl)heteroaryl, —$CO_2R^8$, —C(O)$C_1$-$C_6$alkyl, —C(O)$C_2$-$C_6$alkenyl, —C(O)$C_2$-$C_6$alkynyl, —C(O)$C_1$-$C_6$alkoxy, —C(O)$C_1$-$C_6$hydroxyalkyl, —C(O)—($C_0$-$C_6$alkyl)cycloalkyl, —C(O)—($C_0$-$C_6$alkyl)phenyl, —C(O)—($C_0$-$C_6$alkyl)aryl, —C(O)—($C_0$-$C_6$alkyl)heteroaryl, —C(O)$NR^8R^9$, —C(O)$NR^5R^6$, —C(O)—($C_0$-$C_6$alkyl)$NR^5R^6$, —C(O)—$NR^B$—($C_0$-$C_6$alkyl)$NR^5R^6$, or ($C_0$-$C_6$alkyl)$NR^5R^6$.

$R^8$ and $R^9$ are each independently chosen at each occurrence from hydrogen, halogen, $C_1$-$C_6$ alkyl, $C_1$-$C_6$alkoxy, $C_1$-$C_6$haloalkyl, —($C_0$-$C_6$alkyl)phenyl, —($C_0$-$C_6$alkyl)aryl, —($C_0$-$C_6$alkyl)$NR^5R^6$, —$CO_2R^6$, —C(O)$C_1$-$C_6$alkyl, and —($C_0$-$C_6$alkyl)cycloalkyl.

In a second aspect, a compound of Formula II and the pharmaceutically acceptable salts of a compound of Formula II is provided.

Formula II

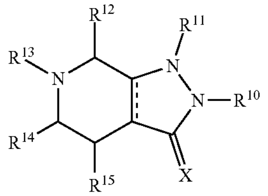

Within Formula II the following conditions are met.

Each bond shown as a solid line and a dashed line together, ⎓, can be a single or double bond.

$R^{10}$, $R^{11}$, and $R^{13}$ are each independently chosen at each occurrence from hydrogen, hydroxyl, —$CO_2H$, $C_1$-$C_6$alkyl, $C_2$-$C_6$alkenyl, $C_2$-$C_6$alkynyl, $C_1$-$C_6$alkoxy, —($C_0$-$C_6$alkyl)cycloalkyl, $C_1$-$C_6$haloalkyl, —($C_0$-$C_6$alkyl)phenyl, —($C_0$-$C_6$alkyl)aryl, —($C_0$-$C_6$alkyl)heteroaryl, —C(O)$C_1$-$C_6$alkyl, —C(O)heteroaryl, and —$CO_2R^{16}$.

$R^{12}$, $R^{14}$, and $R^{15}$ are each independently chosen at each occurrence from hydrogen, halogen, hydroxyl, and cyano.

X is O or S.

$R^{16}$ is hydrogen, halogen, hydroxy, an amino group, $C_1$-$C_6$alkyl, $C_2$-$C_6$alkenyl, $C_2$-$C_6$alkynyl, $C_1$-$C_6$alkoxy, —($C_0$-$C_6$alkyl)cycloalkyl, —C(O)$C_1$-$C_6$alkyl, —($C_0$-$C_6$alkyl)aryl, —($C_0$-$C_6$alkyl)heteroaryl, —($C_0$-$C_6$alkyl)phenyl, or a monocyclic or bicyclic heterocycle of 4 to 10 ring atoms having 1, 2, or 3 ring atoms independently chosen from N, S and O.

In a third aspect, a compound of Formula III and the pharmaceutically acceptable salts of a compound of Formula III is provided.

Formula III

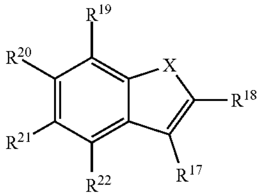

Within Formula III the following conditions are met.

$R^{17}$, $R^{18}$, and $R^{21}$ are each independently chosen at each occurrence from hydrogen, halogen, hydroxyl, cyano, an amidino group, —$NR^{23}R^{24}$, a sulfonic acid group or a salt thereof, a phosphoric acid group or a salt thereof, —$CO_2H$, $C_1$-$C_6$alkyl, $C_2$-$C_6$alkenyl, $C_2$-$C_6$alkynyl, $C_1$-$C_6$alkoxy, —($C_0$-$C_6$alkyl)cycloalkyl, $C_1$-$C_6$haloalkyl, —($C_0$-$C_6$alkyl)phenyl, —($C_0$-$C_6$alkyl)aryl, —($C_0$-$C_6$alkyl)heteroaryl, —C(O)$C_1$-$C_6$alkyl, —C(O)($C_0$-$C_6$alkyl)phenyl, —C(O)($C_0$-$C_6$alkyl)aryl, —C(O)($C_0$-$C_6$alkyl)heteroaryl, —C(O)$NR^{23}R^{24}$, —($C_0$-$C_6$alkyl)$NR^{23}R^{24}$, —$CO_2R^{23}$, and a monocyclic or bicyclic heterocycle of 4 to 10 ring atoms having 1, 2, or 3 ring atoms independently chosen from N, S and O.

X is chosen at each occurrence from 0 and S.

$R^{19}$, $R^{20}$, and $R^{22}$ are each independently chosen at each occurrence from hydrogen, halogen, hydroxy, cyano, and an amino group.

$R^{23}$ and $R^{24}$ are each independently chosen at each occurrence from hydrogen, halogen, $C_1$-$C_6$ alkyl, $C_1$-$C_6$alkoxy, $C_1$-$C_6$haloalkyl, $C_1$-$C_6$haloalkoxy, $C_1$-$C_6$alkoxy, —($C_0$-$C_6$alkyl)phenyl, —($C_0$-$C_6$alkyl)aryl, —($C_0$-$C_6$alkyl)heteroaryl, —C(O)($C_0$-$C_6$alkyl)phenyl, —C(O)($C_0$-$C_6$alkyl) aryl, —C(O)($C_0$-$C_6$alkyl)heteroaryl, —S(O)phenyl, —S(O) aryl, —S(O)heteroaryl, —$SO_2$phenyl, —$SO_2$aryl, —$SO_2$heteroaryl, —($C_0$-$C_6$alkyl)cycloalkyl, and —$CO_2R^{25}$.

$R^{25}$ is hydrogen, halogen, hydroxy, an amino group, $C_1$-$C_6$alkyl, $C_2$-$C_6$alkenyl, $C_2$-$C_6$alkynyl, $C_1$-$C_6$alkoxy, —($C_0$-$C_6$alkyl)cycloalkyl, —C(O)$C_1$-$C_6$alkyl, —($C_0$-$C_6$alkyl)aryl, —($C_0$-$C_6$alkyl)heteroaryl, —($C_0$-$C_6$alkyl)phenyl, or a monocyclic or bicyclic heterocycle of 4 to 10 ring atoms having 1, 2, or 3 ring atoms independently chosen from N, S and O.

Pharmaceutical compositions comprising a compound or salt of Formula I or Formula II or Formula III with a pharmaceutically acceptable carrier are also disclosed.

Methods for the treatment of cancer which may involve selective targeting of M2 macrophages and the reprogramming of M2 macrophages towards a M1 phenotype in a patient, comprising the step of administering to the patient in need thereof a compound of Formula I or Formula II or Formula III or a salt thereof, are also disclosed.

In some embodiments targeting CD206 M2 macrophages with compound or salt of Formula I or Formula II or Formula III may have a dual effect: it may reprogram CD206 M2 macrophages into a M1 macrophage and it may directly kill a M2 macrophage.

Methods for the treatment of cancer characterized by the presence of CD206 positive tumor-associated macrophages (TAM), such as glioma (glioblastoma), sarcoma, astrocytoma, melanoma, non-small cell lung cancer, cholangiocarcinomas, colon cancer, hepatocellular, breast, prostate, gastric, renal cell, endometrial, or pancreatic cancer comprising administering a therapeutically effective amount of a compound or salt of Formula I or Formula II or Formula III to a patient in need of such treatment are also disclosed.

BRIEF DESCRIPTION OF THE DRAWINGS

The following Detailed Description, given by way of Examples, but not intended to limit the invention to specific embodiments described, may be understood in conjunction with the accompanying figures, in which:

FIG. 18B shows reduction of CD206 positive cells within tumor associated macrophage population measured by CD11b+F4/80+Gr-1 negative cells, FIG. 18C shows reduction of the innate checkpoint Signal regulatory protein α (SIRPα), a regulatory membrane glycoprotein from SIRP family, inhibiting cancer cell phagocytosis of tumor associated macrophages determined by CD11b+F4/80+Gr-1 negative cells;

DETAILED DESCRIPTION OF THE INVENTION

Terminology

Figure 1A:
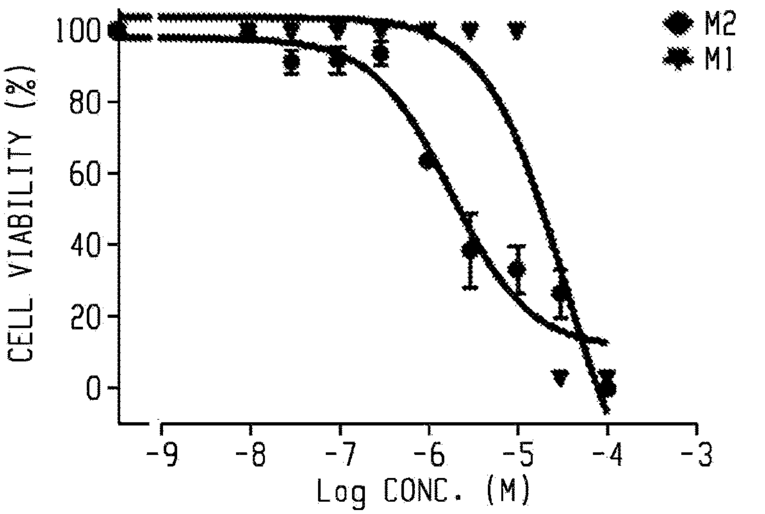
FIG. 1A shows a graph of Percentage Relative Cell Viability versus Log Molar Concentration illustrating the anti-cell viability screening for Compound 1.

Compounds are described using standard nomenclature. Unless defined otherwise, all technical and scientific terms used herein have the same meaning as is commonly understood by one of skill in the art to which this invention belongs.

The terms "a" and "an" do not denote a limitation of quantity, but rather denote the presence of at least one of the referenced items. The term "or" means "and/or." The terms "comprising," "having," "including," and "containing" are to be construed as open-ended terms (i.e., meaning "including, but not limited to").

Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable.

All methods described herein can be performed in any suitable order unless otherwise indicated herein or otherwise clearly contradicted by context. The use of any and all examples, or exemplary language (e.g., "such as"), is intended for illustration and does not pose a limitation on the scope of the disclosure unless otherwise claimed. No language in the specification should be construed as indicating any non-claimed element as essential to the practice of the invention. Unless defined otherwise, technical and scientific terms used herein have the same meaning as is commonly understood by one of skill in the art of this disclosure.

Furthermore, the disclosure encompasses all variations, combinations, and permutations in which one or more limitations, elements, clauses, and descriptive terms from one or more of the listed claims are introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group.

All compounds are understood to include all possible isotopes of atoms occurring in the compounds. Isotopes include those atoms having the same atomic number but different mass numbers. By way of general example, and without limitation, isotopes of hydrogen include tritium and deuterium and isotopes of carbon include $^{11}C$, $^{13}C$, and $^{14}C$.

Formula I includes all pharmaceutically acceptable salts of Formula I.

Formula II includes all pharmaceutically acceptable salts of Formula II.

Formula III includes all pharmaceutically acceptable salts of Formula III.

The opened ended term "comprising" includes the intermediate and closed terms "consisting essentially of" and "consisting of."

The term "substituted" means that any one or more hydrogens on the designated atom or group is replaced with a selection from the indicated group, provided that the designated atom's normal valence is not exceeded. When the substituent is oxo (i.e., =O), then 2 hydrogens on the atom are replaced. When aromatic moieties are substituted by an oxo group, the aromatic ring is replaced by the corresponding partially unsaturated ring. For example a pyridyl group substituted by oxo is a pyridone. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation into an effective therapeutic agent.

Suitable groups that may be present on an "optionally substituted" position include, but are not limited to, e.g., halogen, cyano, hydroxyl, amino, nitro, oxo, azido, alkanoyl (such as a $C_2$-$C_6$ alkanoyl group such as acyl or the like (—(C=O)alkyl)); carboxamido; alkylcarboxamide; alkyl groups, alkoxy groups, alkylthio groups including those having one or more thioether linkages, alkylsulfinyl groups including those having one or more sulfinyl linkages, alkylsulfonyl groups including those having one or more sulfonyl linkages, mono- and di-aminoalkyl groups including groups having one or more N atoms, all of the foregoing optional alkyl substituents may have one or more methylene groups replaced by an oxygen or —NH—, and have from about 1 to about 8, from about 1 to about 6, or from 1 to about 4 carbon atoms, cycloalkyl; phenyl; phenylalkyl with benzyl being an exemplary phenylalkyl group, phenylalkoxy with benzyloxy being an exemplary phenylalkoxy group. Alkylthio and alkoxy groups are attached to the position they substitute by the sulfur or oxygen atom respectively.

A dash ("-") and ("$\wr$") that is not between two letters or symbols is used to indicate a point of attachment for a substituent.

"Alkyl" includes both branched and straight chain saturated aliphatic hydrocarbon groups, having the specified number of carbon atoms, generally from 1 to about 8 carbon atoms. The term $C_1$-$C_6$alkyl as used herein indicates an alkyl group having from 1, 2, 3, 4, 5, or 6 carbon atoms. Other embodiments include alkyl groups having from 1 to 8 carbon atoms, 1 to 4 carbon atoms or 1 or 2 carbon atoms, e.g. $C_1$-$C_8$alkyl, $C_1$-$C_4$alkyl, and $C_1$-$C_2$alkyl. When $C_0$-$C_n$ alkyl is used herein in conjunction with another group, for example, —$C_0$-$C_2$alkyl(phenyl), the indicated group, in this case phenyl, is either directly bound by a single covalent bond ($C_0$alkyl), or attached by an alkyl chain having the specified number of carbon atoms, in this case 1, 2, 3, or 4 carbon atoms. Alkyls can also be attached via other groups such as heteroatoms as in —O—$C_0$-$C_4$alkyl($C_3$-$C_7$cycloalkyl). Examples of alkyl include, but are not limited to, methyl, ethyl, n-propyl, isopropyl, n-butyl, 3-methylbutyl, t-butyl, n-pentyl, and sec-pentyl.

"Alkenyl" is a branched or straight chain aliphatic hydrocarbon group having one or more carbon-carbon double bonds that may occur at any stable point along the chain, having the specified number of carbon atoms. Examples of alkenyl include, but are not limited to, ethenyl and propenyl.

"Alkynyl" is a branched or straight chain aliphatic hydrocarbon group having one or more double carbon-carbon triple bonds that may occur at any stable point along the chain, having the specified number of carbon atoms.

"Alkoxy" is an alkyl group as defined above with the indicated number of carbon atoms covalently bound to the group it substitutes by an oxygen bridge (—O—). Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy. Similarly an "Alkylthio" or a "thioalkyl" group is an alkyl group as defined above with the indicated number of carbon atoms covalently bound to the group it substitutes by a sulfur bridge (—S—).

"Aryl" is a substituted stable monocyclic or polycyclic aromatic ring having 1 to 60 ring carbon atoms. Aryl groups include, but are not limited to, tolyl, xylyl, naphthyl, phenanthryl, and anthracenyl.

"Cycloalkyl" is a saturated hydrocarbon ring group, having the specified number of carbon atoms, usually from 3 to about 7 carbon atoms. Examples of cycloalkyl groups include cyclopropyl, cyclobutyl, cyclopentyl, or cyclohexyl as well as bridged or caged saturated ring groups such as norborane or adamantane. "—($C_0$-$C_n$ alkyl)cycloalkyl" is a cycloalkyl group attached to the position it substitutes either by a single covalent bond ($C_0$) or by an alkylene linker having 1 to n carbon atoms.

"Halo" or "halogen" means fluoro, chloro, bromo, or iodo.

"Heteroaryl" is a stable monocyclic aromatic ring having the indicated number of ring atoms which contains from 1 to 3, or in some embodiments from 1 to 2, heteroatoms chosen from N, O, and S, with remaining ring atoms being carbon, or a stable bicyclic or tricyclic system containing at least one 5- to 7-membered aromatic ring which contains from 1 to 3, or in some embodiments from 1 to 2, heteroatoms chosen from N, O, and S, with remaining ring atoms being carbon. Monocyclic heteroaryl groups typically have from 5 to 7 ring atoms. In some embodiments bicyclic heteroaryl groups are 9- to 10-membered heteroaryl groups, that is, groups containing 9 or 10 ring atoms in which one 5- to 7-member aromatic ring is fused to a second aromatic or non-aromatic ring. When the total number of S and O atoms in the heteroaryl group exceeds 1, these heteroatoms are not adjacent to one another. It is preferred that the total number of S and O atoms in the heteroaryl group is not more than 2. It is particularly preferred that the total number of S and O atoms in the aromatic heterocycle is not more than 1. Heteroaryl groups include, but are not limited to, oxazolyl, piperazinyl, pyranyl, pyrazinyl, pyrazolopyrimidinyl, pyrazolyl, pyridizinyl, pyridyl, pyrimidinyl, pyrrolyl, quinolinyl, tetrazolyl, thiazolyl, thienylpyrazolyl, thiophenyl, triazolyl, benzo[d]oxazolyl, benzofuranyl, benzothiazolyl, benzothiophenyl, benzoxadiazolyl, dihydrobenzodioxynyl, furanyl, imidazolyl, indolyl, isothiazolyl, and isoxazolyl.

"Heterocycle" is a saturated, unsaturated, or aromatic cyclic group having the indicated number of ring atoms containing from 1 to about 3 heteroatoms chosen from N, O, and S, with remaining ring atoms being carbon. Examples of heterocycle groups include piperazine and thiazole groups.

"Heterocycloalkyl" is a saturated cyclic group having the indicated number of ring atoms containing from 1 to about 3 heteroatoms chosen from N, O, and S, with remaining ring atoms being carbon. Examples of heterocycloalkyl groups include tetrahydrofuranyl and pyrrolidinyl groups.

"Haloalkyl" means both branched and straight-chain alkyl groups having the specified number of carbon atoms, substituted with 1 or more halogen atoms, generally up to the maximum allowable number of halogen atoms. Examples of haloalkyl include, but are not limited to, trifluoromethyl, difluoromethyl, 2-fluoroethyl, and penta-fluoroethyl.

"Haloalkoxy" is a haloalkyl group as defined above attached through an oxygen bridge (oxygen of an alcohol radical).

"Pharmaceutical compositions" means compositions comprising at least one active agent, such as a compound or salt of Formula (I), and at least one other substance, such as a carrier. Pharmaceutical compositions meet the U.S. FDA's GMP (good manufacturing practice) standards for human or non-human drugs.

"Carrier" means a diluent, excipient, or vehicle with which an active compound is administered. A "pharmaceutically acceptable carrier" means a substance, e.g., excipient, diluent, or vehicle, that is useful in preparing a pharmaceutical composition that is generally safe, non-toxic and neither biologically nor otherwise undesirable, and includes a carrier that is acceptable for veterinary use as well as human pharmaceutical use. A "pharmaceutically acceptable carrier" includes both one and more than one such carrier.

A "patient" means a human or non-human animal in need of medical treatment. Medical treatment can include treatment of an existing condition, such as a disease or disorder or diagnostic treatment. In some embodiments the patient is a human patient.

"Providing" means giving, administering, selling, distributing, transferring (for profit or not), manufacturing, compounding, or dispensing.

"Treatment" or "treating" means providing an active compound to a patient in an amount sufficient to measurably reduce any cancer symptom, slow cancer progression or cause cancer regression. In certain embodiments treatment of the cancer may be commenced before the patient presents symptoms of the disease.

A "therapeutically effective amount" of a pharmaceutical composition means an amount effective, when administered to a patient, to provide a therapeutic benefit such as an amelioration of symptoms, decrease cancer progression, or cause cancer regression.

A significant change is any detectable change that is statistically significant in a standard parametric test of statistical significance such as Student's T-test, where $p<0.05$.

Chemical Description

Compounds of Formula I or Formula II or Formula III may contain one or more asymmetric elements such as stereogenic centers, stereogenic axes and the like, e.g., asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, all optical isomers in pure form and mixtures thereof are encompassed. In these situations, the single enantiomers, i.e., optically active forms can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example a chiral HPLC column. All forms are contemplated herein regardless of the methods used to obtain them.

All forms (for example solvates, optical isomers, enantiomeric forms, tautomers, polymorphs, free compound and salts) of an active agent may be employed either alone or in combination.

The term "chiral" refers to molecules, which have the property of non-superimposability of the mirror image partner.

"Stereoisomers" are compounds, which have identical chemical constitution, but differ with regard to the arrangement of the atoms or groups in space.

A "diastereomer" is a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis, crystallization in the presence of a resolving agent, or chromatography, using, for example a chiral HPLC column.

"Enantiomers" refer to two stereoisomers of a compound, which are non-superimposable mirror images of one another. A 50:50 mixture of enantiomers is referred to as a racemic mixture or a racemate, which may occur where there has been no stereoselection or stereospecificity in a chemical reaction or process.

Stereochemical definitions and conventions used herein generally follow S. P. Parker, Ed., McGraw-Hill *Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and 1 or (+) and (−) are employed to designate the sign of rotation of plane-polarized light by the compound, with (−) or 1 meaning that the compound is levorotatory. A compound prefixed with (+) or d is dextrorotatory.

A "racemic mixture" or "racemate" is an equimolar (or 50:50) mixture of two enantiomeric species, devoid of optical activity. A racemic mixture may occur where there has been no stereoselection or stereospecificity in a chemical reaction or process.

"Tautomers" or "tautomeric forms" are constitutional isomers that readily interconvert, commonly by the migration of a hydrogen atom combined with a switch of a single bond and a double bond.

"Pharmaceutically acceptable salts" include derivatives of the disclosed compounds in which the parent compound is modified by making inorganic and organic, non-toxic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media such as ether, ethyl acetate, ethanol, isopropanol, or acetonitrile are used, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like. Lists of additional suitable salts may be found, e.g., in G. Steffen Paulekuhn, et al., *Journal of Medicinal Chemistry* 2007, 50, 6665 and *Handbook of Pharmaceutically Acceptable Salts: Properties, Selection and Use*, P. Heinrich Stahl and Camille G. Wermuth Editors, Wiley-VCH, 2002.

Chemical Description

Molecules which modulate CD206 are disclosed herein.

In addition to compounds of Formula I, Formula II, and Formula III shown in the SUMMARY section, the disclosure also includes compounds in which the variables, e.g. X and $R^1$ to $R^{25}$ carry the following definitions. The disclosure includes all combinations of these definitions so long as a stable compound results.

The disclosure includes the following particular embodiments of Formula I

Formula I

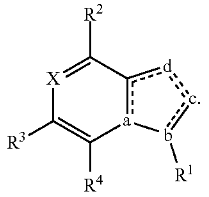

(A) In an embodiment, $R^1$ is hydrogen, halogen, hydroxyl, cyano, —$CO_2H$, $C_1$-$C_6$alkyl, $C_2$-$C_6$alkenyl, $C_2$-$C_6$alkynyl, $C_1$-$C_6$alkoxy, —($C_0$-$C_6$alkyl)cycloalkyl, $C_1$-$C_6$haloalkyl, —($C_0$-$C_6$alkyl)phenyl, —($C_0$-$C_6$alkyl)aryl, —($C_0$-$C_6$alkyl)heteroaryl, —C(O)$C_1$-$C_6$alkyl, —C(O)$NR^8R^9$, —($C_0$-$C_6$alkyl)$NR^5R^6$, —$CO_2R^6$, —$C_6H_4$—$R^7$, and a monocyclic or bicyclic heterocycle of 4 to 10 ring atoms having 1, 2, or 3 ring atoms independently chosen from N, S and 0.

$R^2$ and $R^4$ are H.

$R^3$ is hydrogen, halogen, hydroxyl, cyano, —$CO_2H$, $C_1$-$C_6$alkyl, $C_2$-$C_6$alkenyl, $C_2$-$C_6$alkynyl, $C_1$-$C_6$alkoxy, —($C_0$-$C_6$alkyl)cycloalkyl, $C_1$-$C_6$haloalkyl, —($C_0$-$C_6$alkyl)phenyl, —($C_0$-$C_6$alkyl)aryl, —($C_0$-$C_6$alkyl)heteroaryl, —C(O)$C_1$-$C_6$alkyl, —C(O)$NR^5R^6$, ($C_0$-$C_6$alkyl)$NR^8R^9$, —$CO_2R^6$, and —$C_6H_4$—$R^7$.

a, b, c, and d are each independently chosen at each occurrence from N, C and CH.

X is N.

$R^5$, and $R^6$ are each independently chosen at each occurrence from hydrogen, halogen, hydroxy, $C_1$-$C_6$alkyl, $C_1$-$C_6$haloalkyl, $C_1$-$C_6$hydroxyalkyl, $C_1$-$C_6$alkoxy, a substituted or unsubstituted —($C_0$-$C_6$alkyl)cycloalkyl, —($C_0$-$C_6$alkyl)phenyl, —($C_0$-$C_6$alkyl)aryl, —($C_0$-$C_6$alkyl)heteroaryl, —C(O)$C_1$-$C_6$alkyl, —C(O)($C_0$-$C_6$alkyl)phenyl, —($C_0$-$C_6$alkyl)$NR^8R^9$, —C(O)($C_0$-$C_6$alkyl)aryl, —C(O)($C_0$-$C_6$alkyl)heteroaryl, and a 4- to 7-membered heterocycloalkyl ring having 1, 2, or 3 ring atoms independently chosen from N, O, and S.

Any $R^5$ and $R^6$ bound to the same nitrogen atom may be taken together to form a 4- to 7-membered monocyclic heterocycloalkyl ring or 6- to 11-membered bridged bicyclic heterocycloalkyl ring, which heterocycloalkyl ring contains 0, 1, or 2 additional heteroatoms chosen from N, O, S, S(O), and $SO_2$ which heterocycloalkyl ring is optionally substituted at any carbon or hetero ring atom with halogen, hydroxyl, cyano, oxo, dioxo, $C_1$-$C_6$alkyl, $C_1$-$C_6$alkoxy, $C_1$-$C_6$haloalkyl, —($C_0$-$C_6$alkyl)cycloalkyl, —($C_0$-$C_6$alkyl)phenyl, —($C_0$-$C_6$alkyl)aryl, —($C_0$-$C_6$alkyl)$CO_2R^8$, —($C_0$-$C_6$alkyl)C(O)$NR^8R^9$, —($C_1$-$C_6$alkyl)$OR^8$, —C(O)$C_1$-$C_6$alkyl, —($C_0$-$C_6$alkyl)$NR^8R^9$, or —C(O)($C_0$-$C_6$alkyl)$NR^8R^9$.

$R^7$ is hydrogen, halogen, hydroxyl, cyano, —$CO_2H$, $C_1$-$C_6$alkyl, $C_2$-$C_6$alkenyl, $C_2$-$C_6$alkynyl, $C_1$-$C_6$alkoxy, $C_1$-$C_6$haloalkyl, —($C_0$-$C_6$alkyl)cycloalkyl, —($C_0$-$C_6$alkyl)phenyl, —($C_0$-$C_6$alkyl)aryl, —($C_0$-$C_6$alkyl)heteroaryl, —$CO_2R^8$, —C(O)$C_1$-$C_6$alkyl, —C(O)$C_2$-$C_6$alkenyl, —C(O)$C_2$-$C_6$alkynyl, —C(O)$C_1$-$C_6$alkoxy, —C(O)$C_1$-$C_6$hydroxyalkyl, —C(O)—($C_0$-$C_6$alkyl)cycloalkyl, —C(O)—($C_0$-$C_6$alkyl)phenyl, —C(O)—($C_0$-$C_6$alkyl)aryl, —C(O)—($C_0$-$C_6$alkyl)heteroaryl, —C(O)$NR^8R^9$, —C(O)$NR^5R^6$, —C(O)—($C_0$-$C_6$alkyl)$NR^5R^6$, —C(O)—$NR^B$—($C_0$-$C_6$alkyl)$NR^5R^6$, or ($C_0$-$C_6$alkyl)$NR^5R^6$.

$R^8$ and $R^9$ are each independently chosen at each occurrence from hydrogen, halogen, $C_1$-$C_6$ alkyl, $C_1$-$C_6$alkoxy, $C_1$-$C_6$haloalkyl, —($C_0$-$C_6$alkyl)phenyl, —($C_0$-$C_6$alkyl)aryl, —($C_0$-$C_6$alkyl)$NR^5R^6$, —$CO_2R^6$, —C(O)$C_1$-$C_6$alkyl, and —($C_0$-$C_6$alkyl)cycloalkyl.

(B) In an embodiment, $R^1$ is —$C_6H_4$—$R^7$.

$R^2$ and $R^4$ are H.

$R^3$ is —($C_0$-$C_6$alkyl)phenyl, —($C_0$-$C_6$alkyl)aryl, or —($C_0$-$C_6$alkyl)heteroaryl.

a, c, and X are N.

b is C.

d is CH.

$R^7$ is —C(O)$NR^5R^6$ or —C(O)—$NR^8$—($C_0$-$C_6$alkyl)$NR^5R^6$.

$R^5$ and $R^6$ are each independently chosen at each occurrence from hydrogen, a substituted or unsubstituted —($C_0$-$C_6$alkyl)cycloalkyl, —($C_0$-$C_6$alkyl)heteroaryl, $C_1$-$C_6$hydroxyalkyl, $C_1$-$C_6$alkoxy, —($C_0$-$C_6$alkyl)$NR^8R^9$, and a 4- to 7-membered heterocycloalkyl ring having 1, 2, or 3 ring atoms independently chosen from N, O, and S.

Any $R^5$ and $R^6$ bound to the same nitrogen atom may be taken together to form a 4- to 7-membered monocyclic heterocycloalkyl ring or 6- to 11-membered bridged bicyclic heterocycloalkyl ring, which heterocycloalkyl ring contains 0, 1, or 2 additional heteroatoms chosen from N, O, S, S(O), and $SO_2$ which heterocycloalkyl ring is optionally substituted at any carbon or hetero ring atom with halogen, hydroxyl, cyano, oxo, dioxo, $C_1$-$C_6$alkyl, $C_1$-$C_6$alkoxy, $C_1$-$C_6$haloalkyl, —($C_0$-$C_6$alkyl)cycloalkyl, —($C_0$-$C_6$alkyl)phenyl, —($C_0$-$C_6$alkyl)aryl, —($C_0$-$C_6$alkyl)$CO_2R^8$, —($C_0$-$C_6$alkyl)C(O)$NR^8R^9$, —($C_1$-$C_6$alkyl)$OR^8$, —$CO_2R^8$, —C(O)$C_1$-$C_6$alkyl, —($C_0$-$C_6$alkyl)$NR^8R^9$, or —C(O)($C_0$-$C_6$alkyl)$NR^8R^9$.

$R^8$ and $R^9$ are each independently chosen at each occurrence from hydrogen, halogen, $C_1$-$C_6$ alkyl, $C_1$-$C_6$alkoxy, $C_1$-$C_6$haloalkyl, —($C_0$-$C_6$alkyl)phenyl, —($C_0$-$C_6$alkyl)aryl, —($C_0$-$C_6$alkyl)$NR^5R^6$, —$CO_2R^6$, —C(O)$C_1$-$C_6$alkyl, and —($C_0$-$C_6$alkyl)cycloalkyl.

(C) In an embodiment, the compound of Formula I is a compound represented by at least one of Compound 1, and Compound 4 to Compound 29:

Compound 1

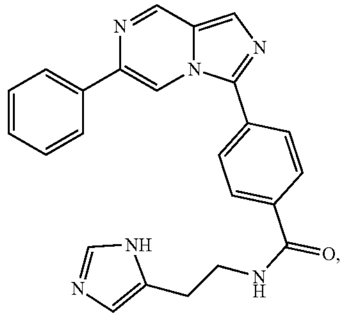

Compound 4

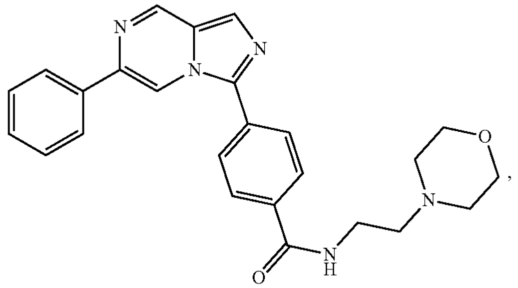

Compound 5

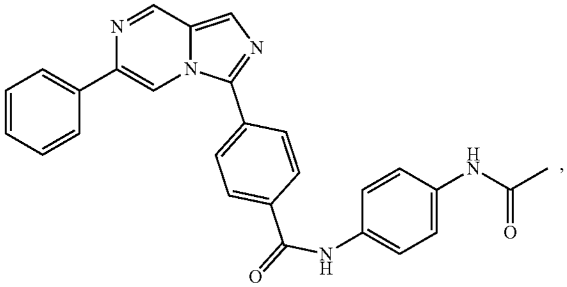

Compound 6

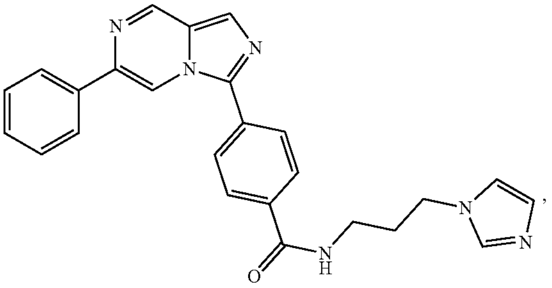

-continued
Compound 7
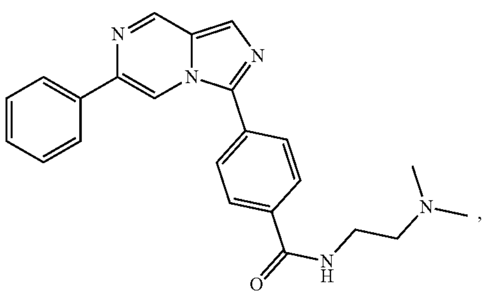
Compound 8
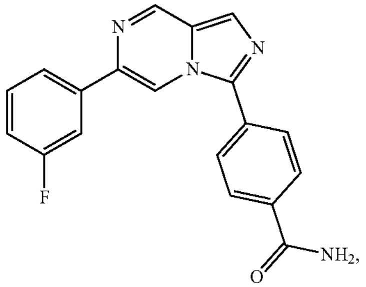
Compound 9
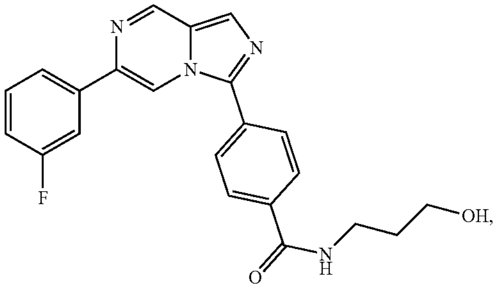
Compound 10
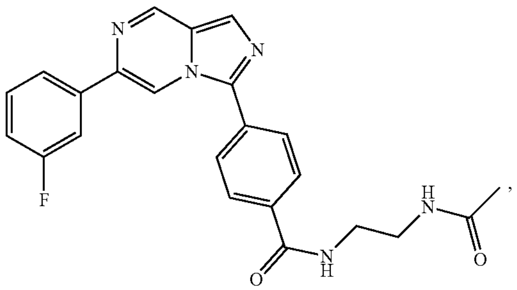
Compound 11
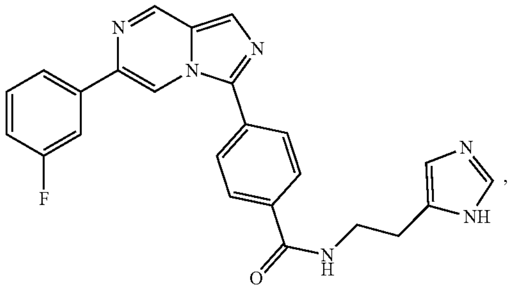
-continued
Compound 12
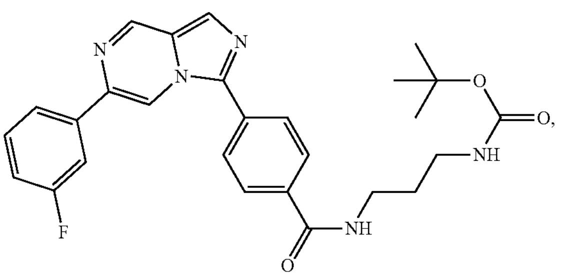
Compound 13
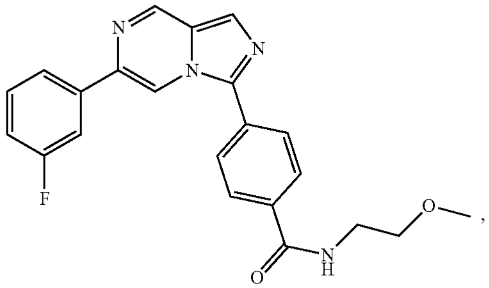
Compound 14
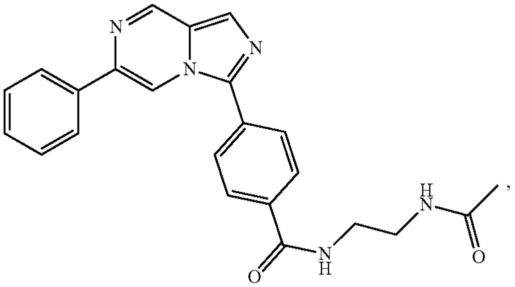
Compound 15
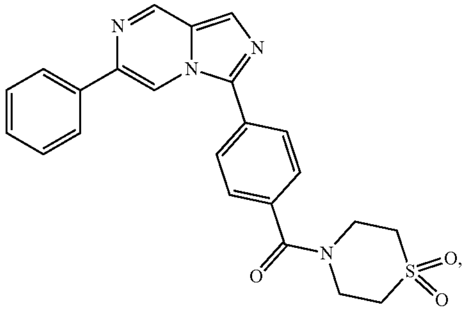
Compound 16
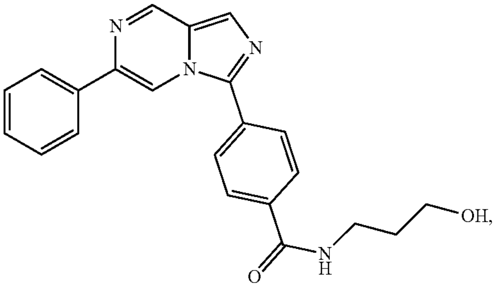

-continued
Compound 17
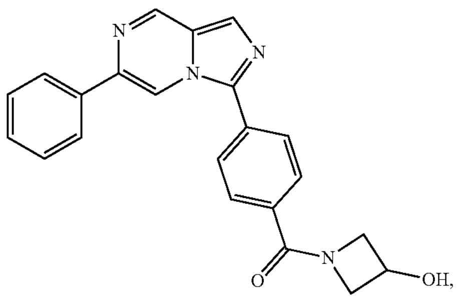
Compound 18
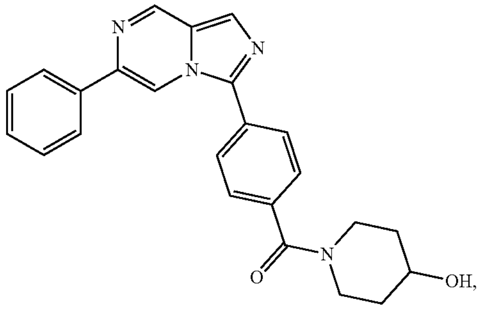
Compound 19
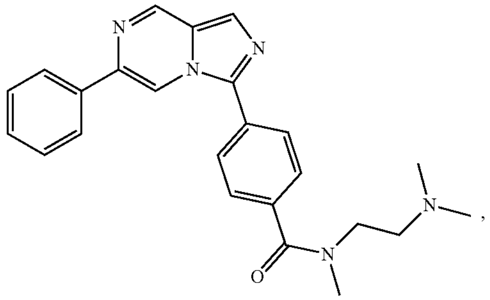
Compound 20
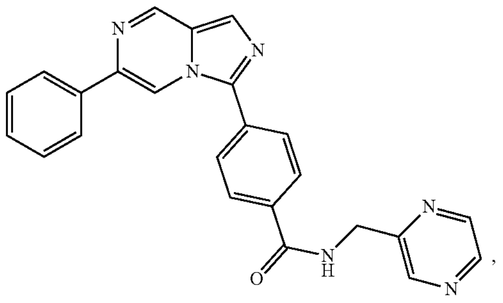
Compound 21
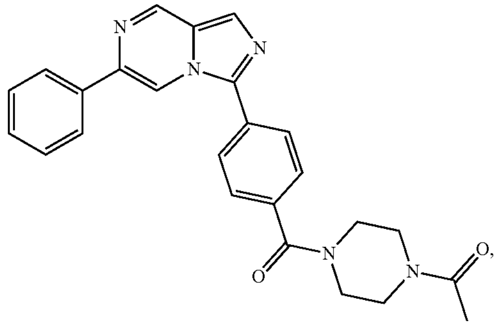
-continued
Compound 22
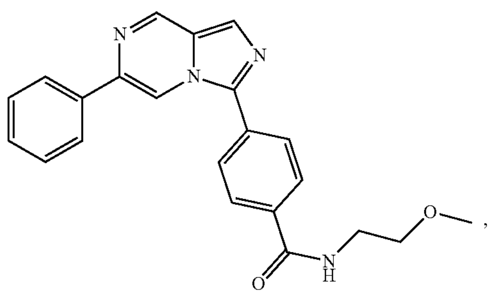
Compound 23
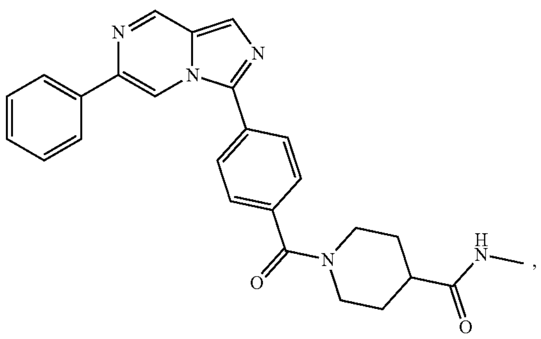
Compound 24
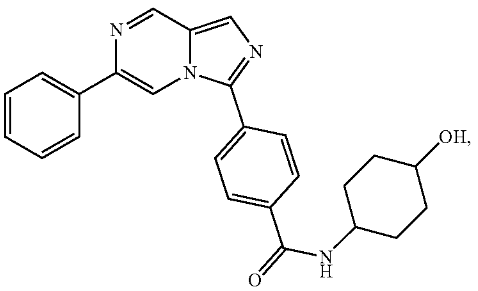
Compound 25
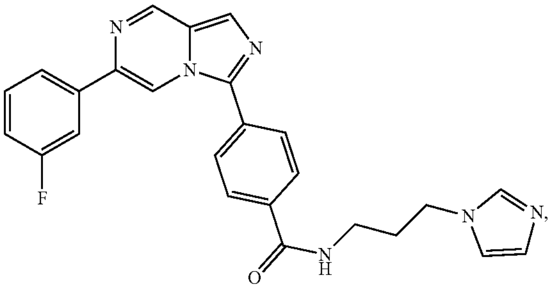
Compound 26
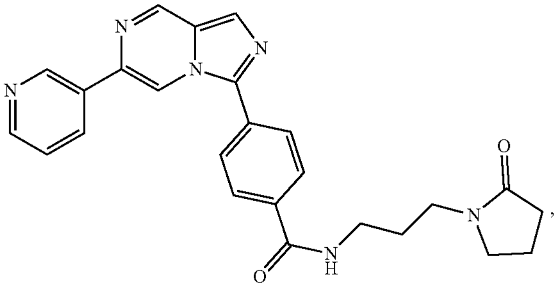

-continued

Compound 27

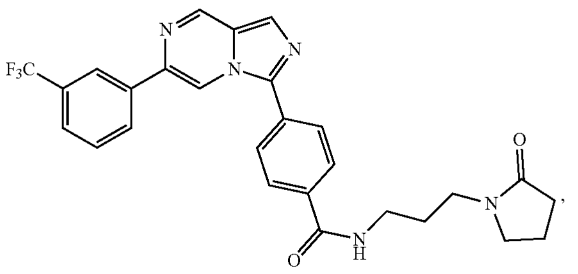

Compound 28

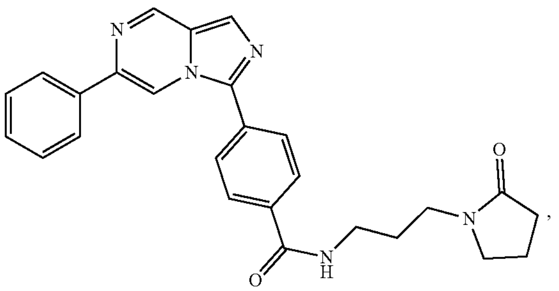

Compound 29

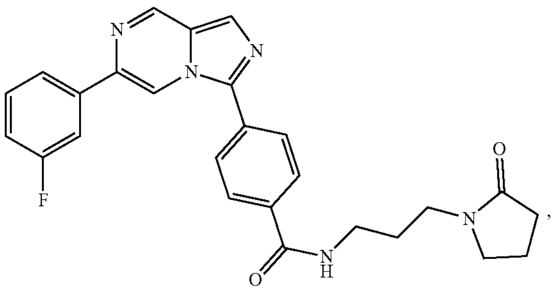

or a pharmaceutically acceptable salt thereof.

(D) In an embodiment, $R^1$ is —$C_6H_4$—$R^7$.

$R^2$ and $R^4$ are hydrogen.

$R^3$ is —($C_0$-$C_6$alkyl)phenyl, —($C_0$-$C_6$alkyl)aryl, or —($C_0$-$C_6$alkyl)heteroaryl.

a, c, d, and X are N.

b is C.

$R^7$ is —C(O)—$NR^{B}$—($C_0$-$C_6$alkyl)$NR^5R^6$.

$R^5$ and $R^6$ bound to the same nitrogen atom may be taken together to form a 4- to 7-membered monocyclic heterocycloalkyl ring or 6- to 11-membered bridged bicyclic heterocycloalkyl ring, which heterocycloalkyl ring contains 0, 1, or 2 additional heteroatoms chosen from N, O, S, S(O), and $SO_2$ which heterocycloalkyl ring is optionally substituted at any carbon or hetero ring atom with halogen, hydroxyl, cyano, oxo, dioxo, $C_1$-$C_6$alkyl, $C_1$-$C_6$alkoxy, $C_1$-$C_6$haloalkyl, —($C_0$-$C_6$alkyl)cycloalkyl, —($C_0$-$C_6$alkyl)phenyl, or —($C_0$-$C_6$alkyl)aryl.

$R^8$ is hydrogen.

(E) In an embodiment, the compound of Formula I is a compound represented by at least one of Compound 30 and Compound 31:

Compound 30

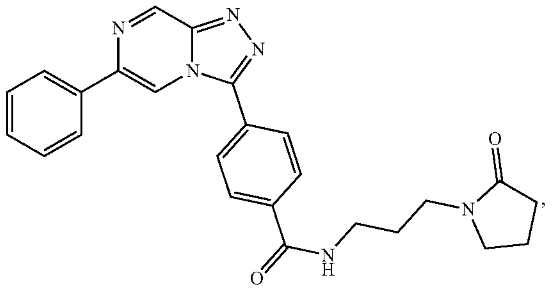

Compound 31

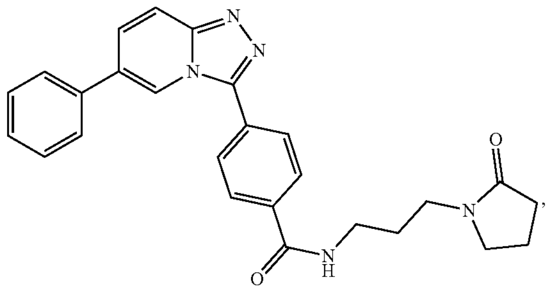

or a pharmaceutically acceptable salt thereof.

(F) In an embodiment, $R^1$ is —$C_6H_4$—$R^7$.

$R^2$ and $R^4$ are hydrogen.

$R^3$ is —($C_0$-$C_6$alkyl)phenyl, —($C_0$-$C_6$alkyl)aryl, or —($C_0$-$C_6$alkyl)heteroaryl.

a is C.

b, d, and X are N.

c is CH.

$R^7$ is —C(O)—$NR^8$—($C_0$-$C_6$alkyl)$NR^5R^6$.

$R^5$ and $R^6$ bound to the same nitrogen atom may be taken together to form a 4- to 7-membered monocyclic heterocycloalkyl ring or 6- to 11-membered bridged bicyclic heterocycloalkyl ring, which heterocycloalkyl ring contains 0, 1, or 2 additional heteroatoms chosen from N, O, S, S(O), and $SO_2$ which heterocycloalkyl ring is optionally substituted at any carbon or hetero ring atom with halogen, hydroxyl, cyano, oxo, dioxo, $C_1$-$C_6$alkyl, $C_1$-$C_6$alkoxy, $C_1$-$C_6$haloalkyl, —($C_0$-$C_6$alkyl)cycloalkyl, —($C_0$-$C_6$alkyl)phenyl, or —($C_0$-$C_6$alkyl)aryl.

$R^8$ is hydrogen.

(G) In an embodiment, the compound of Formula I is a compound represented by Compound 32:

Compound 32

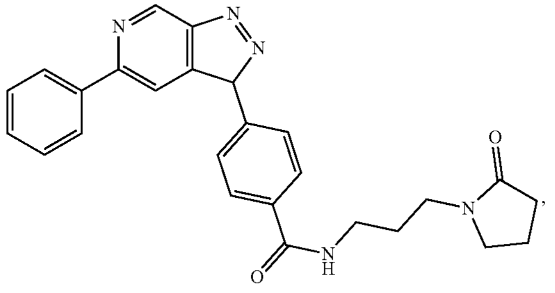

or a pharmaceutically acceptable salt thereof.

(H) In an embodiment, $R^1$ is —$C_6H_4$—$R^7$.

$R^2$ and $R^4$ are hydrogen.

$R^3$ is —($C_0$-$C_6$alkyl)phenyl, —($C_0$-$C_6$alkyl)aryl, or —($C_0$-$C_6$alkyl)heteroaryl.

a is C.

b and X are N.

c and d are CH.

$R^7$ is —C(O)—$NR^B$—($C_0$-$C_6$alkyl)$NR^5R^6$.

$R^5$ and $R^6$ bound to the same nitrogen atom may be taken together to form a 4- to 7-membered monocyclic heterocycloalkyl ring or 6- to 11-membered bridged bicyclic heterocycloalkyl ring, which heterocycloalkyl ring contains 0, 1, or 2 additional heteroatoms chosen from N, O, S, S(O), and $SO_2$ which heterocycloalkyl ring is optionally substituted at any carbon or hetero ring atom with halogen, hydroxyl, cyano, oxo, dioxo, $C_1$-$C_6$alkyl, $C_1$-$C_6$alkoxy, $C_1$-$C_6$haloalkyl, —($C_0$-$C_6$alkyl)cycloalkyl, —($C_0$-$C_6$alkyl)phenyl, or —($C_0$-$C_6$alkyl)aryl.

$R^8$ is hydrogen.

(I) In an embodiment, the compound of Formula I is a compound represented by Compound 33:

Compound 33

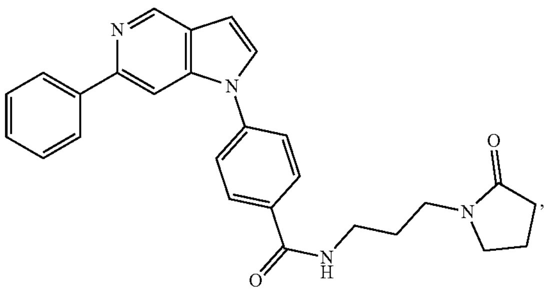

or a pharmaceutically acceptable salt thereof.

The disclosure includes the following particular embodiments of Formula II

Formula II

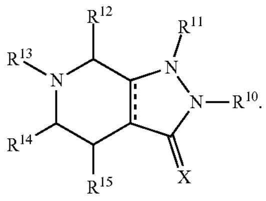

In some embodiments the compound of Formula II is a compound of Formula IIA

Formula IIA

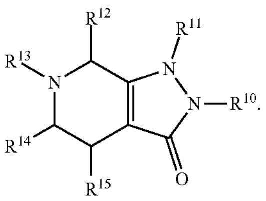

(A) In an embodiment, $R^{10}$ and $R^{11}$ are each independently chosen at each occurrence from —($C_0$-$C_6$alkyl)phenyl, —($C_0$-$C_6$alkyl)aryl, and —($C_0$-$C_6$alkyl)heteroaryl.

$R^{12}$, $R^{14}$ and $R^{15}$ are hydrogen.

$R^{13}$ is —C(O)heteroaryl.

(B) In an embodiment, $R^{10}$ is —($C_0$-$C_6$alkyl)phenyl.

$R^{11}$ is —($C_0$-$C_6$alkyl)heteroaryl.

$R^{12}$, $R^{14}$ and $R^{15}$ are hydrogen.

$R^{13}$ is —C(O)heteroaryl.

(C) In an embodiment, the compound of Formula IIA is Compound 2:

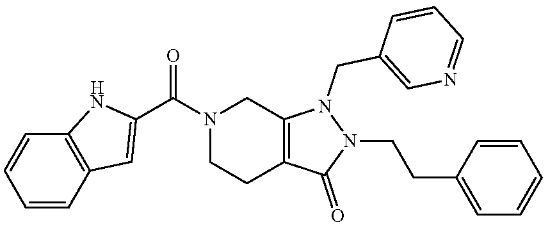 [SMILES: O=C(c1cc2ccccc2[nH]1)N1CCc2c(n(Cc3cccnc3)n(CCc3ccccc3)c2=O)C1]

or a pharmaceutically acceptable salt thereof.

The disclosure includes the following particular embodiments of Formula III

Formula III

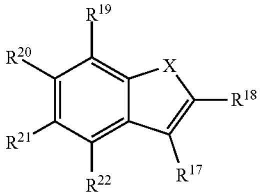

(A) In an embodiment, $R^{17}$ is —C(O)$C_1$-$C_6$alkyl, —C(O)($C_0$-$C_6$alkyl)phenyl, —C(O)($C_0$-$C_6$alkyl)aryl, or —C(O)($C_0$-$C_6$alkyl)heteroaryl.

$R^{18}$ is $C_1$-$C_6$alkyl, $C_2$-$C_6$alkenyl, $C_2$-$C_6$alkynyl, $C_1$-$C_6$alkoxy, —($C_0$-$C_6$alkyl)cycloalkyl, $C_1$-$C_6$haloalkyl, —($C_0$-$C_6$alkyl)phenyl, —($C_0$-$C_6$alkyl)aryl, or —($C_0$-$C_6$alkyl)heteroaryl.

$R^{19}$, $R^{20}$ and $R^{22}$ are hydrogen.

$R^{21}$ is —$NR^{23}R^{24}$.

X is chosen at each occurrence from O and S.

$R^{23}$ and $R^{24}$ are each independently chosen at each occurrence from —S(O)phenyl, —S(O)aryl, —S(O)heteroaryl, —$SO_2$phenyl, —$SO_2$aryl, —$SO_2$heteroaryl, —($C_0$-$C_6$alkyl)cycloalkyl, and —$CO_2R^{25}$.

$R^{25}$ is $C_1$-$C_6$alkyl, —($C_0$-$C_6$alkyl)cycloalkyl, —($C_0$-$C_6$alkyl)aryl, or —($C_0$-$C_6$alkyl)phenyl.

(B) In an embodiment, $R^{17}$ is —C(O)$C_1$-$C_6$alkyl.

$R^{18}$ is $C_1$-$C_6$alkyl.

$R^{19}$, $R^{20}$ and $R^{22}$ are hydrogen.

$R^{21}$ is —$NR^{23}R^{24}$.

X is oxygen.

$R^{23}$ and $R^{24}$ are each independently chosen at each occurrence from a substituted or unsubstituted aryl sulfonyl, —$CO_2R^{25}$, —$SO_2$phenyl, —$SO_2$aryl, and —$SO_2R^{25}$.

$R^{25}$ is phenyl.

In an embodiment, the compound of Formula III is Compound 3:

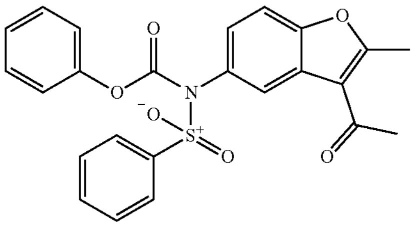 [SMILES: CC(=O)c1c(C)oc2ccc(N(C(=O)Oc3ccccc3)[S+](=O)([O-])c3ccccc3)cc12]

or a pharmaceutically acceptable salt thereof.

Treatment Methods

The compounds of Formula I, Formula II, or Formula III or a salt thereof, as well as pharmaceutical compositions comprising the compounds, are useful for treating cancer, including effecting tumor regression in vivo. The method of treating cancer or effecting tumor regression comprises providing to a patient an effective amount of a compound of Formula I, Formula II, or Formula III. In an embodiment the patient is a mammal, and more specifically a human. The disclosure also provides methods of treating non-human patients such as companion animals, e.g. cats, dogs, and livestock animals. An effective amount of a pharmaceutical composition may be an amount sufficient to inhibit the progression of cancer or a cancerous tumor; or cause a regression of a cancer or a cancerous tumor.

An effective amount of a compound or pharmaceutical composition described herein will also provide a sufficient concentration of a compound of Formula I, Formula II, or Formula III when administered to a patient. A sufficient concentration is a concentration of the compound in the patient's body necessary to combat the disorder. Such an amount may be ascertained experimentally, for example by assaying blood concentration of the compound, or theoretically, by calculating bioavailability.

Methods of treatment include providing certain dosage amounts of a compound of Formula I, Formula II, or Formula III to a patient. Dosage levels of each compound of from about 20 milligram (mg) or less per kilogram of body weight per day are useful in the treatment of the above-indicated conditions Frequency of dosage may also vary depending on the compound used and the particular disease treated.

The compounds of Formula I, Formula II, or Formula III may be used to treat cancers and effect regression of tumors, including cancerous tumors. In certain embodiments, the patient is suffering from a cell proliferative disorder or disease. The cell proliferative disorder can be cancer, tumor (cancerous or benign), neoplasm, neovascularization, or melanoma. Cancers for treatment include both solid and disseminated cancers. Exemplary solid cancers (tumors) that may be treated by the methods provided herein include e.g. cancers of the lung, prostate, breast, liver, colon, breast, kidney, pancreas, brain, skin including malignant melanoma and Kaposi's sarcoma, testes or ovaries, carcinoma, kidney cancer (renal cell), and sarcoma.

Cancers that may be treated with a compound of Formula I, Formula II, or Formula III also include bladder cancer, breast cancer, colon cancer, endometrial cancer, lung cancer, bronchial cancer, melanoma, Non-Hodgkins lymphoma, cancer of the blood, pancreatic cancer, prostate cancer, thyroid cancer, brain or spinal cancer, and leukemia. Exemplary disseminated cancers include leukemias or lymphoma including Hodgkin's disease, multiple myeloma and mantle cell lymphoma (MCL), chronic lymphocytic leukemia (CLL), T-cell leukemia, multiple myeloma, and Burkitt's lymphoma. Particularly included herein are methods of treating cancer by providing a compound of Formula I, Formula II, or Formula III to a patient wherein the cancer is a solid tumor or disseminated cancer.

Further included are methods of treating cancer by providing a compound of Formula I, Formula II, or Formula III to a patient wherein the cancer is selected from glioma (glioblastoma), acute myelogenous leukemia, acute myeloid leukemia, myelodysplastic/myeloproliferative neoplasms, sarcoma, chronic myelomonocytic leukemia, non-Hodgkin lymphoma, astrocytoma, melanoma, non-small cell lung cancer, cholangiocarcinomas, chondrosarcoma, or colon cancer.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

A compound of Formula I, Formula II, or Formula III may be administered singularly (i.e., sole therapeutic agent of a regime) to treat diseases and conditions such as undesired cell proliferation, cancer, and/or tumor growth or may be administered in combination with another active agent. One or more compounds of Formula I, Formula II, or Formula III may be administered in coordination with a regime of one or more other chemotherapeutic agents such as an antineoplastic drug, e.g., an alkylating agent (e.g., mechloroethamine, chlorambucil, cyclophosamide, melphalan, or ifosfamide), an antimetabolite such as a folate antagonist (e.g., methotrexate), a purine antagonist (e.g. 6-mercaptopurine) or a pyrimidine antagonist (e.g., 5-fluorouracil). Other, non-limiting examples of chemotherapeutic agents that might be used in coordination with one or more compounds of Formula I, Formula II, or Formula III include taxanes and topoisomerase inhibitors. In addition, other non-limiting examples of active therapeutics include biological agents, such as monoclonal antibodies or IgG chimeric molecules, that achieve their therapeutic effect by specifically binding to a receptor or ligand in a signal transduction pathway associated with cancer (e.g. therapeutic antibodies directed against CD20 (e.g. rituximab) or against VEGF (e.g. bevacizumab)).

Methods of treatment provided herein are also useful for treatment of mammals other than humans, including for veterinary applications such as to treat horses and livestock e.g. cattle, sheep, cows, goats, swine and the like, and pets (companion animals) such as dogs and cats.

For diagnostic or research applications, a wide variety of mammals will be suitable subjects including rodents (e.g. mice, rats, hamsters), rabbits, primates and swine such as inbred pigs and the like. Additionally, for in vitro applications, such as in vitro diagnostic and research applications, body fluids (e.g., blood, plasma, serum, cellular interstitial fluid, saliva, feces and urine) and cell and tissue samples of the above subjects will be suitable for use.

In an embodiment, the invention provides a method of treating a cancer disorder in a patient identified as in need of such treatment, the method comprising providing to the patient an effective amount of a compound of Formula I, Formula II, or Formula III. The compounds and salts of Formula I, Formula II, or Formula III provided herein may be administered alone, or in combination with one or more other active agent.

In an embodiment, the cancer to be treated is characterized by the selective targeting M2 macrophages and the reprogramming of M2 macrophages towards a M1 phenotype in a patient.

Figure 19:
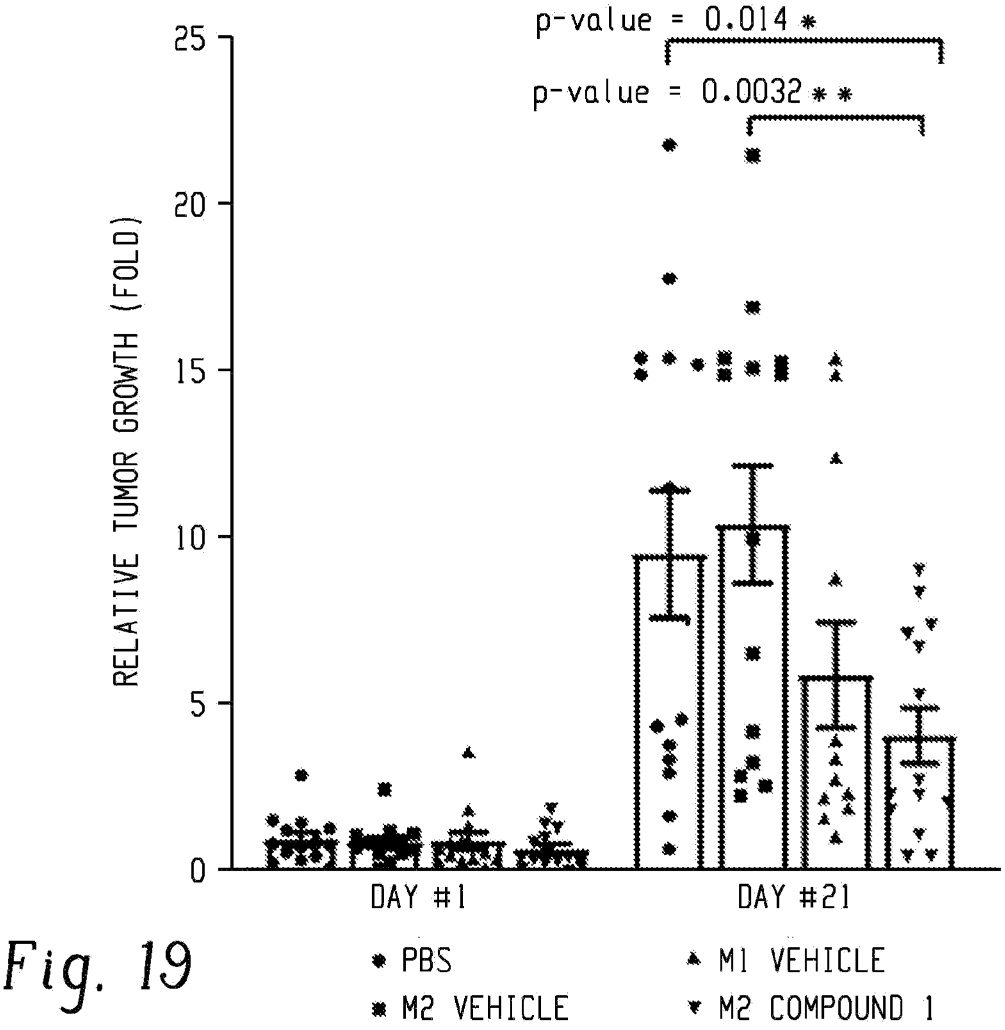
FIG. 19 shows relative tumor growth of KPC allograft tumors grown in C57BL/6 mice to show that after adaptive transfer of M2 macrophages via intratumoral injections, M2 macrophages when treated with Compound 1 compared to vehicle restricted tumor growth similar to injection of equal number of M1 macrophages, when the frequency of intratumoral injections was 3 times a week, and frequency of measurement was 2 times a week illustrating that treatment with Compound 1 showed reduction of tumor growth with M2 macrophages pretreated with Compound 1 but not when pretreated with vehicle indicating M2 macrophages treated with Compound 1 and injected into tumors have a tumor-restricting effect.

As shown in FIG. 19 Compound 1 showed reduction of tumor with M2 macrophages in M2 macrophages adaptive transfer study in KPC allograft model in C57BL/6 mouse model compared to vehicle, where the frequency of intratumoral injections was 3 times a week, and frequency of measurement was 2 times a week.

Figure 3A:
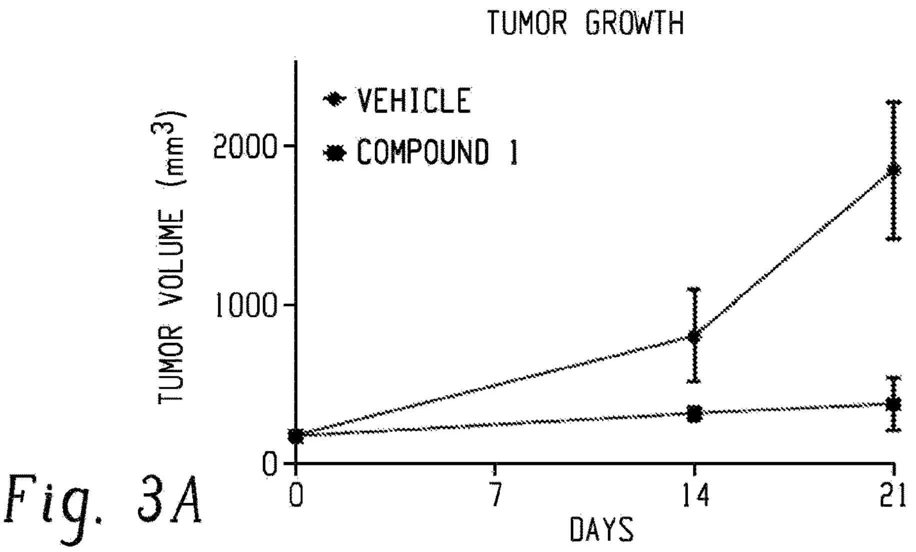
FIG. 3A shows a graph of Tumor Volume in cubic millimeters ($mm^3$) versus Number of Treatment Days illustrating change in tumor volume during in vivo testing of Compound 1 in fully immune-competent transgenic Kras (G12D)/Trp53(R172H)/Pdx-1-Cre (KPC) mice (murine pancreatic cancer model)
Figure 3B:
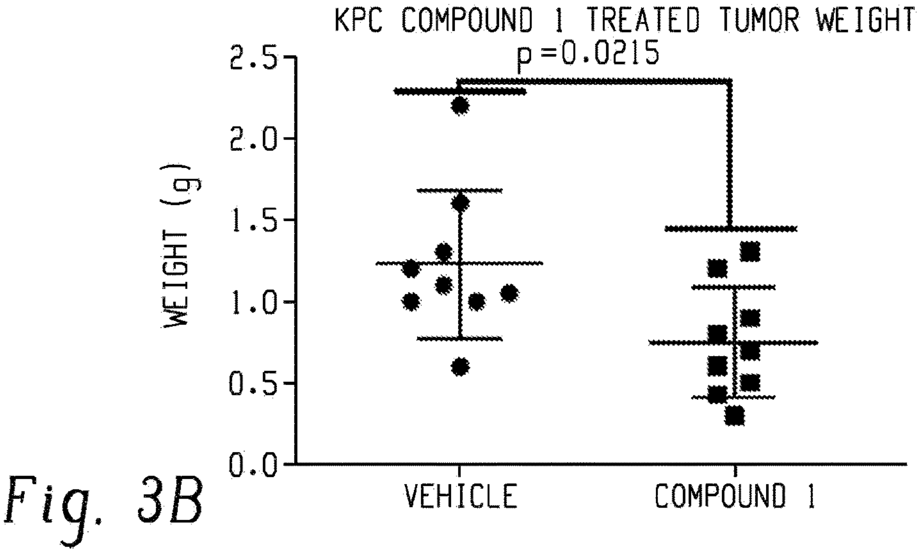
FIG. 3B shows a Tumor Weight change in vehicle and Compound 1 at study endpoint in grams of wet weight illustrating a change in tumor weight during in vivo testing of Compound 1 in fully immune-competent transgenic Kras (G12D)/Trp53(R172H)/Pdx-1-Cre (KPC) mice (murine pancreatic cancer model)
Figure 3C:
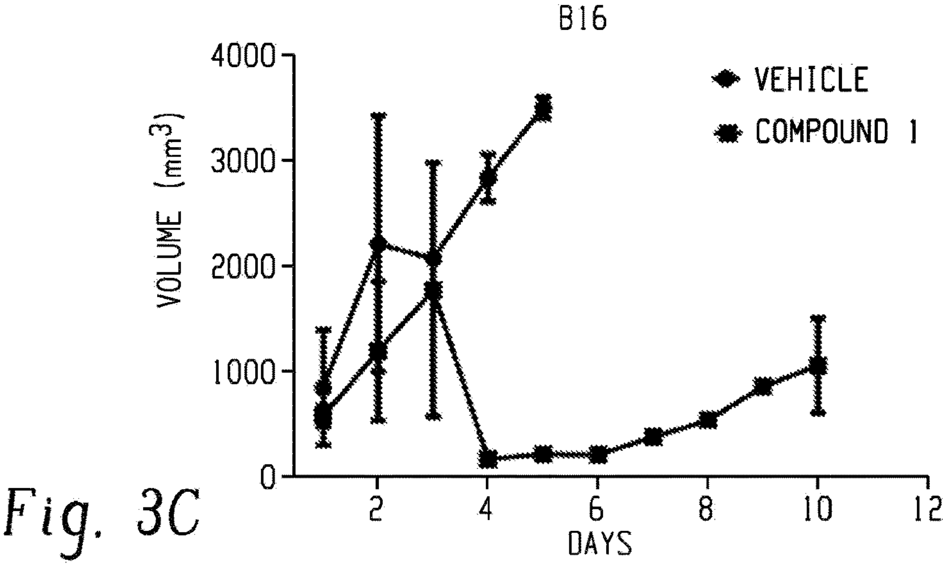
FIG. 3C shows a graph of Tumor Volume in cubic millimeters ($mm^3$) versus Number of Treatment Days illustrating change in tumor volume during in vivo testing of Compound 1 in a syngeneic, immune-competent B16.F10 allograft model (murine melanoma model)

Tumor growth was suppressed during in vivo testing of Compound 1 in fully immune-competent transgenic Kras (G12D)/Trp53(R172H)/Pdx-1-Cre (KPC) mice (murine pancreatic cancer model) compared to vehicle as shown in FIG. 3B. This point was further illustrated in FIGS. 3A and 3C where comparison of tumor volume for mice treated with Compound-1 and untreated mice (vehicle) is shown.

Figure 18A:
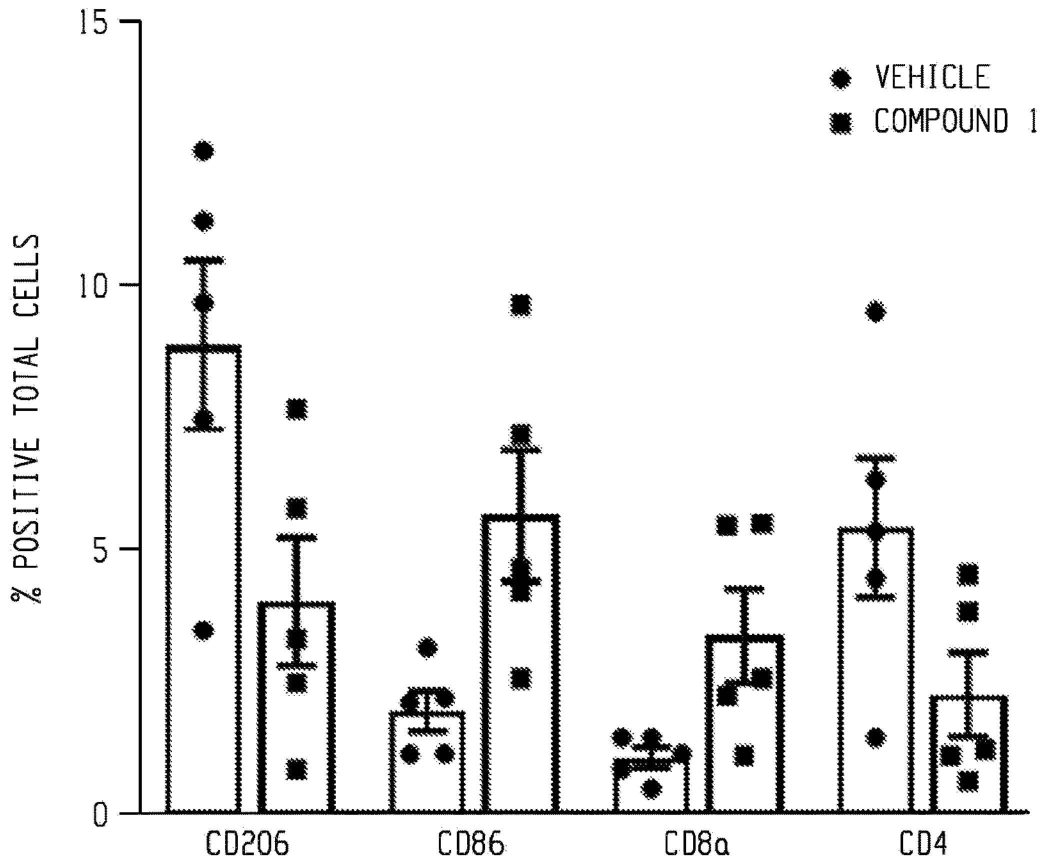
FIGS. 18A to 18C show reprogramming of the intratumoral immune landscape by Compound 1 in autochthonous KPC tumors, FIG. 18A show graphs of percent positive cell fractions of total cells in tumors measured by quantitative flow cytometry in KPC tumors (CD206=M2 macrophages; CD86=M1 macrophages; CD8a=CD8 positive T cells; CD4=CD4 positive T cells) treated with Compound 1 compared to vehicle illustrating that treatment with Compound 1 showing reduction of CD206 macrophages, shift from $CD206^{high}$ M2 to CD86-positive M1 macrophages, and increase in intratumoral CD8 cells.
Figure 18B:
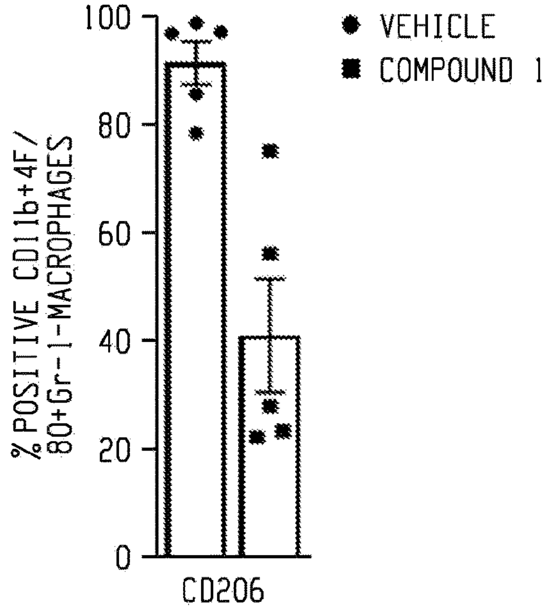
Figure 18C:
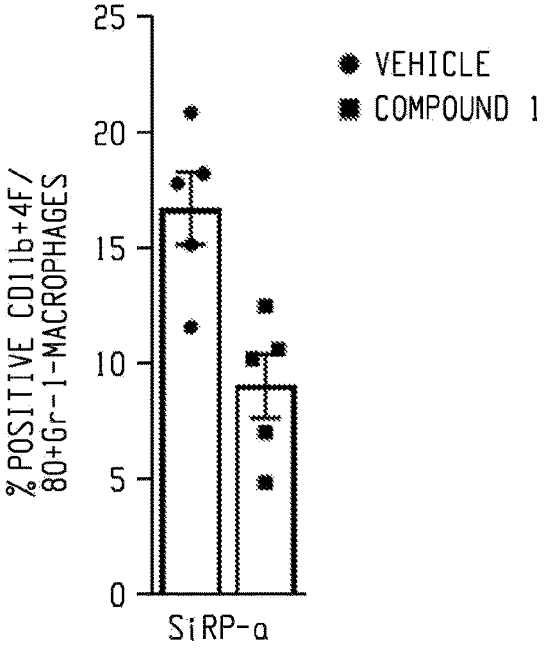
Figure 18D:
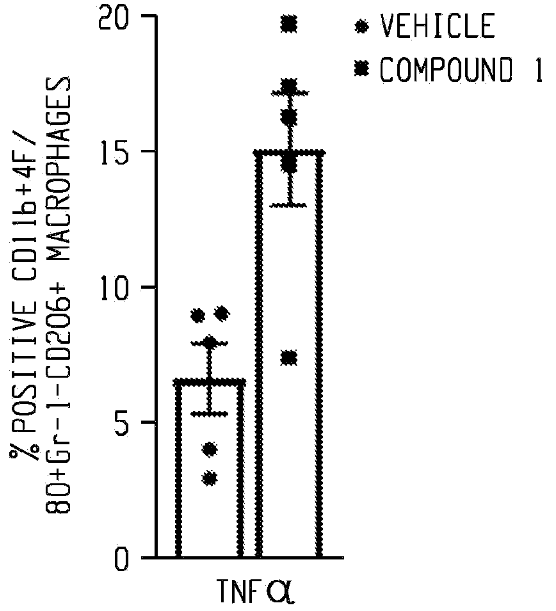
FIGS. 18D to 18I show graphs of percent positive cell fractions of intratumoral M1 and M2 macrophage populations measured by quantitative flow cytometry in KPC tumors to indicate shift in cytokine profile after treatment with Compound 1 for three weeks in KPC mice compared to vehicle illustrating that Compound 1 showed induction of M1 markers compared to vehicle in both intratumoral M1 and intratumoral M2 macrophage populations.
Figure 18F:
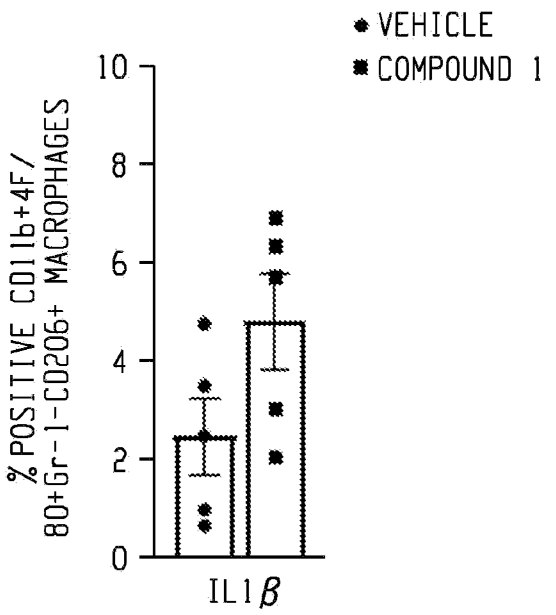
Figure 18E:
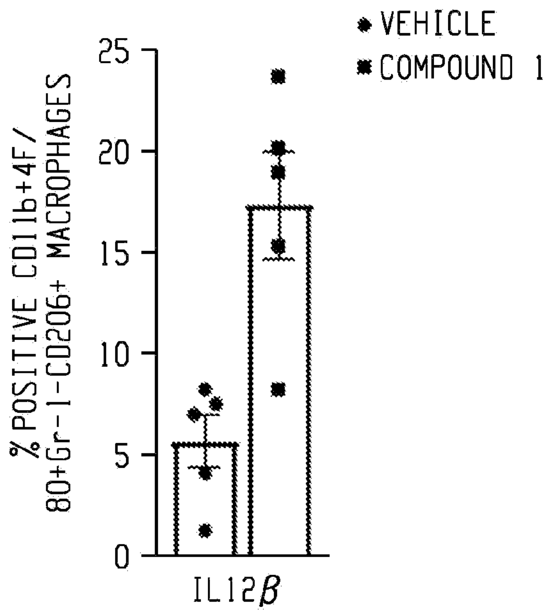
Figure 18G:
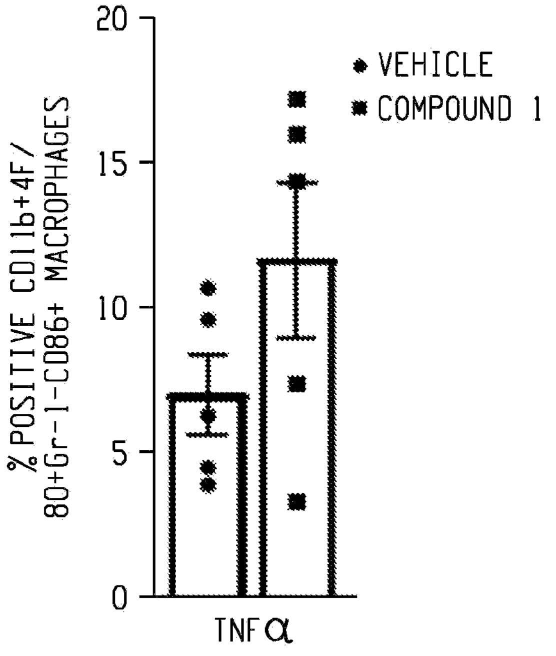
Figure 18H:
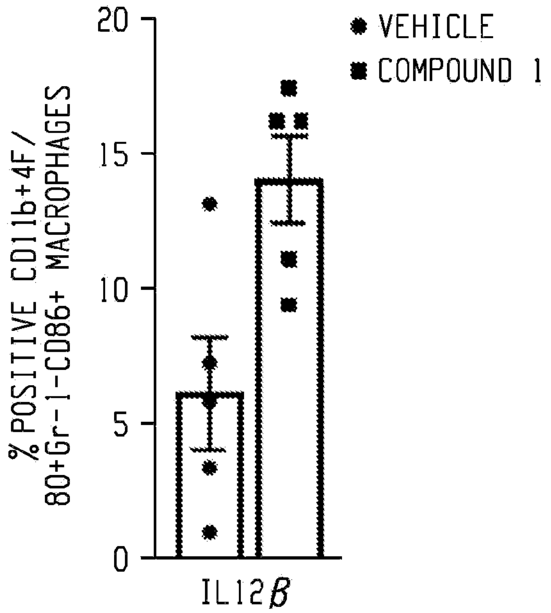
Figure 18I:
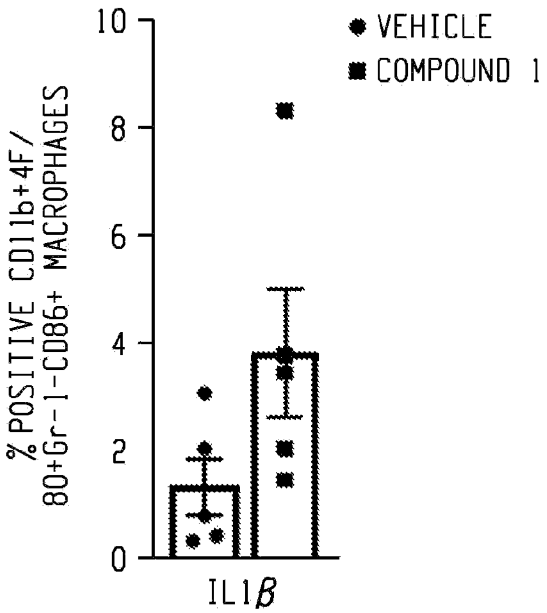

As shown in FIGS. 18A to 18C flow cytometry analysis of KPC tumors treated with Compound 1 compared to vehicle demonstrate that the treatment with Compound 1 showed reduction of CD206 macrophages, shift from $CD206^{high}$ M2 to CD86-positive M1 macrophages, and increase in intratumoral CD8 cells;

As shown in FIGS. 18D to 18I when cytokine and immune checkpoint profile after treatment with Compound 1 for two week in KPC mice was compared with vehicle it showed that Compound 1 selectively infiltrated tumors with M2 macrophages compared to M1 macrophages.

EXAMPLES

Abbreviations

ACN Acetonitrile
AcOH Acetic acid
DCM Dichloromethane
DCE 1,2-dichloroethane
DIPEA Diisopropylethylamine
DMF Dimethylformamide
DMSO Dimethyl Sulfoxide
EDC Ethylene dichloride
EtOAc Ethyl Acetate
EtOH Ethanol
ESI Electrospray Ionization
HATU Hexafluorophosphate Azabenzotriazole Tetramethyl Uronium
HEX/Hex Hexanes
HOBt 1-Hydroxybenzotriazole
HPLC High Performance Liquid Chromatography
LCMS Liquid Chromatography/Mass Spectrometry
MHz Megahertz
μL microliters
mL milliliters
mg milligrams
mmol millimoles
NMR Nuclear Magnetic Resonance
TLC Thin Layer Chromatography General Methods All air or moisture sensitive reactions were performed under positive pressure of nitrogen with oven-dried glassware. Anhydrous solvents such as dichloromethane, N,N-dimethylformamide (DMF), acetonitrile (ACN), methanol (MeOH) and triethylamine ($Et_3N$) were purchased from Sigma-Aldrich (St. Louis, MO). Preparative purification was performed on a Waters semi-preparative HPLC system (Waters Corp., Milford, MA). The column used was a Phenomenex Luna C18 (5 micron, 30×75 mm; Phenomenex, Inc., Torrance, CA) at a flow rate of 45.0 m/min. The mobile phase consisted of acetonitrile and water (each containing 0.1% trifluoroacetic acid). A gradient of 10% to 50% acetonitrile over 8 min was used during the purification. Fraction collection was triggered by UV detection at 220 nm. Analytical analysis was performed on an Agilent LCMS (Agilent Technologies, Santa Clara, CA). Method 1: A 7-min gradient of 4% to 100% acetonitrile (containing 0.025% trifluoroacetic acid) in water (containing 0.05% trifluoroacetic acid) was used with an 8-min run time at a flow rate of 1.0 m/min. Method 2: A 3-min gradient of 4% to 100% acetonitrile (containing 0.025% trifluoroacetic acid) in water (containing 0.05% trifluoroacetic acid) was used with a 4.5-min run time at a flow rate of 1.0 m/min. A Phenomenex Luna C18 column (3 micron, 3×75 mm) was used at a temperature of 50° C. Purity determination was performed using an Agilent diode array detector for both Method 1 and Method 2. Mass determination was performed using an Agilent 6130 mass spectrometer with electrospray ionization in the positive mode. $^1$H NMR spectra were recorded on Varian 400 MHz spectrometers (Agilent Technologies, Santa Clara, CA). Chemical shifts are reported in ppm with undeuterated solvent (DMSO at 2.50 ppm, $CHCl_3$ at 7.26 ppm) as internal standard for DMSO-d6 and $CDCl_3$ solutions respectively. All of the analogs tested in the biological assays have a purity of greater than 95% based on both analytical methods. High resolution mass spectrometry was recorded on Agilent 6210 Time-of-Flight (TOF) LCMS system. Confirmation of molecular formula was accomplished using electrospray ionization in the positive mode with the Agilent Masshunter software (Version B.02). Starting materials were purchased from Combi-Blocks (San Diego, CA) or Sigma-Aldrich (St. Louis, MO), and were used as received, without further purification.

Example 1

Synthesis of 2-(azidomethyl)-5-chloropyrazine

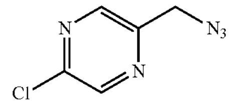

Chemical Formula: $C_5H_4ClN_5$
Exact Mass: 169.02
Molecular Weight: 169.57

Thionyl chloride (505 μL, 6.92 mmol) was added to a solution of (5-chloropyrazin-2-yl)methanol (500 mg, 3.46 mmol) and catalytic DMF in DCM (20.0 mL). The resulting reaction mixture was stirred at room temperature for 1 hour (h), after which LCMS and TLC (20% EtOAc in HEX) analysis showed completion. Reaction mixture was concentrated to dryness, taken up in DCM and concentrated to dryness again. Residue was taken up in DMF (10.0 mL) and potassium carbonate (478 mg, 3.46 mmol) added, followed by sodium azide (270 mg, 4.15 mmol). The resulting reaction mixture was stirred at room temperature for 2 h, after which LC-MS analysis showed completion. Reaction mixture was taken up in $H_2O$, extracted twice with EtOAc, the combined organic layers washed twice with brine, dried over anhydrous $MgSO_4$, filtered and concentrated to afford 2-(azidomethyl)-5-chloropyrazine (587 mg, 3.46 mmol, 100% yield) as a golden oil, which was used without further purification. $^1$H NMR (400 MHz, DMSO-$d_6$) δ 8.84 (d, J=1.4 Hz, 1H), 8.57 (d, J=1.2 Hz, 1H), 4.64 (s, 2H). LCMS retention time (RT) (Method 2)=2.644 min, m/z 170.6 [M+H$^+$].

Example 2

Synthesis of (5-Chloropyrazin-2-yl)methanamine, HCl

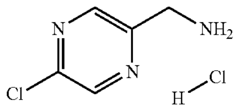

Chemical Formula: $C_5H_7Cl_2N_3$
Exact Mass: 179.00
Molecular Weight: 180.03

To a solution of 2-(azidomethyl)-5-chloropyrazine (587 mg, 3.46 mmol) in MeOH (40.0 mL) was added triphenylphosphine (1.36 grams (g), 5.19 mmol). The resulting reaction mixture was fitted with a condenser and stirred at 80° C. for 1.5 h, after which LCMS and TLC (20% EtOAc in Hex) analysis showed completion. Reaction mixture was concentrated to dryness and residue taken up in toluene (25.0 mL), treated with 4.0 molar (M) HCl in dioxane (2.00 mL, 8.00 mmol), as product precipitated as the HCl salt. The solid was filtered, rinsed with toluene and air dried to afford crude (5-chloropyrazin-2-yl)methanamine, HCl (550 mg, 3.05 mmol, 88% yield) as a tan solid, which was used without further purification. $^1$H NMR (400 MHz, DMSO-$d_6$) δ 8.88 (d, J=1.4 Hz, 1H), 8.68 (d, J=1.4 Hz, 1H), 8.65 (s, 3H), 4.26 (s, 2H).

Example 3

Synthesis of Methyl 4-(((5-chloropyrazin-2-yl)methyl)carbamoyl)benzoate

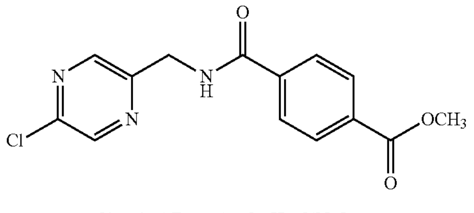

Chemical Formula: $C_{14}H_{12}ClN_3O_3$
Exact Mass: 305.06
Molecular Weight: 305.72

A mixture of 4-(methoxycarbonyl)benzoic acid (605 mg, 3.36 mmol) and HATU (1394 mg, 3.67 mmol) in DMF (10.0 mL) was stirred for 10 minutes (min). (5-Chloropyrazin-2-yl)methanamine, HCl (550 mg, 3.05 mmol) was added and the mixture allowed to stir for 5 min, after which was added DIPEA (1.87 mL, 10.7 mmol) and the resulting reaction mixture stirred overnight, after which LCMS analysis showed completion. Reaction mixture was diluted with $H_2O$ and extracted twice with EtOAc. The combined organic layers where washed twice with brine, dried over anhydrous $MgSO_4$, filtered and concentrated. Residue was purified by flash column chromatography: silica gel with a gradient of 20-60% EtOAc in Hex to afford methyl 4-(((5-chloropyrazin-2-yl)methyl)carbamoyl)benzoate (897 mg, 2.93 mmol, 96% yield) as an off-white solid. $^1$H NMR (400 MHz, DMSO-$d_6$) δ 9.37 (t, J=5.7 Hz, 1H), 8.75 (d, J=1.4 Hz, 1H), 8.53 (d, J=1.4 Hz, 1H), 8.07-8.04 (m, 2H), 8.03-7.99 (m, 2H), 4.63 (d, J=5.7 Hz, 2H), 3.88 (s, 3H). LCMS RT (Method 2)=2.886 min, m/z 635.6 [2M+Na$^+$].

Example 4

Synthesis of Methyl 4-(6-chloroimidazo[1,5-a]pyrazin-3-yl)benzoate

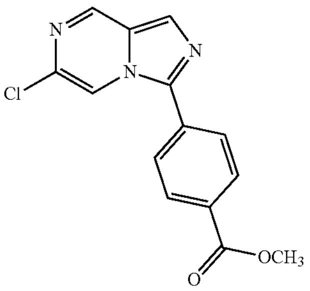

Chemical Formula: $C_{14}H_{10}ClN_3O_2$
Exact Mass: 287.05
Molecular Weight: 287.70

A 1 molar (M) in DCM solution of triflicanhydride (3.52 mL, 3.52 mmol) was added slowly to a solution of methyl 4-(((5-chloropyrazin-2-yl)methyl)carbamoyl)benzoate (897 mg, 2.93 mmol) and 2-methoxypyridine (339 μL, 3.23 mmol) in DCE (10.0 mL). The resulting reaction mixture was then placed in a 45° C. preheated reaction block and allowed to stir for 2 h, after which LCMS analysis showed completion. Reaction mixture was allowed to cool to room temperature and quenched by addition of saturated sodium carbonate solution, stirred for 5 min, diluted with DCM and $H_2O$, the layers separated and the organic phase washed with brine, dried over anhydrous $MgSO_4$, filtered and concentrated. Residue was triturated in EtOH with 10% hexanes, filtered, rinsed with hexanes and allowed to air dry to afford methyl 4-(6-chloroimidazo[1,5-a]pyrazin-3-yl)benzoate (671 mg, 2.33 mmol, 79% yield) as a light tan-colored solid, which was used without further purification. $^1$H NMR (400 MHz, DMSO-$d_6$) δ 9.10 (d, J=1.4 Hz, 1H), 8.66 (t, J=1.2 Hz, 1H), 8.17 (d, J=1.0 Hz, 1H), 8.14 (d, J=8.8 Hz, 2H), 8.11 (d, J=8.9 Hz, 2H), 3.91 (s, 3H). LCMS RT (Method 2)=3.071 min, m/z 287.8 [M$^+$].

Example 5

Synthesis of 4-(6-(3-Fluorophenyl)imidazo[1,5-a]pyrazin-3-yl)benzoic acid

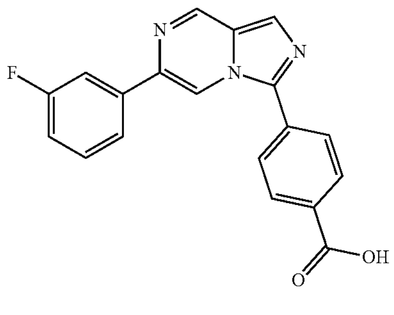

Chemical Formula: $C_{19}H_{12}FN_3O_2$
Exact Mass: 333.09
Molecular Weight: 333.32

A mixture of methyl 4-(6-chloroimidazo[1,5-a]pyrazin-3-yl)benzoate (100 mg, 0.348 mmol), (3-fluorophenyl)boronic acid (58.4 mg, 0.417 mmol), XPhosPd(crotyl)Cl (11.71 mg, 0.017 mmol) and $K_3PO_4$ (148 mg, 0.695 mmol) was placed in a vial and purged with $N_2$ for 2 min. 4:1 dioxane-$H_2O$ (2.50 mL) was added and degassing continued for 2 min, after which the reaction vessel was placed in a preheated block at 90° C. After stirring for 30 min at 90° C. LCMS analysis showed completion. Reaction mixture was allowed to cool to room temperature diluted with EtOAc and $H_2O$, filtered through celite and the layers separated. The organic phase was washed with brine, dried over anhydrous $MgSO_4$, filtered and concentrated. Residue was triturated in EtOH with 10% hexanes, filtered, rinsed with hexanes and allowed to air dry to afford the intermediate methyl ester compound, which was taken up in 1:1 EtOH-THF (5.00 mL) and treated with 2M sodium hydroxide (2.00 mL, 4.00 mmol). The resulting reaction mixture was stirred at room temperature for 2 h, after which LCMS analysis showed completion. Reaction mixture was concentrated to a slurry, residue taken up in $H_2O$ and the pH adjusted with AcOH to ~5 as product precipitated. Product was then collected by filtration, rinsed generously with $H_2O$ and allowed to air dry to afford 4-(6-(3-fluorophenyl)imidazo[1,5-a]pyrazin-3-yl)benzoic acid (96.0 mg, 0.289 mmol, 83% yield) as an off-white solid, which was used without further purification. $^1H$ NMR (400 MHz, DMSO-$d_6$) δ 13.15 (s, 1H), 9.30 (d, J=1.6 Hz, 1H), 8.89-8.84 (m, 1H), 8.15 (s, 4H), 8.10 (d, J=0.9 Hz, 1H), 7.98-7.90 (m, 2H), 7.53 (td, J=8.2, 6.3 Hz, 1H), 7.30-7.20 (m, 1H). $^{19}F$ NMR (376 MHz, DMSO-$d_6$) δ −112.98 (td, J=9.9, 6.3 Hz). LCMS RT (Method 2)=3.144 min, m/z 334.8 [M+H$^+$].

Example 6

Synthesis of 4-(6-Chloroimidazo[1,5-a]pyrazin-3-yl)-N-(3-(2-oxopyrrolidin-1-yl)propyl)benzamide

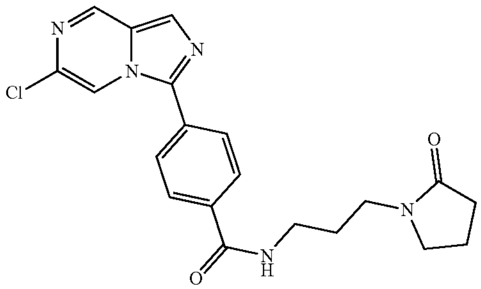

Chemical Formula: $C_{20}H_{20}ClN_5O_2$
Exact Mass: 397.13
Molecular Weight: 397.86

A solution of LiOH (125 mg, 5.21 mmol) in $H_2O$ (1.00 mL) was added to a solution of methyl 4-(6-chloroimidazo[1,5-a]pyrazin-3-yl)benzoate (300 mg, 1.043 mmol) in THF (4.00 mL). The resulting reaction mixture was stirred at room temperature for 1 h, after which LCMS analysis showed completion. Reaction mixture was concentrated to a slurry, residue taken up in $H_2O$ and the pH adjusted with AcOH to ~5 as product precipitated. Product was then collected by filtration, rinsed generously with $H_2O$ and allowed to air dry to afford the intermediate acid, which was used without further purification.

A mixture of the intermediate 4-(6-chloroimidazo[1,5-a]pyrazin-3-yl)benzoic acid (203 mg, 0.742 mmol) and HATU (310 mg, 0.816 mmol) in DMF (5.00 mL) were stirred for 10 min, after which was added 1-(3-aminopropyl)pyrrolidin-2-one (105 mg, 0.742 mmol). The resulting reaction mixture was stirred for 20 min, after which was added DIPEA (259 μL, 1.48 mmol) and the reaction stirred for 2 h, after which LCMS analysis showed completion. Reaction mixture was diluted with EtOAc, washed with $H_2O$ and brine, dried over anhydrous $MgSO_4$, filtered and concentrated. Residue was purified by flash column chromatography: silica gel with a gradient of 0-30% MeOH in EtOAc to afford 4-(6-chloro-imidazo[1,5-a]pyrazin-3-yl)-N-(3-(2-oxopyrrolidin-1-yl)propyl)benzamide (207 mg, 0.520 mmol, 70.1% yield) as an off-white solid. $^1H$ NMR (400 MHz, Chloroform-d) δ 8.87 (d, J=1.4 Hz, 1H), 8.21 (t, J=1.2 Hz, 1H), 8.17 (d, J=8.4 Hz, 2H), 8.08 (s, 1H), 8.01 (d, J=1.0 Hz, 1H), 7.91 (d, J=8.4 Hz, 2H), 3.49-3.44 (m, 6H), 2.50 (t, J=8.1 Hz, 2H), 2.17-2.07 (m, 2H), 1.86-1.77 (m, 2H). LCMS RT (Method 2)=2.772 min, m/z 398.8 [M+H$^+$].

Example 7

Synthesis of N-(3-(2-Oxopyrrolidin-1-yl)propyl)-4-(6-(pyridin-3-yl)imidazo[1,5-a]pyrazin-3-yl)benzamide (Compound 26)

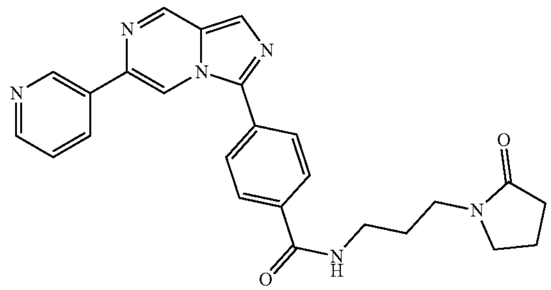

Chemical Formula: $C_{25}H_{24}N_6O_2$
Exact Mass: 440.20
Molecular Weight: 440.51

A mixture of 4-(6-chloroimidazo[1,5-a]pyrazin-3-yl)-N-(3-(2-oxopyrrolidin-1-yl)propyl)benzamide (10.0 mg, 0.025 mmol), pyridin-3-ylboronic acid (3.71 mg, 0.030 mmol), XPhosPd(crotyl)Cl (0.847 mg, 1.26 μmol) and $K_3PO_4$ (10.7 mg, 0.050 mmol) were placed in a vial and purged with $N_2$ for 2 min. 4:1 Dioxane-$H_2O$ (2.50 mL) was added and degassing continued for 2 min, after which reaction vessel was placed in a preheated block at 90° C. After stirring for 30 min at 90° C., LCMS analysis showed completion. Reaction mixture was allowed to cool to room temperature and loaded directly to a silica gel column and purified by flash column chromatography: silica gel with a gradient of 5-50% MeOH in EtOAc to afford N-(3-(2-oxopyrrolidin-1-yl)propyl)-4-(6-(pyridin-3-yl)imidazo[1,5-a]pyrazin-3-yl) benzamide (9.3 mg, 0.021 mmol, 84% yield) as an off-white crystalline solid. $^1H$ NMR (400 MHz, Chloroform-d) δ 9.14 (d, J=1.6 Hz, 1H), 9.13 (dd, J=2.4, 0.9 Hz, 1H), 8.66 (dd, J=4.8, 1.6 Hz, 1H), 8.50 (dd, J=1.6, 1.0 Hz, 1H), 8.23 (ddd, J=8.0, 2.4, 1.7 Hz, 1H), 8.20-8.16 (m, 2H), 8.08 (t, J=6.3 Hz, 1H), 8.00 (d, J=0.9 Hz, 1H), 7.98-7.93 (m, 2H), 7.42 (ddd, J=8.0, 4.8, 0.9 Hz, 1H), 3.46 (tt, J=7.4, 2.7 Hz, 6H), 2.49 (dd, J=8.7, 7.6 Hz, 2H), 2.17-2.06 (m, 2H), 1.87-1.77 (m, 2H). LCMS RT (Method 1)=3.232 min, m/z 441.9 [M+H$^+$].

Example 8

Synthesis of N-(3-(2-Oxopyrrolidin-1-yl)propyl)-4-(6-(3-(trifluoromethyl)phenyl)imidazo[1,5-a]pyrazin-3-yl)benzamide (Compound 27)

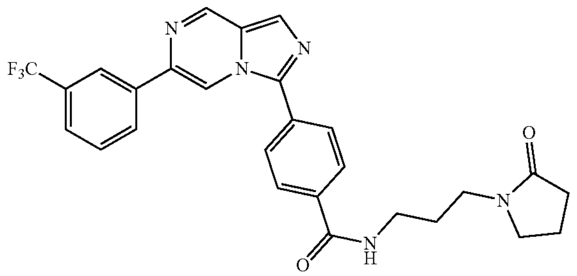

Chemical Formula: $C_{27}H_{24}F_3N_5O_2$
Exact Mass: 507.19
Molecular Weight: 507.52

A mixture of 4-(6-chloroimidazo[1,5-a]pyrazin-3-yl)-N-(3-(2-oxopyrrolidin-1-yl)propyl)benzamide (10.0 mg, 0.025 mmol), (3-(trifluoromethyl)phenyl)boronic acid (5.73 mg, 0.030 mmol), XPhosPd(crotyl)Cl (0.847 mg, 1.26 μmol) and $K_3PO_4$ (10.7 mg, 0.050 mmol) were placed in a vial and purged with $N_2$ for 2 min. 4:1 dioxane-$H_2O$ (2.50 mL) was added and degassing continued for 2 min, after which reaction vessel was placed in a preheated block at 90° C. After stirring for 30 min at 90° C., LCMS analysis showed completion. Reaction mixture was allowed to cool to room temperature and loaded directly to a silica gel column and purified by flash column chromatography: silica gel with a gradient of 0-30% MeOH in EtOAc to afford N-(3-(2-oxopyrrolidin-1-yl)propyl)-4-(6-(3-(trifluoromethyl)phenyl)imidazo[1,5-a]pyrazin-3-yl)benzamide (10.2 mg, 0.020 mmol, 80% yield) as an off-white crystalline solid. $^1H$ NMR (400 MHz, Chloroform-d) δ 9.14 (d, J=1.6 Hz, 1H), 8.50 (dd, J=1.7, 1.0 Hz, 1H), 8.23 (dd, J=2.0, 1.1 Hz, 1H), 8.21-8.17 (m, 2H), 8.10-8.02 (m, 2H), 7.99 (d, J=0.9 Hz, 1H), 7.98-7.94 (m, 2H), 7.70-7.65 (m, 1H), 7.59 (dt, J=7.8, 0.7 Hz, 1H), 3.46 (tt, J=7.5, 2.7 Hz, 6H), 2.53-2.44 (m, 2H), 2.17-2.06 (m, 2H), 1.83 (qd, J=7.7, 6.9, 5.1 Hz, 2H). $^{19}F$ NMR (376 MHz, $CDCl_3$) δ −62.60 (s, 3F). LCMS RT (Method 1)=5.058 min, m/z 508.8 [M+H$^+$].

Example 9

Synthesis of N-(2-Morpholinoethyl)-4-(6-phenylimidazo[1,5-a]pyrazin-3-yl)benzamide (Compound 4)

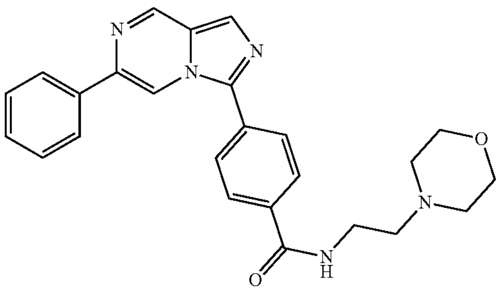

Chemical Formula: $C_{25}H_{25}N_5O_2$
Exact Mass: 427.20
Molecular Weight: 427.51

A mixture of 4-(6-phenylimidazo[1,5-a]pyrazin-3-yl)benzoic acid (50.0 mg, 0.159 mmol) and HATU (72.3 mg, 0.190 mmol) in DMF (2.00 mL) were stirred for 10 min, after which was added 2-morpholinoethan-1-amine (22.7 mg, 0.174 mmol). The resulting reaction mixture was stirred for 20 min, after which was added DIPEA (69.2 μL, 0.396 mmol) and the reaction stirred overnight, after which LCMS analysis showed completion. Reaction mixture was diluted with EtOAc, washed with $H_2O$ and brine, dried over anhydrous $MgSO_4$, filtered and concentrated. Residue was triturated in EtOH, filtered and air dried to afford N-(2-morpholinoethyl)-4-(6-phenylimidazo[1,5-a]pyrazin-3-yl) benzamide (49.3 mg, 0.115 mmol, 72.7% yield) as a light golden solid. $^1H$ NMR (400 MHz, Chloroform-d) δ 9.14 (d, J=1.6 Hz, 1H), 8.47 (dd, J=1.6, 1.0 Hz, 1H), 8.03-7.92 (m, 5H), 7.92-7.85 (m, 2H), 7.52-7.46 (m, 2H), 7.45-7.40 (m, 1H), 6.87 (s, 1H), 3.79-3.72 (m, 4H), 3.66-3.57 (m, 2H), 2.65 (t, J=6.0 Hz, 2H), 2.54 (t, J=4.6 Hz, 4H). LCMS RT (Method 1)=3.645 min, m/z 428.1 [M+H$^+$].

Figure 4:
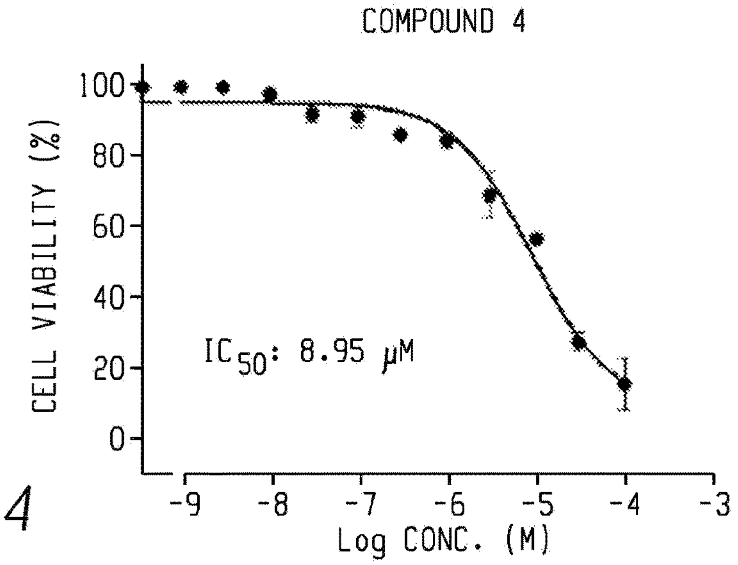
FIG. 4 shows a graph of Percentage Relative Cell Viability versus Log Molar Concentration illustrating macrophage activity of Compound 4 with IC50 of 8.95 micromolar (μM)

FIG. 4 shows IC50 of 8.95 μM for Compound 4.

Example 10

Synthesis of N-(2-Acetamidoethyl)-4-(6-phenylimidazo[1,5-a]pyrazin-3-yl)benzamide (Compound 14)

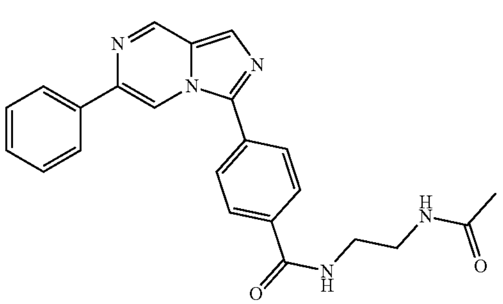

Chemical Formula: $C_{23}H_{21}N_5O_2$
Exact Mass: 399.17
Molecular Weight: 399.45

A mixture of 4-(6-phenylimidazo[1,5-a]pyrazin-3-yl)benzoic acid (50.0 mg, 0.159 mmol) and HATU (72.3 mg, 0.190 mmol) in DMF (2.00 mL) were stirred for 10 min, after which was added N-(2-aminoethyl)acetamide (17.8 mg, 0.174 mmol). The resulting reaction mixture was stirred for 20 min, after which was added DIPEA (69.2 μL, 0.396 mmol) and the reaction stirred overnight, after which LCMS analysis showed completion. Reaction mixture was diluted with EtOAc, washed with $H_2O$ and brine, dried over anhydrous $MgSO_4$, filtered and concentrated. Residue was purified by flash column chromatography: silica gel with a gradient of 0-20% MeOH in EtOAc to afford N-(2-acetamidoethyl)-4-(6-phenylimidazo[1,5-a]pyrazin-3-yl)benzamide (41.3 mg, 0.103 mmol, 65.2% yield) as an off-white solid. $^1H$ NMR (400 MHz, DMSO-$d_6$) δ 9.29 (d, J=1.5 Hz, 1H), 8.74 (dd, J=1.6, 1.0 Hz, 1H), 8.67 (t, J=5.6 Hz, 1H), 8.15-8.03 (m, 7H), 8.00 (t, J=5.9 Hz, 1H), 7.54-7.46 (m, 2H), 7.46-7.38 (m, 1H), 3.40-3.28 (m, 2H), 3.28-3.19 (m, 2H), 1.83 (s, 3H). LCMS RT (Method 1)=3.515 min, m/z 400.1 [M+$H^+$].

Example 11

Synthesis of (1,1-Dioxidothiomorpholino)(4-(6-phenylimidazo[1,5-a]pyrazin-3-yl)phenyl)methanone (Compound 15)

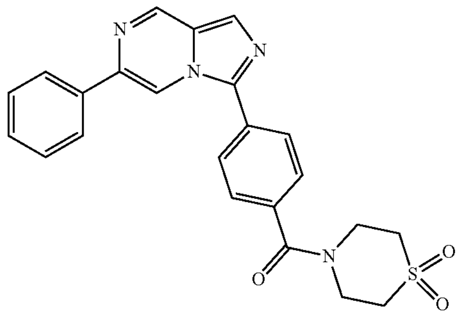

Chemical Formula: $C_{23}H_{20}N_4O_3S$
Exact Mass: 432.13
Molecular Weight: 432.50

A mixture of 4-(6-phenylimidazo[1,5-a]pyrazin-3-yl)benzoic acid (50.0 mg, 0.159 mmol) and HATU (72.3 mg, 0.190 mmol) in DMF (2.00 mL) were stirred for 10 min, after which was added thiomorpholine 1,1-dioxide (21.4 mg, 0.159 mmol). The resulting reaction mixture was stirred for 20 min, after which was added DIPEA (69.2 μL, 0.396 mmol) and the reaction stirred overnight, after which LCMS analysis showed completion. Reaction mixture was diluted with EtOAc, washed with $H_2O$ and brine, dried over anhydrous $MgSO_4$, filtered and concentrated. Residue was triturated in EtOH, filtered and air dried to afford (1,1-dioxidothiomorpholino)(4-(6-phenylimidazo[1,5-a]pyrazin-3-yl)phenyl)methanone (54.6 mg, 0.126 mmol, 80% yield) as a light golden solid. $^1H$ NMR (400 MHz, Chloroform-d) δ 9.15 (d, J=1.6 Hz, 1H), 8.44 (dd, J=1.6, 1.0 Hz, 1H), 8.01-7.96 (m, 3H), 7.92-7.86 (m, 2H), 7.69-7.64 (m, 2H), 7.53-7.47 (m, 2H), 7.46-7.41 (m, 1H), 4.16 (s, 4H), 3.11 (s, 4H). LCMS RT (Method 1)=3.845 min, m/z 433.1 [M+$H^+$].

Example 12

Synthesis of N-(3-Hydroxypropyl)-4-(6-phenylimidazo[1,5-a]pyrazin-3-yl)benzamide (Compound 16)

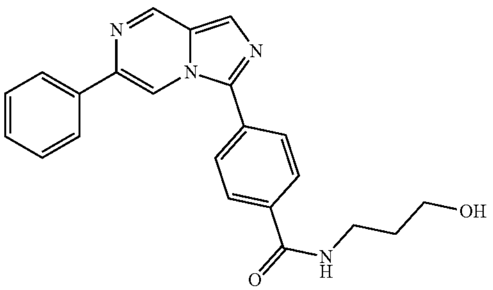

Chemical Formula: $C_{22}H_{20}N_4O_2$
Exact Mass: 372.16
Molecular Weight: 372.43

A mixture of 4-(6-phenylimidazo[1,5-a]pyrazin-3-yl)benzoic acid (50.0 mg, 0.159 mmol) and HATU (72.3 mg, 0.190 mmol) in DMF (2.00 mL) were stirred for 10 min, after which was added 3-aminopropan-1-ol (13.1 mg, 0.174 mmol). The resulting reaction mixture was stirred for 20 min, after which was added DIPEA (69.2 μL, 0.396 mmol) and the reaction stirred overnight, after which LCMS analysis showed completion. Reaction mixture was diluted with EtOAc, washed with $H_2O$ and brine, dried over anhydrous $MgSO_4$, filtered and concentrated. Residue was purified by flash column chromatography: silica gel with a gradient of 0-20% MeOH in EtOAc to afford N-(3-hydroxypropyl)-4-(6-phenylimidazo[1,5-a]pyrazin-3-yl)benzamide (41.3 mg, 0.111 mmol, 69.9% yield) as an off-white foam. $^1H$ NMR (400 MHz, DMSO-$d_6$) δ 9.29 (d, J=1.5 Hz, 1H), 8.74 (dd, J=1.6, 1.0 Hz, 1H), 8.60 (t, J=5.6 Hz, 1H), 8.15-8.00 (m, 7H), 7.54-7.45 (m, 2H), 7.45-7.38 (m, 1H), 4.49 (t, J=5.2 Hz, 1H), 3.49 (td, J=6.3, 5.2 Hz, 2H), 3.36 (q, J=6.6 Hz, 2H), 1.71 (dq, J=7.6, 6.4 Hz, 2H). LCMS RT (Method 1)=3.920 min, m/z 373.1 [M+$H^+$].

Example 13

Synthesis of 4-(6-Phenylimidazo[1,5-a]pyrazin-3-yl) benzamide

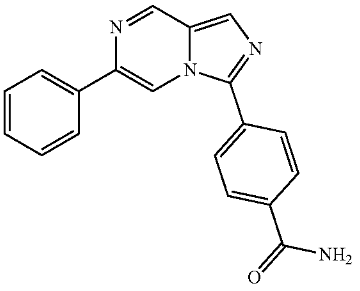

Chemical Formula: $C_{19}H_{14}N_4O$
Exact Mass: 314.12
Molecular Weight: 314.35

A mixture of 4-(6-phenylimidazo[1,5-a]pyrazin-3-yl)benzoic acid (50.0 mg, 0.159 mmol) and HATU (72.3 mg, 0.190 mmol) in DMF (2.00 mL) were stirred for 10 min, after which was added 7 Normal (N) ammonia in MeOH (0.200 mL, 1.40 mmol). The resulting reaction mixture was stirred for 20 min, after which was added DIPEA (0.069 mL, 0.396 mmol) and the reaction stirred overnight, after which LCMS analysis showed completion. Reaction mixture was diluted with EtOAc, washed with $H_2O$ and brine, dried over anhydrous $MgSO_4$, filtered and concentrated. Residue was triturated in EtOH, filtered and air dried to afford 4-(6-phenylimidazo[1,5-a]pyrazin-3-yl)benzamide (25.0 mg, 0.080 mmol, 50.2% yield) as a light yellow-golden solid. $^1$H NMR (400 MHz, DMSO-$d_6$) δ 9.29 (d, J=1.5 Hz, 1H), 8.75 (dd, J=1.6, 0.9 Hz, 1H), 8.15-8.03 (m, 8H), 7.49 (tq, J=6.2, 1.4 Hz, 3H), 7.45-7.39 (m, 1H). LCMS RT (Method 1)=4.038 min, m/z 651.7 [2M+Na$^+$], 315.9 [M+H$^+$].

Example 14

Synthesis of 2-Chloro-5-hydrazinylpyrazine

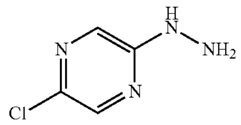

Chemical Formula: $C_4H_5ClN_4$
Exact Mass: 144.02
Molecular Weight: 144.56

Hydrazine (0.211 ml, 6.71 mmol) was added to a solution of 2,5-dichloropyrazine (1.00 g, 6.71 mmol) in EtOH (20.0 mL). The resulting reaction mixture was stirred at 80° C. for 2 h, after which LC-MS analysis showed completion. Reaction mixture was allowed to cool to room temperature and product precipitated. Mixture was poured over ice $H_2O$, stirred vigorously for 5 min, filtered, rinsed with $H_2O$ and allowed to air dry to afford 2-chloro-5-hydrazinylpyrazine (885 mg, 6.12 mmol, 91% yield) as a white powder, which was used without further purification. $^1$H NMR (400 MHz, DMSO-$d_6$) δ 8.16 (s, 1H), 8.04 (s, 1H), 7.93 (s, 1H), 4.32 (s, 2H).

Example 15

Synthesis of Methyl 4-(2-(5-chloropyrazin-2-yl) hydrazine-1-carbonyl)benzoate

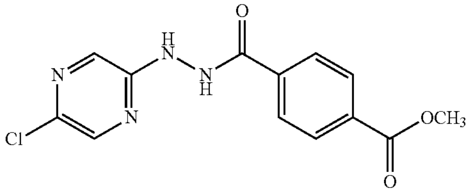

Chemical Formula: $C_{13}H_{11}ClN_4O_3$
Exact Mass: 306.05
Molecular Weight: 306.71

To a solution of 2-chloro-5-hydrazinylpyrazine (260 mg, 1.80 mmol), 4-(methoxycarbonyl)benzoic acid (405 mg, 2.25 mmol) and DIPEA (0.942 mL, 5.40 mmol) in DMF (5.00 mL) was added a 50% solution of propylphosphonic anhydride (T3P) in DMF (1.58 mL, 2.70 mmol). The resulting reaction mixture was allowed to stir at room temperature for 1 h, after which LC-MS analysis showed completion. Reaction mixture was poured over ice $H_2O$, stirred for 10 min, product collected by filtration, rinsed generously with $H_2O$ and allowed to air dry to afford methyl 4-(2-(5-chloropyrazin-2-yl)hydrazine-1-carbonyl)benzoate as a light yellow solid, which was used without further purification. $^1$H NMR (400 MHz, DMSO-$d_6$) δ 10.75 (s, 1H), 9.33 (s, 1H), 8.21 (d, J=1.4 Hz, 1H), 8.12-8.06 (m, 2H), 8.06-7.99 (m, 2H), 7.94 (d, J=1.4 Hz, 1H), 3.90 (s, 3H). LCMS RT (Method 2)=2.784 min, m/z 306.8 [M$^+$].

Example 16

Synthesis of Methyl 4-(6-chloro-[1,2,4]triazolo[4,3-a]pyrazin-3-yl)benzoate

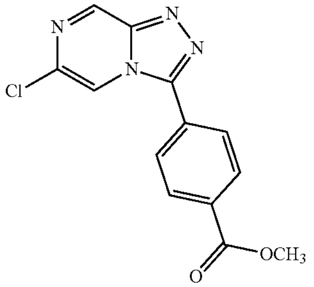

Chemical Formula: $C_{13}H_9ClN_4O_2$
Exact Mass: 288.04
Molecular Weight: 288.69

Perchloroethane (232 mg, 0.978 mmol) was added to a suspension of methyl 4-(2-(5-chloropyrazin-2-yl)hydrazine-1-carbonyl)benzoate (150 mg, 0.489 mmol), triphenylphosphine (257 mg, 0.978 mmol) and DIPEA (0.342 mL, 1.96 mmol) in ACN (5.00 mL) with 4 Å molecular sieves (MS). The resulting reaction mixture was stirred at 80° C. for 2 h, after which LCMS analysis showed completion. Reaction mixture was cooled to room temperature, filtered through celite and the filter cake rinsed generously with EtOAc. The filtrated was concentrated under reduced pressure and residue purified by flash column chromatography: silica gel with a gradient of 20-60% EtOAc in Hex to afford methyl 4-(6-chloro-[1,2,4]triazolo[4,3-a]pyrazin-3-yl)benzoate (105 mg, 0.364 mmol, 74.4% yield). $^1$H NMR (400 MHz, DMSO-$d_6$) δ 9.46 (d, J=1.5 Hz, 1H), 8.94 (d, J=1.5 Hz, 1H), 8.19 (d, J=2.5 Hz, 2H), 8.17 (d, J=2.7 Hz, 2H), 3.93 (s, 3H). LCMS RT (Method 2)=2.972 min, m/z 600.6 [2M+Na$^+$], 289.9 [M$^+$].

Example 17

Synthesis of Methyl 4-(6-phenyl-[1,2,4]triazolo[4,3-a]pyrazin-3-yl)benzoate

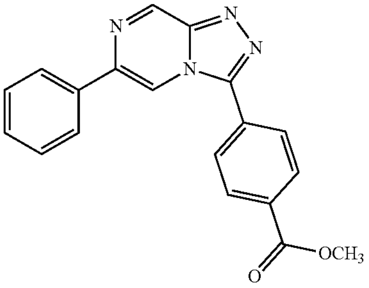

Chemical Formula: $C_{19}H_{14}N_4O_2$
Exact Mass: 330.11
Molecular Weight: 330.35

A mixture of methyl 4-(6-chloro-[1,2,4]triazolo[4,3-a]pyrazin-3-yl)benzoate (40.0 mg, 0.139 mmol), phenylboronic acid (21.1 mg, 0.173 mmol), XPhosPd(crotyl)Cl (4.67 mg, 6.93 μmol) and $K_3PO_4$ (58.8 mg, 0.277 mmol) were placed in a vial and purged with $N_2$ for 2 min. 4:1 Dioxane: $H_2O$ (2.50 mL) was added and degassing continued for 2 min, after which reaction vessel was placed in a preheated block at 100° C. After stirring for 30 min at 100° C. LCMS analysis showed completion. Reaction mixture was allowed to cool to room temperature, partitioned between brine and EtOAc, filtered through celite and the layers separated. The organic phase was washed with brined, dried over anhydrous $MgSO_4$, filtered and concentrated to afford crude methyl 4-(6-phenyl-[1,2,4]triazolo[4,3-a]pyrazin-3-yl)benzoate (38.0 mg, 0.115 mmol, 83% yield), which was used without further purification. LCMS RT (Method 2)=3.319 min, m/z 683.7 [2M+Na$^+$].

Example 18

Synthesis of 4-(6-Phenyl-[1,2,4]triazolo[4,3-a]pyrazin-3-yl)benzoic acid

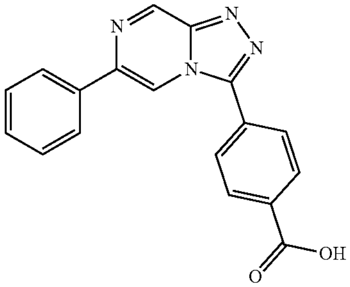

Chemical Formula: $C_{18}H_{12}N_4O_2$
Exact Mass: 316.10
Molecular Weight: 316.32

2M sodium hydroxide (1.00 mL, 2.00 mmol) was added to a solution of methyl 4-(6-phenyl-[1,2,4]triazolo[4,3-a]pyrazin-3-yl)benzoate (46.0 mg, 0.139 mmol) in EtOH (5.00 mL). The resulting reaction mixture was stirred at room temperature for 1 h, after which LCMS analysis showed completion. Reaction mixture was concentrated to a slurry and residue partitioned between 1M HCl and EtOAc, the layers separated and the organic phase washed with brine, dried over anhydrous $MgSO_4$, filtered and concentrated to afford crude 4-(6-phenyl-[1,2,4]triazolo[4,3-a]pyrazin-3-yl)benzoic acid (44.0 mg, 0.139 mmol, 100% yield), which was used without further purification. LCMS RT (Method 2)=2.893 min, m/z 317.0 [M+H$^+$].

Example 19

Synthesis of N-(3-(2-Oxopyrrolidin-1-yl)propyl)-4-(6-phenyl-[1,2,4]triazolo[4,3-a]pyrazin-3-yl)benzamide (Compound 30)

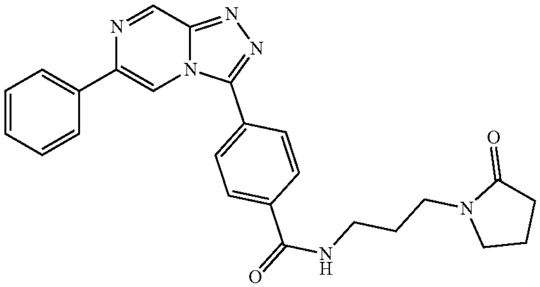

Chemical Formula: $C_{25}H_{24}N_6O_2$
Exact Mass: 440.20
Molecular Weight: 440.51

A mixture of 4-(6-phenyl-[1,2,4]triazolo[4,3-a]pyrazin-3-yl)benzoic acid (44.0 mg, 0.139 mmol) and HATU (63.5 mg, 0.167 mmol) in DMF (1.50 mL) were stirred for 10 min, after which was added 1-(3-aminopropyl)pyrrolidin-2-one (21.5 μL, 0.153 mmol). The resulting reaction mixture was stirred for 20 min, after which was added DIPEA (60.7 μL, 0.348 mmol) and the reaction stirred overnight, after which LCMS analysis showed completion. Reaction mixture was diluted with EtOAc, washed with $H_2O$ and brine, dried over anhydrous $MgSO_4$, filtered and concentrated. Residue was purified by flash column chromatography: silica gel with a gradient of 0-20% MeOH in EtOAc to afford N-(3-(2-oxopyrrolidin-1-yl)propyl)-4-(6-phenyl-[1,2,4]triazolo[4,3-a]pyrazin-3-yl)benzamide (24.0 mg, 0.054 mmol, 39.2% yield) as a faint yellow solid. $^1$H NMR (400 MHz, DMSO-$d_6$) δ 9.63 (d, J=1.6 Hz, 1H), 8.92 (d, J=1.6 Hz, 1H), 8.68 (t, J=5.7 Hz, 1H), 8.20-8.15 (m, 2H), 8.14-8.09 (m, 4H), 7.56-7.50 (m, 2H), 7.49-7.43 (m, 1H), 3.37 (t, J=7.1 Hz, 2H), 3.32-3.23 (m, 4H), 2.24 (dd, J=8.3, 7.8 Hz, 2H), 1.98-1.89 (m, 2H), 1.75 (p, J=7.0 Hz, 2H). LCMS RT (Method 1)=4.130 min, m/z 882.3 [2M+H$^+$], 441.1 [M+H$^+$].

Example 20

Synthesis of 5-Bromo-2-hydrazinylpyridine

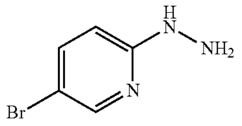

Chemical Formula: $C_5H_6BrN_3$
Exact Mass: 186.97
Molecular Weight: 188.03

A solution of 5-bromo-2-fluoropyridine (1.00 mL, 9.72 mmol) and hydrazine (1.52 mL, 48.6 mmol) in EtOH (10.0 mL) was stirred at 100° C. for 1 h, after which LCMS analysis showed completion. Reaction volume was reduced to half and mixture allowed to cool to room temperature as product precipitated. Slurry was poured into ice $H_2O$ and stirred for 5 min, product was filtered and rinsed with $H_2O$ and allowed to air dry to afford 5-bromo-2-hydrazinylpyridine (1.60 g, 8.51 mmol, 88% yield) as an off-white fluffy off-white solid which was used without further purification. $^1H$ NMR (400 MHz, DMSO-$d_6$) δ 8.02 (dd, J=2.6, 0.7 Hz, 1H), 7.65 (s, 1H), 7.58 (dd, J=8.9, 2.5 Hz, 1H), 6.69 (dd, J=9.0, 0.7 Hz, 1H), 4.15 (s, 2H). LCMS RT (Method 2)=1.150 min, m/z 189.3 [M+$H^+$].

Example 21

Synthesis of Methyl 4-(2-(5-bromopyridin-2-yl) hydrazine-1-carbonyl)benzoate

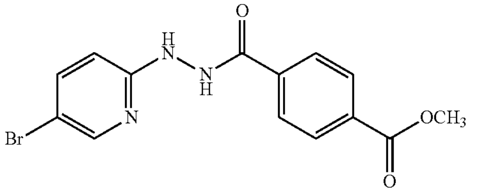

Chemical Formula: $C_{14}H_{12}BrN_3O_3$
Exact Mass: 349.01
Molecular Weight: 350.17

To a solution of 5-bromo-2-hydrazinylpyridine (500 mg, 2.66 mmol), 4-(methoxycarbonyl)benzoic acid (599 mg, 3.32 mmol) and DIPEA (1.39 mL, 7.98 mmol) in DMF (5.00 mL) was added a 50% solution of propylphosphonic anhydride (T3P) in DMF (2.33 mL, 3.99 mmol). The resulting reaction mixture was allowed to stir at room temperature for 1 h, after which LCMS analysis showed completion. Reaction mixture was poured over ice $H_2O$, stirred for 10 min, product collected by filtration, rinsed generously with $H_2O$ and allowed to air dry to afford methyl 4-(2-(5-bromopyridin-2-yl)hydrazine-1-carbonyl)benzoate (906 mg, 2.59 mmol, 97% yield) as a tan solid, which was used without further purification. $^1H$ NMR (400 MHz, DMSO-$d_6$) δ 10.61 (d, J=1.9 Hz, 1H), 8.80 (d, J=1.9 Hz, 1H), 8.15 (dd, J=2.5, 0.7 Hz, 1H), 8.10-8.05 (m, 2H), 8.05-8.00 (m, 2H), 7.71 (dd, J=8.9, 2.5 Hz, 1H), 6.66 (dd, J=8.9, 0.7 Hz, 1H), 3.89 (d, J=2.5 Hz, 3H). LCMS RT (Method 2)=2.863 min, m/z 352.3 [M+$H^+$].

Example 22

Synthesis of Methyl 4-(6-bromo-[1,2,4]triazolo[4,3-a]pyridin-3-yl)benzoate

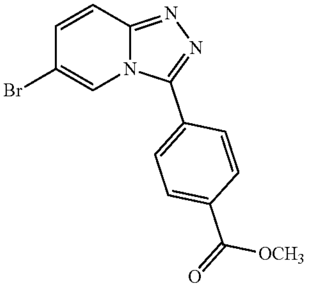

Chemical Formula: $C_{14}H_{10}BrN_3O_2$
Exact Mass: 331.00
Molecular Weight: 332.16

Perchloroethane (946 mg, 4.00 mmol) was added to a suspension of methyl 4-(2-(5-bromopyridin-2-yl)hydrazine-1-carbonyl)benzoate (700 mg, 1.99 mmol), triphenylphosphine (1.05 g, 4.00 mmol) and DIPEA (1.39 mL, 8.00 mmol) in ACN (10.0 mL) with 4 Å MS. The resulting reaction mixture was stirred at 80° C. for 2 h, after which LCMS analysis showed completion. Reaction mixture was cooled to room temperature, filtered through celite and the filter cake rinsed generously with EtOAc. The filtrated was concentrated under reduced pressure and residue purified by flash column chromatography: silica gel with a gradient of 20-80% EtOAc in Hex to afford methyl 4-(6-bromo-[1,2,4]triazolo[4,3-a]pyridin-3-yl)benzoate (604 mg, 1.818 mmol, 91% yield). LCMS RT (Method 2)=3.004 min, m/z 333.7 [M+$H^+$].

Example 23

Synthesis of Methyl 4-(6-phenyl-[1,2,4]triazolo[4,3-a]pyridin-3-yl)benzoate

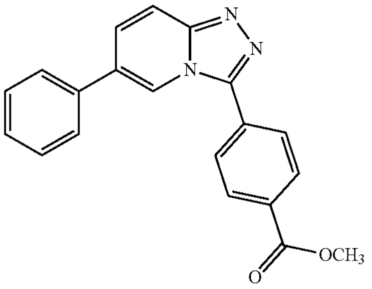

Chemical Formula: $C_{20}H_{15}N_3O_2$
Exact Mass: 329.12
Molecular Weight: 329.36

A mixture of methyl 4-(6-bromo-[1,2,4]triazolo[4,3-a]pyridin-3-yl)benzoate (300 mg, 0.903 mmol), phenylboronic acid (138 mg, 1.13 mmol), XPhos Pd(crotyl)Cl (30.4 mg, 0.045 mmol) and $K_3PO_4$ (383 mg, 1.81 mmol) were placed in a vial and purged with $N_2$ for 2 min. 4:1 Dioxane: $H_2O$ (10.0 mL) was added and degassing continued for 2 min, after which reaction vessel was placed in a preheated block at 100° C. After stirring for 30 min at 100° C. LC-MS analysis showed completion. Reaction mixture was allowed to cool to room temperature, partitioned between brine and EtOAc, filtered through celite and the layers separated. The organic phase was washed with brined, dried over anhydrous $MgSO_4$, filtered and concentrated. Residue was purified by flash column chromatography: silica gel with a gradient of 40-100% EtOAc in Hex to afford methyl 4-(6-phenyl-[1,2,4]triazolo[4,3-a]pyridin-3-yl)benzoate (290 mg, 0.880 mmol, 97% yield) as an off-white solid. LCMS RT (Method 2)=3.156 min, m/z 330.1 [M+H$^+$].

Example 24

Synthesis of 4-(6-Phenyl-[1,2,4]triazolo[4,3-a]pyridin-3-yl)benzoic acid

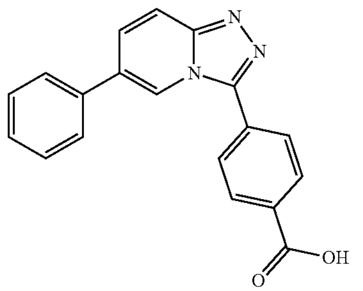

Chemical Formula: $C_{19}H_{13}N_3O_2$
Exact Mass: 315.10
Molecular Weight: 315.33

A suspension of methyl 4-(6-phenyl-[1,2,4]triazolo[4,3-a]pyridin-3-yl)benzoate (290 mg, 0.880 mmol) in EtOH (8.00 mL) was treated with 2M sodium hydroxide (2.00 mL, 4.00 mmol). The resulting reaction mixture was allowed to stir at room temperature for 30 min, after which solution became clear and LCMS analysis showed completion. Reaction mixture was concentrated to a slurry and poured into cold 1M HCl solution and stirred vigorously for 10 min. Insoluble product was filtered, rinsed with $H_2O$ and air dried to afford 4-(6-phenyl-[1,2,4]triazolo[4,3-a]pyridin-3-yl)benzoic acid (248 mg, 0.786 mmol, 89% yield) as an off-white solid, which was used without further purification. LCMS RT (Method 2)=2.956 min, m/z 316.8 [M+H$^+$].

Example 25

Synthesis of N-(3-(2-Oxopyrrolidin-1-yl)propyl)-4-(6-phenyl-[1,2,4]triazolo[4,3-a]pyridin-3-yl)benzamide (Compound 31)

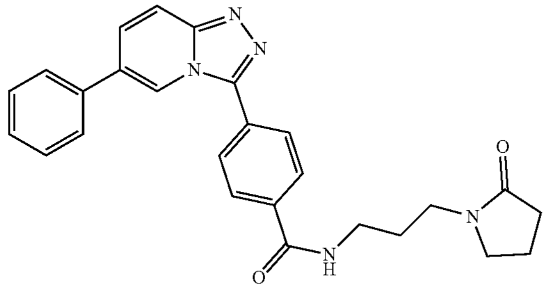

Chemical Formula: $C_{26}H_{25}N_5O_2$
Exact Mass: 439.20
Molecular Weight: 439.52

A mixture of 4-(6-phenyl-[1,2,4]triazolo[4,3-a]pyridin-3-yl)benzoic acid (100 mg, 0.317 mmol) and HATU (145 mg, 0.381 mmol) in DMF (2.00 mL) were stirred for 10 min, after which was added 1-(3-aminopropyl)pyrrolidin-2-one (0.049 mL, 0.349 mmol). The resulting reaction mixture was stirred for 20 min, after which was added DIPEA (0.138 mL, 0.793 mmol) and the reaction stirred overnight, after which LCMS analysis showed completion. Reaction mixture was diluted with EtOAc, washed with $H_2O$ and brine, dried over anhydrous $MgSO_4$, filtered and concentrated. Residue was purified by flash column chromatography: silica gel with a gradient of 0-30% MeOH in EtOAc to afford N-(3-(2-oxopyrrolidin-1-yl)propyl)-4-(6-phenyl-[1,2,4]triazolo[4,3-a]pyridin-3-yl)benzamide (33.0 mg, 0.075 mmol, 23.68% yield) as a white solid. $^1$H NMR (400 MHz, DMSO-$d_6$) δ 8.68-8.61 (m, 2H), 8.14-8.10 (m, 2H), 8.08 (d, J=8.8 Hz, 2H), 7.99 (dd, J=9.6, 1.0 Hz, 1H), 7.85-7.74 (m, 3H), 7.54-7.48 (m, 2H), 7.47-7.41 (m, 1H), 3.40-3.34 (m, 2H), 3.27 (q, J=6.9 Hz, 4H), 2.23 (dd, J=8.6, 7.5 Hz, 2H), 2.01-1.87 (m, 2H), 1.74 (p, J=7.0 Hz, 2H). LCMS RT (Method 1)=4.071 min, m/z 440.1 [M+H$^+$].

Example 26

Synthesis of Methyl 4-((2-chloro-5-nitropyridin-4-yl)amino)benzoate

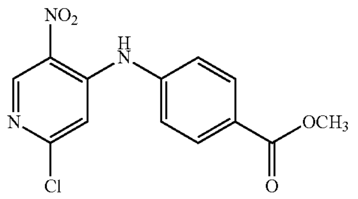

Chemical Formula: $C_{13}H_{10}ClN_3O_4$
Exact Mass: 307.04
Molecular Weight: 307.69

A mixture of 2-chloro-5-nitropyridin-4-amine (200 mg, 1.152 mmol), methyl 4-iodobenzoate (302 mg, 1.152 mmol), copper(I) iodide (32.9 mg, 0.173 mmol) and cesium carbonate (563 mg, 1.73 mmol) were placed in a vial, sealed and purged with $N_2$ for 3 min. DMF (4.00 mL) was added and the reaction mixture purged by bubbling $N_2$ through the mixture for 3 min. The resulting reaction mixture was placed in a preheated reaction block at 120° C. and stirred for 16 h, after which LCMS analysis showed product formation. Reaction mixture was partitioned between EtOAc and $H_2O$, filtered through celite, the layers separated, and the organic phase washed with brine, dried over anhydrous $MgSO_4$, filtered and concentrated. Crude residue was purified by flash column chromatography: silica gel with a gradient of 10-30% EtOAc in Hex to afford methyl 4-((2-chloro-5-nitropyridin-4-yl)amino)benzoate (84.0 mg, 0.273 mmol, 23.69% yield). $^1$H NMR (400 MHz, DMSO-$d_6$) δ 10.04 (s, 1H), 8.99 (s, 1H), 8.08-8.00 (m, 2H), 7.57-7.49 (m, 2H), 7.03 (s, 1H), 3.87 (s, 3H). LCMS RT (Method 2)=3.334 min, m/z 308.0 [M+H$^+$].

Example 27

Synthesis of Methyl 4-((5-amino-2-chloropyridin-4-yl)amino)benzoate

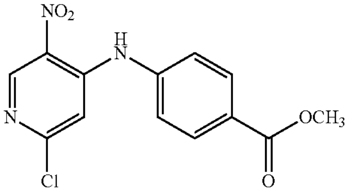

Chemical Formula: $C_{13}H_{12}ClN_3O_2$
Exact Mass: 277.06
Molecular Weight: 277.71

A mixture of methyl 4-((2-chloro-5-nitropyridin-4-yl)amino)benzoate (80.0 mg, 0.260 mmol), iron powder (72.6 mg, 1.30 mmol) and ammonium chloride (278 mg, 5.20 mmol) in 1:1 EtOH—$H_2O$ (10.0 mL) was stirred at 70° C. for 1 h, after which LCMS analysis showed completion. Reaction mixture was allowed to cool to room temperature and partition between brine and EtOAc, filtered through celite and the layers separated. The organic phase was washed with brine, dried over anhydrous $MgSO_4$, filtered and concentrated to afford crude methyl 4-((5-amino-2-chloropyridin-4-yl)amino)benzoate (70.0 mg, 0.252 mmol, 97% yield) as a tan solid, which was used without further purification. LCMS RT (Method 2)=2.573 min, m/z 278.0 $[M+H^+]$.

Example 28

Synthesis of Methyl 4-(6-chloro-1H-imidazo[4,5-c]pyridin-1-yl)benzoate

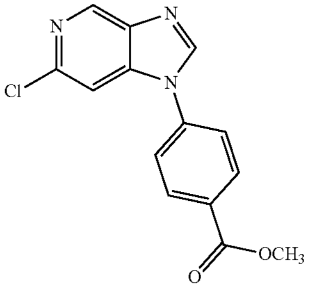

Chemical Formula: $C_{14}H_{10}ClN_3O_2$
Exact Mass: 287.05
Molecular Weight: 287.70

A solution of methyl 4-((5-amino-2-chloropyridin-4-yl)amino)benzoate (65.0 mg, 0.234 mmol), triethyl orthoformate (0.100 mL, 0.601 mmol) and catalytic p-toluenesulfonic acid (p-TsOH) (6.68 mg, 0.035 mmol) in THF (5.00 mL) was stirred at 60° C. overnight, after which LCMS analysis showed completion. Reaction mixture was diluted with EtOAc and washed with saturated $NaHCO_3$, brine, dried over anhydrous $MgSO_4$, filtered and concentrated. Crude residue was purified by flash column chromatography: silica gel with a gradient of 20-80% EtOAc in HEX to afford methyl 4-(6-chloro-1H-imidazo[4,5-c]pyridin-1-yl)benzoate (41.0 mg, 0.143 mmol, 60.9% yield) as a white powder. $^1H$ NMR (400 MHz, Chloroform-d) δ 8.97 (d, J=0.9 Hz, 1H), 8.34-8.28 (m, 2H), 8.22 (s, 1H), 7.61-7.58 (m, 2H), 7.54 (d, J=0.9 Hz, 1H), 4.00 (s, 3H). LCMS RT (Method 2)=3.034 min, m/z 287.8 $[M^+]$.

Example 29

Synthesis of 4-(6-Phenyl-1H-imidazo[4,5-c]pyridin-1-yl)benzoic acid

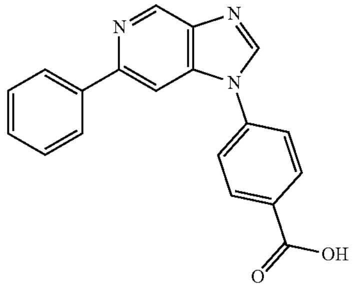

Chemical Formula: $C_{19}H_{13}N_3O_2$
Exact Mass: 315.10
Molecular Weight: 315.33

A mixture of methyl 4-(6-chloro-1H-imidazo[4,5-c]pyridin-1-yl)benzoate (35.0 mg, 0.122 mmol), phenylboronic acid (18.54 mg, 0.152 mmol), XPhos Pd(crotyl)Cl (4.10 mg, 6.08 μmol) and $K_3PO_4$ (51.6 mg, 0.243 mmol) were placed in a vial and purged with $N_2$ for 2 min. 4:1 Dioxane:$H_2O$ (2.50 mL) was added and degassing continued for 2 min, after which reaction vessel was placed in a preheated block at 100° C. After stirring for 30 min at 100° C. LCMS analysis showed completion. Reaction mixture was then treated with 2M sodium hydroxide (0.500 mL, 1.00 mmol) and stirring continued at 100° C. for 30 min, after which LCMS analysis showed complete saponification of ester. Reaction mixture was allowed to cool to room temperature and diluted with EtOAc and $H_2O$. pH was adjusted to ~4-5 with AcOH and biphasic mixture filtered through celite, the layers separated and the organic phase washed with brine, dried over anhydrous $MgSO_4$, filtered and concentrated to afford crude 4-(6-phenyl-1H-imidazo[4,5-c]pyridin-1-yl)benzoic acid (35.0 mg, 0.111 mmol, 91% yield), which was used without further purification. LCMS RT (Method 2)=2.601 min, m/z 315.8 [M+].

Example 30

Synthesis of N-(3-(2-Oxopyrrolidin-1-yl)propyl)-4-(6-phenyl-1H-imidazo[4,5-c]pyridin-1-yl)benzamide (Compound 32)

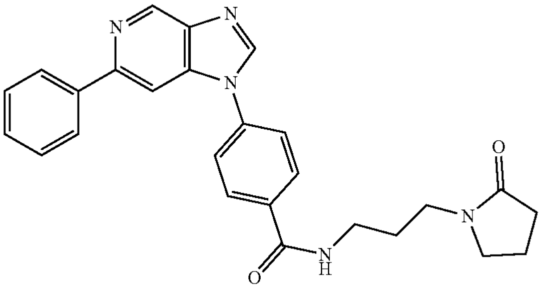

Chemical Formula: $C_{26}H_{25}N_5O_2$
Exact Mass: 439.20
Molecular Weight: 439.52

A mixture of 4-(6-phenyl-1H-imidazo[4,5-c]pyridin-1-yl) benzoic acid (40.0 mg, 0.127 mmol) and HATU (57.9 mg, 0.152 mmol) in DMF (1.50 mL) were stirred for 10 min, after which was added 1-(3-aminopropyl)pyrrolidin-2-one (19.57 μL, 0.140 mmol). The resulting reaction mixture was stirred for 20 min, after which was added DIPEA (55.4 μL, 0.317 mmol) and the reaction stirred overnight, after which LCMS analysis showed completion. Reaction mixture was diluted with EtOAc, washed with $H_2O$ and brine, dried over anhydrous $MgSO_4$, filtered and concentrated. Residue was purified by flash column chromatography: silica gel with a gradient of 0-20% MeOH in EtOAc to afford N-(3-(2-oxopyrrolidin-1-yl)propyl)-4-(6-phenyl-1H-imidazo[4,5-c] pyridin-1-yl)benzamide (32.0 mg, 0.073 mmol, 57.4% yield) as an off-white solid. $^1H$ NMR (400 MHz, DMSO-$d_6$) δ 9.17 (d, J=1.0 Hz, 1H), 8.82 (s, 1H), 8.65 (t, J=5.7 Hz, 1H), 8.19-8.08 (m, 5H), 7.97-7.88 (m, 2H), 7.51-7.44 (m, 2H), 7.43-7.37 (m, 1H), 3.37 (t, J=7.0 Hz, 2H), 3.28 (dt, J=15.9, 6.9 Hz, 4H), 2.24 (dd, J=8.6, 7.4 Hz, 2H), 1.94 (ddd, J=15.4, 13.1, 6.4 Hz, 2H), 1.75 (p, J=7.1 Hz, 2H). LCMS RT (Method 1)=3.523 min, m/z 440.8 $[M+H^+]$.

Example 31

Synthesis of Methyl 4-(6-chloro-1H-pyrrolo[3,2-c] pyridin-1-yl)benzoate

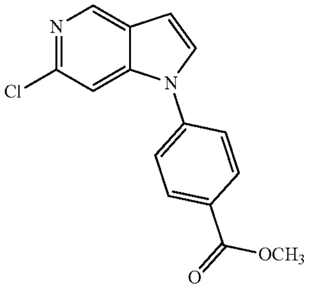

Chemical Formula: $C_{15}H_{11}ClN_2O_2$
Exact Mass: 286.05
Molecular Weight: 286.72

A mixture of 6-chloro-1H-pyrrolo[3,2-c]pyridine (200 mg, 1.31 mmol), methyl 4-iodobenzoate (343 mg, 1.31 mmol), copper(I) iodide (37.4 mg, 0.197 mmol) and cesium carbonate (641 mg, 1.97 mmol) were placed in a vial, sealed and purged with $N_2$ for 3 min. DMF (4.00 mL) was added and the reaction mixture purged by bubbling $N_2$ through the mixture for 3 min. The resulting reaction mixture was placed in a preheated reaction block at 120° C. and stirred for 16 h, after which LCMS analysis showed product formation. Reaction mixture was partitioned between EtOAc and $H_2O$, filtered through celite, the layers separated, and the organic phase washed with brine, dried over anhydrous $MgSO_4$, filtered and concentrated. Crude residue was purified by flash column chromatography: silica gel with a gradient of 5-35% EtOAc in Hex to afford methyl 4-(6-chloro-1H-pyrrolo[3,2-c]pyridin-1-yl)benzoate (213 mg, 0.743 mmol, 56.7% yield). LCMS RT (Method 2)=3.247 min, m/z 287.0 $[M+H^+]$.

Example 32

Synthesis of Methyl 4-(6-phenyl-1H-pyrrolo[3,2-c] pyridin-1-yl)benzoate

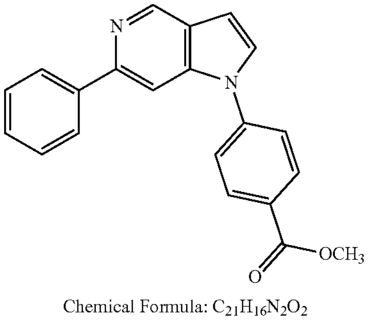

Chemical Formula: $C_{21}H_{16}N_2O_2$
Exact Mass: 328.12
Molecular Weight: 328.37

A mixture of methyl 4-(6-chloro-1H-pyrrolo[3,2-c]pyridin-1-yl)benzoate (100 mg, 0.349 mmol), phenylboronic acid (53.2 mg, 0.436 mmol), XPhosPd(crotyl)Cl (11.75 mg, 0.017 mmol) and $K_3PO_4$ (148 mg, 0.698 mmol) were placed in a vial and purged with $N_2$ for 2 min. 4:1 Dioxane:$H_2O$ (2.50 mL) was added and degassing continued for 2 min, after which reaction vessel was placed in a preheated block at 100° C. After stirring for 30 min at 100° C. LCMS analysis showed completion. Reaction mixture was allowed to cool to room temperature, partitioned between brine and EtOAc, filtered through celite and the layers separated. The organic phase was washed with brined, dried over anhydrous $MgSO_4$, filtered and concentrated. Crude product was purified by flash column chromatography: silica gel with a gradient of 10-35% EtOAc in Hex to afford methyl 4-(6-phenyl-1H-pyrrolo[3,2-c]pyridin-1-yl)benzoate (110 mg, 0.335 mmol, 96% yield). LCMS RT (Method 2)=2.795 min, m/z 329.1 $[M+H^+]$.

Example 33

Synthesis of 4-(6-Phenyl-1H-pyrrolo[3,2-c]pyridin-1-yl)benzoic acid

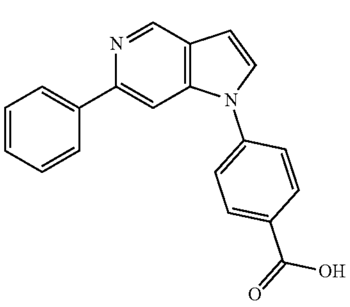

Chemical Formula: $C_{20}H_{14}N_2O_2$
Exact Mass: 314.11
Molecular Weight: 314.34

2M sodium hydroxide (2.00 mL, 4.00 mmol) was added to a solution of methyl 4-(6-phenyl-1H-pyrrolo[3,2-c]pyridin-1-yl)benzoate (100 mg, 0.305 mmol) in EtOH (5.00 mL). The resulting reaction mixture was stirred at room temperature for 2 h, after which LCMS analysis showed completion. Reaction mixture was concentrated to a slurry and residue partitioned between 1M HCl and EtOAc, the layers separated and the organic phase washed with brine, dried over anhydrous $MgSO_4$, filtered and concentrated to afford crude 4-(6-phenyl-1H-pyrrolo[3,2-c]pyridin-1-yl) benzoic acid (55.0 mg, 0.175 mmol, 57.5% yield), which was used without further purification. LCMS RT (Method 2)=2.664 min, m/z 314.9 [M+].

Example 34

Synthesis of N-(3-(2-Oxopyrrolidin-1-yl)propyl)-4-(6-phenyl-1H-pyrrolo[3,2-c]pyridin-1-yl)benzamide (Compound 33)

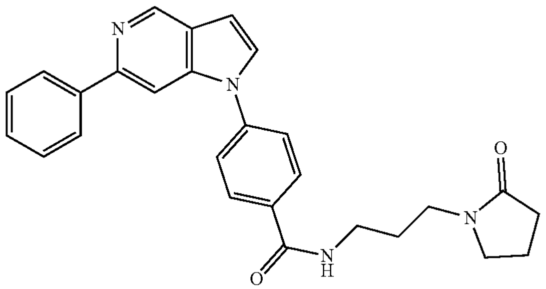

Chemical Formula: $C_{27}H_{26}N_4O_2$
Exact Mass: 438.21
Molecular Weight: 438.53

A mixture of 4-(6-phenyl-1H-pyrrolo[3,2-c]pyridin-1-yl) benzoic acid (25.0 mg, 0.080 mmol) and HATU (36.3 mg, 0.095 mmol) in DMF (1.50 mL) were stirred for 10 min, after which was added 1-(3-aminopropyl)pyrrolidin-2-one (12.3 μL, 0.087 mmol). The resulting reaction mixture was stirred for 20 min, after which was added DIPEA (34.7 μL, 0.199 mmol) and the reaction stirred overnight, after which LCMS analysis showed completion. Reaction mixture was diluted with EtOAc, washed with $H_2O$ and brine, dried over anhydrous $MgSO_4$, filtered and concentrated. Residue was purified by flash column chromatography: silica gel with a gradient of 0-20% MeOH in EtOAc to afford N-(3-(2-oxopyrrolidin-1-yl)propyl)-4-(6-phenyl-1H-pyrrolo[3,2-c] pyridin-1-yl)benzamide (17.0 mg, 0.039 mmol, 48.7% yield) as an off-white solid. $^1H$ NMR (400 MHz, DMSO-$d_6$) δ 9.04 (s, 1H), 8.62 (t, J=5.6 Hz, 1H), 8.10 (t, J=7.4 Hz, 4H), 8.02 (s, 1H), 7.88 (d, J=3.4 Hz, 1H), 7.83 (d, J=8.4 Hz, 2H), 7.46 (t, J=7.5 Hz, 2H), 7.37 (t, J=7.2 Hz, 1H), 6.93 (d, J=3.3 Hz, 1H), 3.37 (t, J=7.0 Hz, 2H), 3.27 (q, J=7.1, 6.6 Hz, 4H), 2.23 (t, J=8.1 Hz, 2H), 1.93 (p, J=7.5 Hz, 2H), 1.74 (p, J=7.1 Hz, 2H). LCMS RT (Method 1)=3.521 min, m/z 439.1 [M+H$^+$].

Example 35

Synthesis of methyl 4-(((5-phenylpyrazin-2-yl) methyl)carbamoyl)benzoate

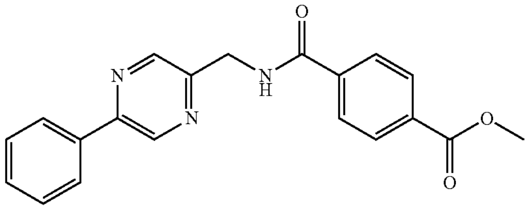 [SMILES: COC(=O)c1ccc(C(=O)NCc2cnc(-c3ccccc3)cn2)cc1]

A heterogeneous solution consisting of (5-phenylpyrazin-2-yl)methanamine (Key Organics) (3.3 g, 17.82 mmol), 4-(methoxycarbonyl)benzoic acid (3.53 g, 19.60 mmol), HOBt (3.55 g, 23.16 mmol), DIPEA (9.33 ml, 53.4 mmol) in DMF (100 ml) was stirred at 65° C. under $N_2$ for 1 minute. To the solution was added EDC (4.10 g, 21.38 mmol). The solution was stirred at 65° C. under $N_2$ for 2.5 hrs. The solution was cooled to room temperature. To the solution was added water (500 ml). The solution was cooled for 18 hrs. The solution was filtered. The solid was washed with water (3×), dried in air then in vacuo to give the desired compound (5.4 g, 87%). (LCMS, ESI pos.) Calculated for $C_{20}H_{17}N_3O_3$: 348.4 (M+H), Measured: 348.1. $^1H$ NMR (400 MHz, DMSO-$d_6$) δ 9.43 (t, J=5.7 Hz, 1H), 9.23 (d, J=1.5 Hz, 1H), 8.76 (d, J=1.5 Hz, 1H), 8.19-8.14 (m, 2H), 8.13-8.05 (m, 4H), 7.61-7.50 (m, 3H), 4.72 (d, J=5.7 Hz, 2H), 3.93 (s, 3H).

Example 36

Synthesis of methyl 4-(6-phenylimidazo[1,5-a] pyrazin-3-yl)benzoate

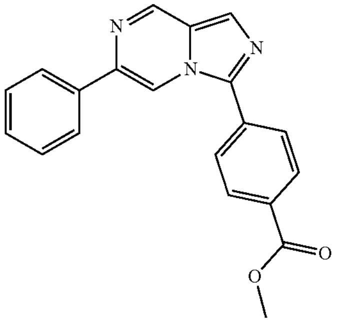 [SMILES: COC(=O)c1ccc(-c2ncc3cnc(-c4ccccc4)cn23)cc1]

A heterogeneous solution of methyl 4-(((5-phenylpyrazin-2-yl)methyl)carbamoyl)benzoate (2.5 g, 7.20 mmol) and pyridine (3.49 ml, 43.2 mmol) in DCE (72.0 ml) was treated dropwise with $POCl_3$ (2.68 ml, 28.8 mmol) over 1 min. The heterogeneous solution was stirred at 70° C. under $N_2$. The solution was stirred at 70° C. for 5 h. The reaction was cooled to room temperature. The solution was cooled (ice bath). To the solution was added slowly MeOH (10 ml). The solution was concentrated to a small volume that was chromatographed using gradient silica gel chromatography (5% EtOAc in hexanes to 100% EtOAc over 20 min). Desired fractions were pooled, concentrated and dried in vacuo to give desired compound (1.8 g, 76%). (LCMS, ESI pos.) Calculated for $C_{20}H_{15}N_3O_2$: 330.4 (M+H), Measured: 330.1. $^1H$ NMR (400 MHz, DMSO-$d_6$) δ 9.34 (d, J=1.5 Hz, 1H), 8.82 (t, J=1.3 Hz, 1H), 8.21 (d, J=1.1 Hz, 4H), 8.15-8.08 (m, 3H), 7.59-7.49 (m, 2H), 7.49-7.42 (m, 1H), 3.95 (d, J=1.2 Hz, 3H).

Example 37

Synthesis of 4-(6-phenylimidazo[1,5-a]pyrazin-3-yl) benzoic acid

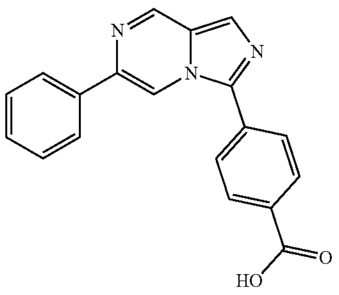 [SMILES: O=C(O)c1ccc(-c2ncc3cnc(-c4ccccc4)cn23)cc1]

To a solution of methyl 4-(6-phenylimidazo[1,5-a] pyrazin-3-yl)benzoate (1.8 g, 5.47 mmol) in MeOH/THF 1:1 (40 ml) was added sodium hydroxide (10.93 ml, 10.93 mmol). The solution was stirred at room temperature under $N_2$. After 3 h the reaction solution was concentrated to a small volume. The solution was cooled using an ice/water bath. The pH was adjusted to 2 (litmus) using 1N HCl (slow addition). The solution was placed in the refrigerator overnight. The solution was filtered. The solid was washed with water (3×). The solid was dried in air then in vacuo to give desired product (1.0 g, 58%). (LCMS, ESI pos.) Calculated for $C_{19}H_{13}N_3O_2$: 316.3 (M+H), Measured: 316.1. $^1H$ NMR (400 MHz, DMSO-$d_6$) δ 13.23 (s, 1H), 9.27 (s, 1H), 8.75 (s, 1H), 8.07 (m, J=21.4 Hz, 7H), 7.43 (m, J=23.8 Hz, 3H).

Example 38

Synthesis of N-(2-(1H-imidazol-5-yl)ethyl)-4-(6-phenylimidazo[1,5-a]pyrazin-3-yl)benzamide (Compound 1)

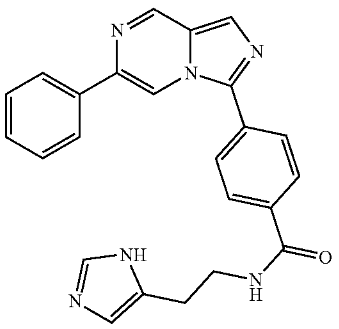 [SMILES: O=C(NCCc1cnc[nH]1)c1ccc(-c2ncc3cnc(-c4ccccc4)cn23)cc1]

A solution of 4-(6-phenylimidazo[1,5-a]pyrazin-3-yl) benzoic acid (1 g, 3.17 mmol) in DMF (10.57 ml) was treated with DIPEA (1.108 ml, 6.34 mmol). To the solution was added HATU (1.326 g, 3.49 mmol). The solution was stirred at room temperature under $N_2$. After 30 min histamine (0.388 g, 3.49 mmol) was added to the solution. The reaction solution was stirred at room temperature under $N_2$ for 18 hrs. To the reaction solution was added 1N NaOH (1.9 mmol). After 30 minutes the solution was concentrated to a small volume. The solution was partitioned between EtOAc and water. The EtOAc layer was separated and washed successively with water (2×), brine (1×), dried over anhydrous $MgSO_4$, filtered and concentrated. The residue was chromatographed using C18 reversed-phase chromatography to give the desired compound (0.7 g, 54%). (LCMS, ESI pos.) Calculated for $C_{24}H_{20}N_6O$: 409.5 (M+H), Measured: 409.2. $^1H$ NMR (400 MHz, DMSO-$d_6$) δ 11.87 (s, 1H), 9.33 (d, J=1.5 Hz, 1H), 8.84-8.71 (m, 2H), 8.22-8.03 (m, 7H), 7.69-7.40 (m, 4H), 6.90 (s, 1H), 3.57 (td, J=7.5, 5.5 Hz, 2H), 2.83 (s, 2H).

Figure 15:
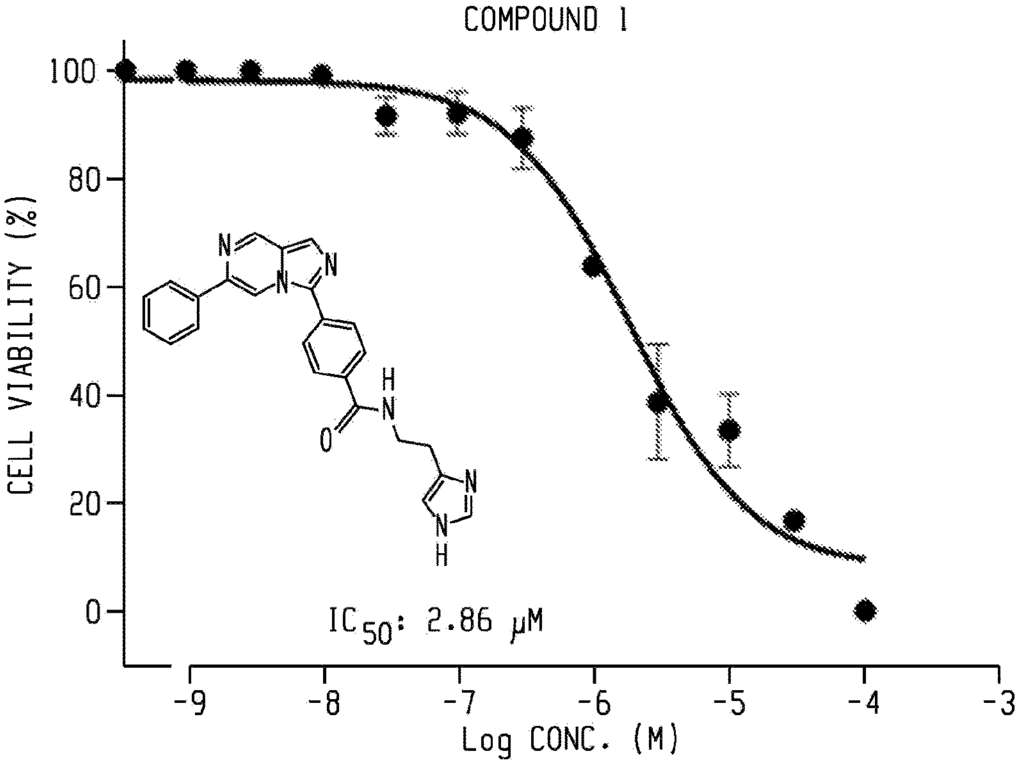
FIG. 15 shows a graph of Percentage Relative Cell Viability versus Log Molar Concentration illustrating macrophage activity of Compound 1 with IC50 of 2.86 μM.

FIG. 15 shows IC50 of 2.86 μM for Compound 1.

Figure 10A:
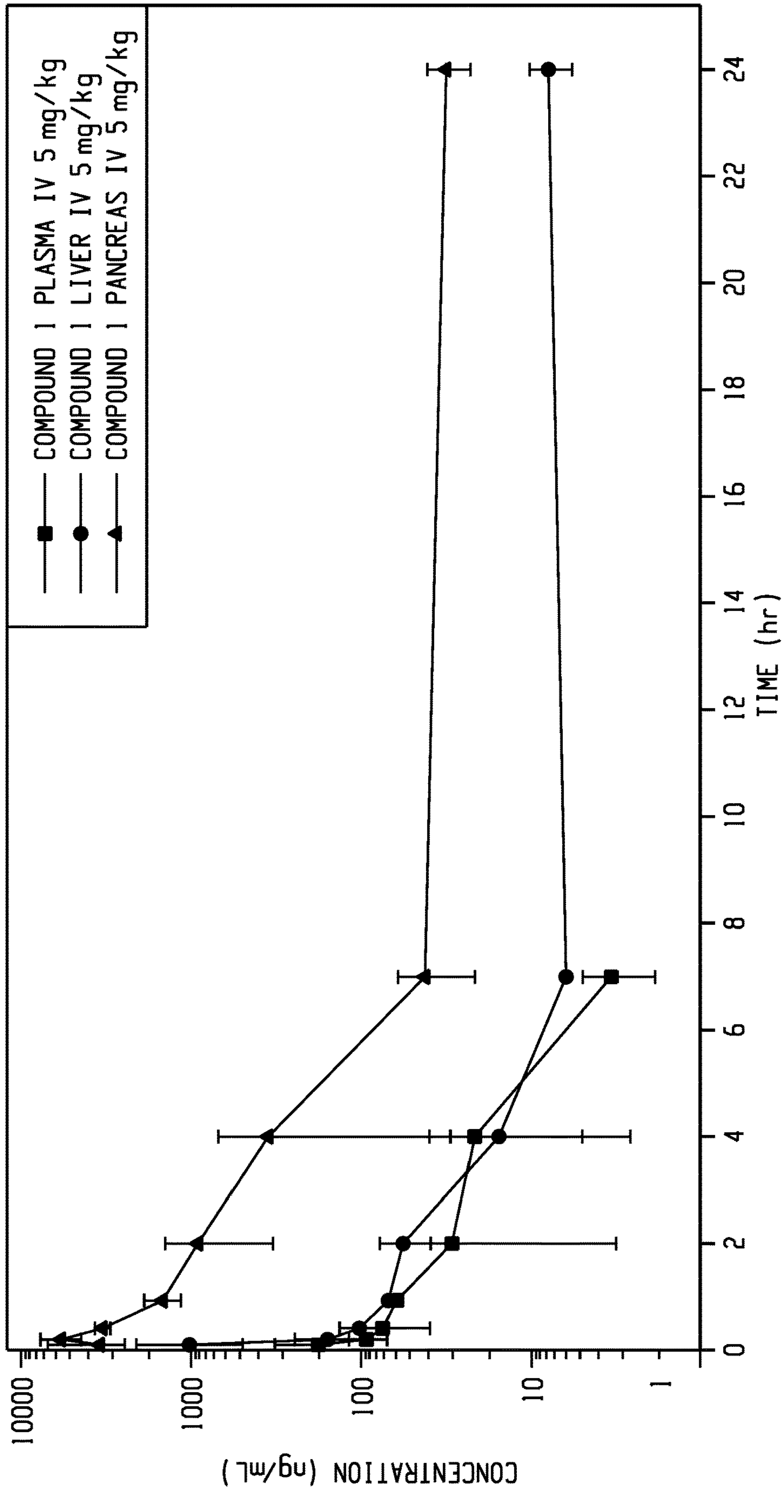
FIG. 10A shows a graph of Time in hours (hr) versus Concentration in nanograms per milliliters (ng/mL) of Compound 1 illustrating pharmacokinetics (PK) profile of Compound 1 at different concentrations when given via intravenous (IV) injection.
Figure 10B:
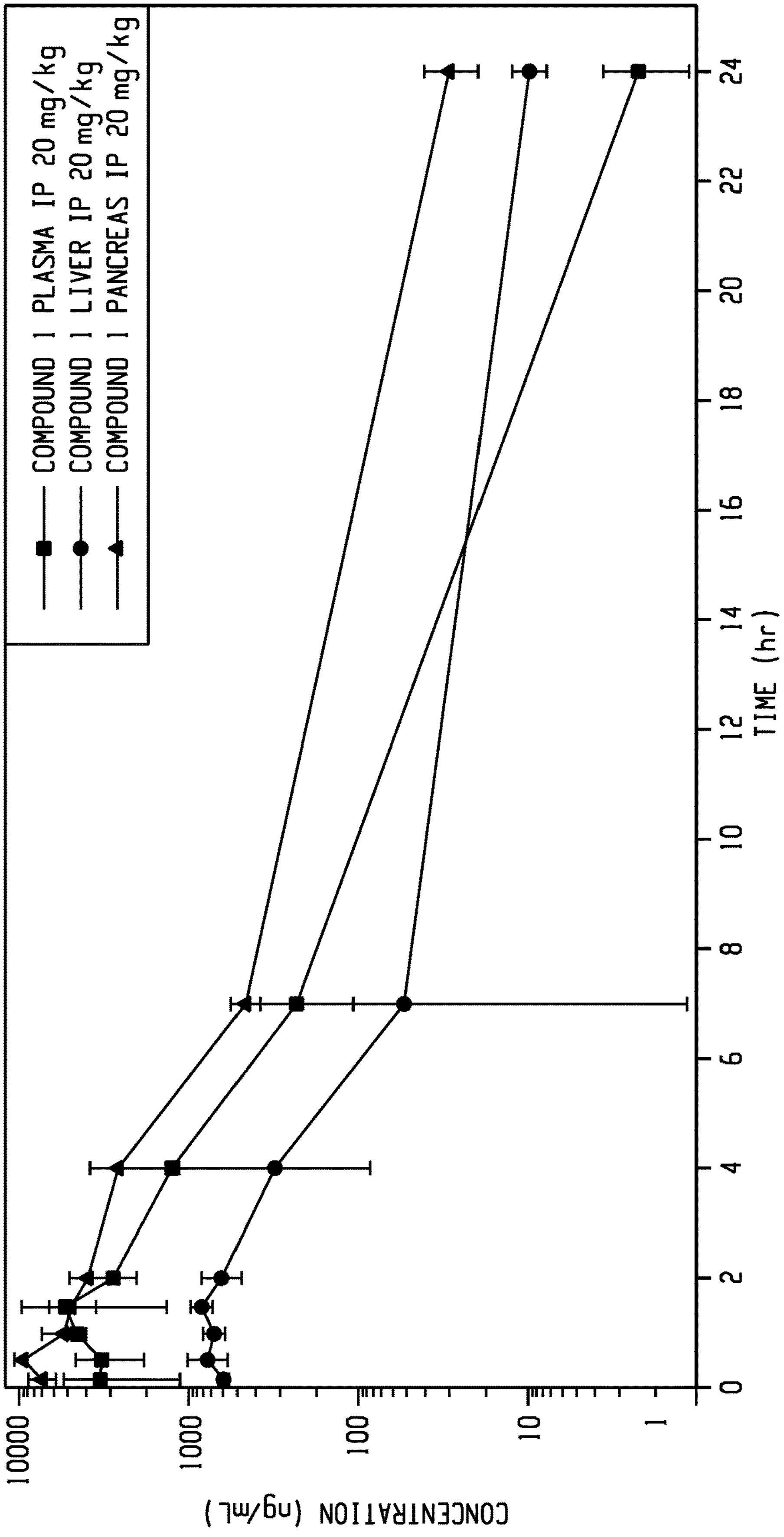
FIG. 10B shows a graph of Time (hr) versus Concentration (ng/mL) of Compound 1 illustrating pharmacokinetics (PK) profile of Compound 1 at different concentrations when given via intraperitoneal (IP) injection.
Figure 10C:
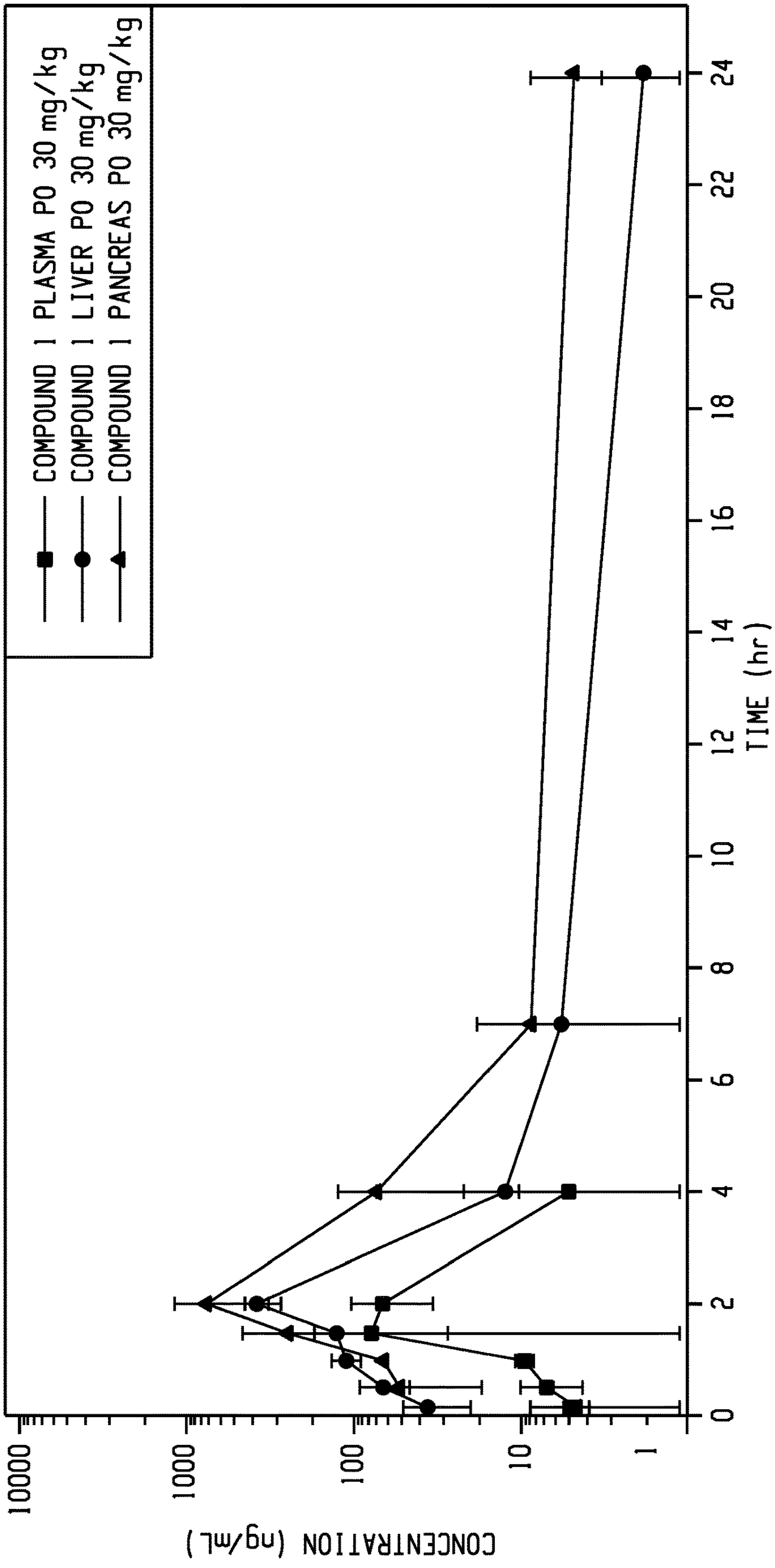
FIG. 10C shows a graph of Time (hr) versus Concentration (ng/mL) of Compound 1 illustrating pharmacokinetics (PK) profile of Compound 1 at different concentrations when given orally.

As shown in FIGS. 10A to 10C and Table 1, Compound-1 showed excellent PK profile at different concentrations is plasma, liver, and pancreas when administered using both the routes oral as well as IP injection.

TABLE 1

| Compound | Compound 1 | Compound 1 |
|---|---|---|
| Sample<br>Route<br>Dose (mg/kg) | Plasma<br>IP (intraperitoneal)<br>20 | Plasma<br>PO (Per Os, oral)<br>30 |
| Time (h) | μM | μM |
| 0.157 | 7.89 | 0.011 |
| 0.5 | 7.60 | 0.016 |
| 1.0 | 11.10 | 0.023 |
| 1.5 | 12.75 | 0.190 |
| 2.0 | 5.84 | 0.163 |
| 4.0 | 3.02 | 0.011 |
| 7.0 | 0.54 | N/A |

Example 39

Synthesis of N-(3-(2-oxopyrrolidin-1-yl)propyl)-4-(6-phenylimidazo[1,5-a]pyrazin-3-yl)benzamide (Compound 28)

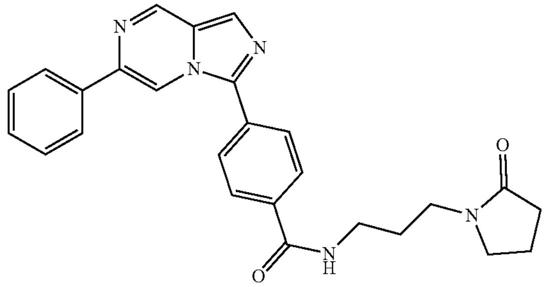 [SMILES: O=C(NCCCN1CCCC1=O)c1ccc(-c2ncc3cnc(-c4ccccc4)cn23)cc1]

A solution of 4-(6-phenylimidazo[1,5-a]pyrazin-3-yl) benzoic acid (0.255 g, 0.809 mmol) and HATU (0.369 g, 0.970 mmol) in DMF (2.70 ml) was treated with DIPEA (0.282 ml, 1.617 mmol). The solution was stirred at room temperature under $N_2$. After 20 min a solution of 1-(3-aminopropyl)pyrrolidin-2-one (0.126 g, 0.890 mmol) in DMF (0.1 ml) was added to the solution. The reaction solution was stirred at room temperature under $N_2$. After 18 h the reaction solution was introduced into a C18 column (15.5 g, equilibrated with water) and purified using a gradient (0-30% $CH_3CN$ over 20 min) to give the desired compound (0.142 g, 40%). (LCMS, ESI pos.) Calculated for $C_{26}H_{25}N_5O_2$: 440.5 (M+H), Measured: 440.2. $^1H$ NMR (400 MHz, DMSO-$d_6$) δ 9.34 (d, J=1.5 Hz, 1H), 8.79 (t, J=1.3 Hz, 1H), 8.66 (t, J=5.7 Hz, 1H), 8.19-8.05 (m, 7H), 7.53 (dd, J=8.3, 6.6 Hz, 2H), 7.49-7.43 (m, 1H), 3.41 (t, J=7.0 Hz, 2H), 3.32 (dt, J=14.0, 6.9 Hz, 4H), 2.27 (t, J=8.1 Hz, 2H), 2.05-1.91 (m, 2H), 1.78 (p, J=7.1 Hz, 2H).

Example 40

Synthesis of (3-hydroxyazetidin-1-yl)(4-(6-phenylimidazo[1,5-a]pyrazin-3-yl)phenyl)methanone (Compound 17)

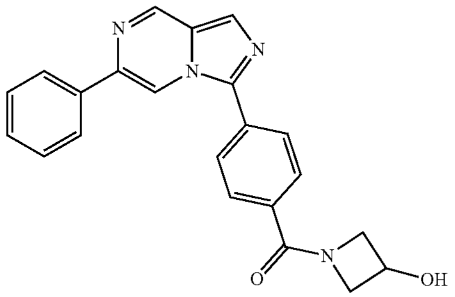 [SMILES: O=C(c1ccc(-c2ncc3cnc(-c4ccccc4)cn23)cc1)N1CC(O)C1]

A solution of 4-(6-phenylimidazo[1,5-a]pyrazin-3-yl) benzoic acid (0.05 g, 0.159 mmol) and HATU (0.066 g, 0.174 mmol) in DMF (0.317 ml) was treated with DIPEA (0.033 ml, 0.190 mmol). After 10 min azetidin-3-ol (0.012 g, 0.159 mmol) was added to the solution. The solution was stirred at room temperature overnight. The solution was introduced into a 24 g silica gel column equilibrated with EtOAc. Elution was done with a gradient (EtOAc to 10% MeOH/EtOAc). Desired fractions were combined, concentrated and dried in vacuo to give the desired compound (0.04 g, 68%). (LCMS, ESI pos.) Calculated for $C_{22}H_{18}N_4O_2$: 371.4 (M+H), Measured: 371.2. $^1H$ NMR (400 MHz, DMSO-$d_6$) δ 9.33 (d, J=1.5 Hz, 1H), 8.81-8.76 (m, 1H), 8.57 (dd, J=8.4, 1.4 Hz), 8.16-8.06 (m, 4H), 7.91-7.84 (m, 2H), 7.57-7.49 (m, 2H), 7.49-7.43 (m, 1H), 5.83 (s, 1H), 4.57 (d, J=5.1 Hz, 2H), 4.33 (s, 1H), 4.16 (s, 1H), 3.94-3.84 (m, 1H), 1.29 (td, J=7.1, 5.1 Hz, 3H).

Example 41

Synthesis of (4-hydroxypiperidin-1-yl)(4-(6-phenylimidazo[1,5-a]pyrazin-3-yl)phenyl)methanone (Compound 18)

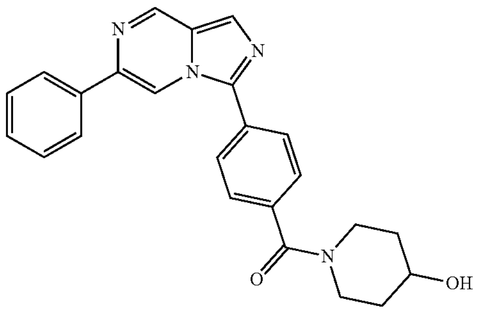 [SMILES: O=C(c1ccc(-c2ncc3cnc(-c4ccccc4)cn23)cc1)N1CCC(O)CC1]

A solution of 4-(6-phenylimidazo[1,5-a]pyrazin-3-yl) benzoic acid (0.05 g, 0.159 mmol) and HATU (0.066 g, 0.174 mmol) in DMF (0.5 ml) was treated with DIPEA (0.033 ml, 0.190 mmol). The solution was stirred at room temperature for 10 min. To the solution was added piperidin-4-ol (0.016 g, 0.159 mmol). The solution was stirred at room temperature overnight. The solution was introduced into a 24 g silica gel column equilibrated with EtOAc. Elution was done with a gradient (EtOAc to 10% MeOH/EtOAc). Desired fractions were combined, concentrated and dried in vacuo to give the desired compound (0.03 g, 48%). (LCMS, ESI pos.) Calculated for $C_{24}H_{22}N_4O_2$: 399.5 (M+H), Measured: 399.2. $^1H$ NMR (400 MHz, DMSO-$d_6$) δ 9.32 (d, J=1.5 Hz, 1H), 8.80 (t, J=1.2 Hz, 1H), 8.16-8.05 (m, 5H), 7.70-7.58 (m, 2H), 7.58-7.42 (m, 3H), 4.86 (s, 1H), 3.86-3.76 (m, 1H), 3.63 (s, 1H), 3.28 (s, 3H), 1.82 (s, 2H), 1.44 (s, 3H).

Example 42

Synthesis of N-(2-(dimethylamino)ethyl)-N-methyl-4-(6-phenylimidazo[1,5-a]pyrazin-3-yl)benzamide (Compound 19)

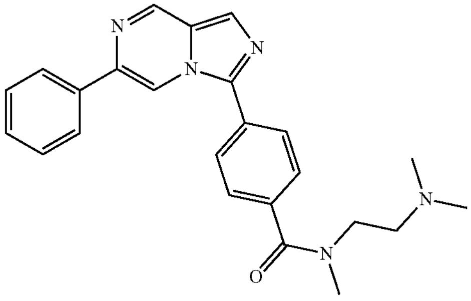 [SMILES: CN(C)CCN(C)C(=O)c1ccc(-c2ncc3cnc(-c4ccccc4)cn23)cc1]

A solution of 4-(6-phenylimidazo[1,5-a]pyrazin-3-yl) benzoic acid (0.05 g, 0.159 mmol) and HATU (0.066 g, 0.174 mmol) in DMF (0.5 ml) was treated with DIPEA (0.033 ml, 0.190 mmol). After 10 min N1,N1,N2-trimethylethane-1,2-diamine (0.021 ml, 0.159 mmol) was added. The solution was stirred at room temperature overnight. The solution was introduced into a 24 g silica gel column equilibrated with EtOAc. Elution was done with a gradient (EtOAc to 10% MeOH/EtOAc). Desired fractions were combined, concentrated and dried in vacuo to give the desired compound (0.03 g, 47%). (LCMS, ESI pos.) Calculated for $C_{24}H_{25}N_5O$: 400.5 (M+H), Measured: 400.2. $^1H$ NMR (400 MHz, DMSO-$d_6$) δ 9.10 (d, J=1.5 Hz, 1H), 8.41 (t, J=1.2 Hz, 1H), 7.93 (d, J=1.0 Hz, 1H), 7.87 (td, J=6.1, 2.8 Hz, 4H), 7.66-7.59 (m, 2H), 7.52-7.44 (m, 2H), 7.43-7.37 (m, 1H), 3.68 (s, 1H), 3.40 (d, J=10.2 Hz, 1H), 3.09 (d, J=29.0 Hz, 3H), 2.67-2.38 (m, 2H), 2.32 (s, 3H), 2.10 (s, 3H).

Example 43

Synthesis of N-(4-acetamidophenyl)-4-(6-phenylimidazo[1,5-a]pyrazin-3-yl)benzamide (Compound 5)

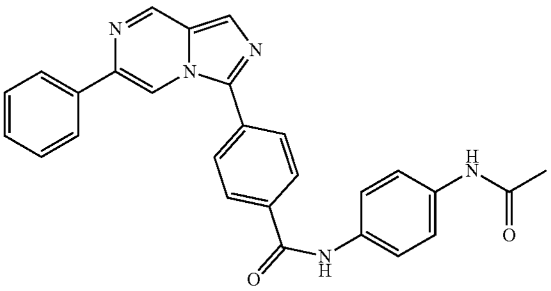 [SMILES: CC(=O)Nc1ccc(NC(=O)c2ccc(-c3ncc4cnc(-c5ccccc5)cn34)cc2)cc1]

A solution of 4-(6-phenylimidazo[1,5-a]pyrazin-3-yl) benzoic acid (0.05 g, 0.159 mmol) and HATU (0.066 g, 0.174 mmol) in DMF (0.5 ml) was treated with DIPEA (0.033 ml, 0.190 mmol). After 10 minutes N-(4-aminophenyl)acetamide (0.024 g, 0.159 mmol) was added to the solution. The solution was stirred at room temperature. After 18 h the solution was introduced into a 24 g silica gel column equilibrated with EtOAc. Elution was done with a gradient (EtOAc to 10% MeOH/EtOAc). Desired fractions were combined, concentrated and dried in vacuo to give the desired compound (0.04 g, 56%). (LCMS, ESI pos.) Calculated for $C_{27}H_{21}N_5O_2$: 448.5 (M+H), Measured: 448.2. $^1$H NMR (400 MHz, Chloroform-d) δ 9.10 (d, J=1.5 Hz, 1H), 8.41 (t, J=1.2 Hz, 1H), 7.93 (d, J=1.0 Hz, 1H), 7.87 (td, J=6.1, 2.8 Hz, 4H), 7.66-7.59 (m, 2H), 7.52-7.44 (m, 2H), 7.43-7.37 (m, 1H), 3.68 (s, 1H), 3.40 (d, J=10.2 Hz, 1H), 3.09 (d, J=29.0 Hz, 3H), 2.67-2.38 (m, 2H), 2.32 (s, 3H), 2.10 (s, 3H).

Figure 5:
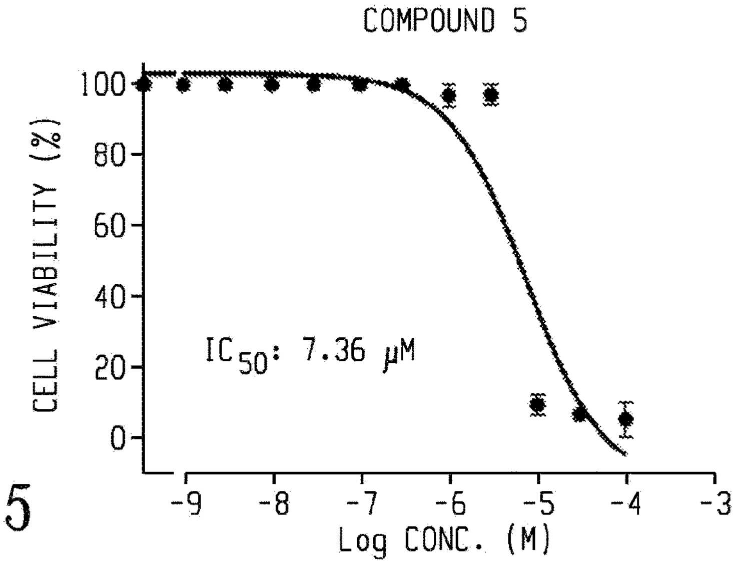
FIG. 5 shows a graph of Percentage Relative Cell Viability versus Log Molar Concentration illustrating macrophage activity of Compound 5 with IC50 of 7.36 μM

FIG. 5 shows IC50 of 7.36 μM for Compound 5.

Example 44

Synthesis of N-(3-(1H-imidazol-1-yl)propyl)-4-(6-phenylimidazo[1,5-a]pyrazin-3-yl)benzamide (Compound 6)

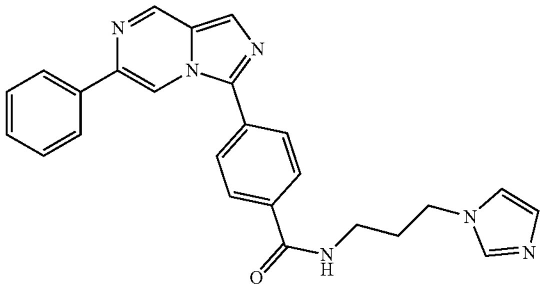 [SMILES: O=C(NCCCn1ccnc1)c1ccc(-c2ncc3cnc(-c4ccccc4)cn23)cc1]

A solution of 4-(6-phenylimidazo[1,5-a]pyrazin-3-yl) benzoic acid (0.05 g, 0.159 mmol) and HATU (0.066 g, 0.174 mmol) in DMF (0.5 ml) was treated with DIPEA (0.033 ml, 0.190 mmol). The solution was stirred for 15 minutes. To the solution was added 3-(1H-imidazol-1-yl) propan-1-amine (0.020 g, 0.159 mmol). The solution was stirred at room temperature. The solution was introduced into a 24 g silica gel column equilibrated with EtOAc. Elution was done with a gradient (EtOAc to 10% MeOH/EtOAc). Desired fractions were combined, concentrated and dried in vacuo to give the desired compound (0.03 g, 45%). (LCMS, ESI pos.) Calculated for $C_{25}H_{22}N_6O$: 423.5 (M+H), Measured: 423.1. $^1$H NMR (400 MHz, Chloroform-d) δ 9.11 (d, J=1.6 Hz, 1H), 8.43 (dd, J=1.6, 0.9 Hz, 1H), 7.93 (s, 5H), 7.89-7.83 (m, 2H), 7.51 (t, J=1.1 Hz, 1H), 7.50-7.43 (m, 2H), 7.43-7.37 (m, 1H), 7.06 (d, J=1.1 Hz, 1H), 6.98 (t, J=1.3 Hz, 1H), 6.60-6.49 (m, 1H), 4.09 (dt, J=11.4, 7.0 Hz, 2H), 3.51 (q, J=6.5 Hz, 2H), 2.15 (p, J=6.8 Hz, 2H).

Figure 6:
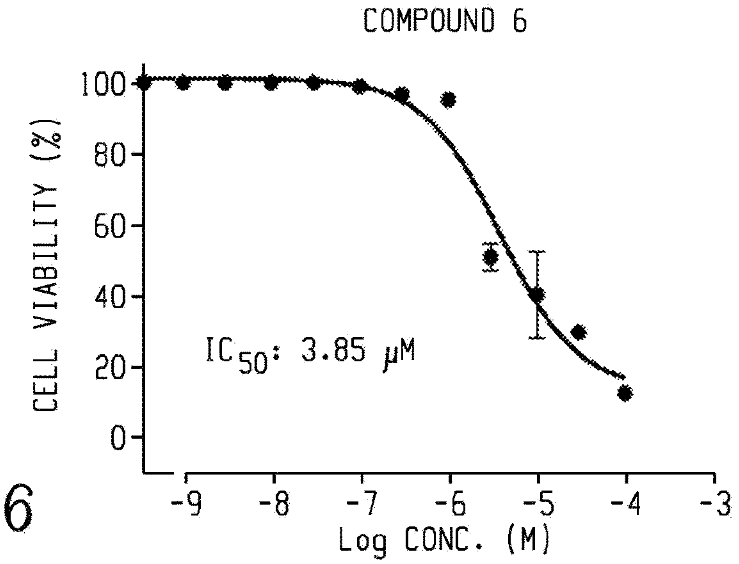
FIG. 6 shows a graph of Percentage Relative Cell Viability versus Log Molar Concentration illustrating macrophage activity of Compound 6 with IC50 of 3.85 μM.

FIG. 6 shows IC50 of 3.85 μM for Compound 6.

Example 45

Synthesis of N-(2-(dimethylamino)ethyl)-4-(6-phenylimidazo[1,5-a]pyrazin-3-yl)benzamide (Compound 7)

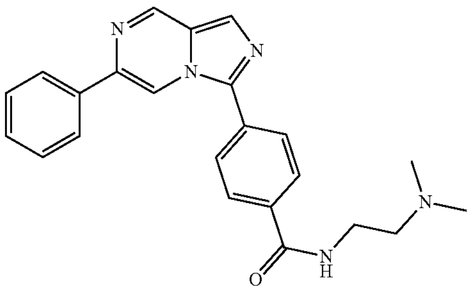 [SMILES: CN(C)CCNC(=O)c1ccc(-c2ncc3cnc(-c4ccccc4)cn23)cc1]

A solution of 4-(6-phenylimidazo[1,5-a]pyrazin-3-yl) benzoic acid (0.05 g, 0.159 mmol) and HATU (0.066 g, 0.174 mmol) in DMF (0.5 ml) was treated with DIPEA (0.033 ml, 0.190 mmol). To the solution was added N1,N1-dimethylethane-1,2-diamine (0.017 ml, 0.159 mmol). The solution was stirred at room temperature overnight. The solution was introduced into a 24 g silica gel column equilibrated with EtOAc. Elution was done with a gradient (EtOAc to 10% MeOH/EtOAc). Desired fractions were combined, concentrated and dried in vacuo to give the desired compound (0.045 g, 74%). (LCMS, ESI pos.) Calculated for $C_{23}H_{23}N_5O$: 386.5 (M+H), Measured: 385.9. $^1$H NMR (400 MHz, Chloroform-d) δ 9.11 (d, J=1.6 Hz, 1H), 8.44 (dd, J=1.7, 0.9 Hz, 1H), 8.00 (d, J=8.4 Hz, 2H), 7.96-7.91 (m, 3H), 7.90-7.85 (m, 2H), 7.50-7.44 (m, 2H), 7.44-7.37 (m, 1H), 6.96 (s, 1H), 3.61-3.51 (m, 2H), 2.54 (t, J=5.9 Hz, 2H), 2.28 (s, 6H).

Figure 7:
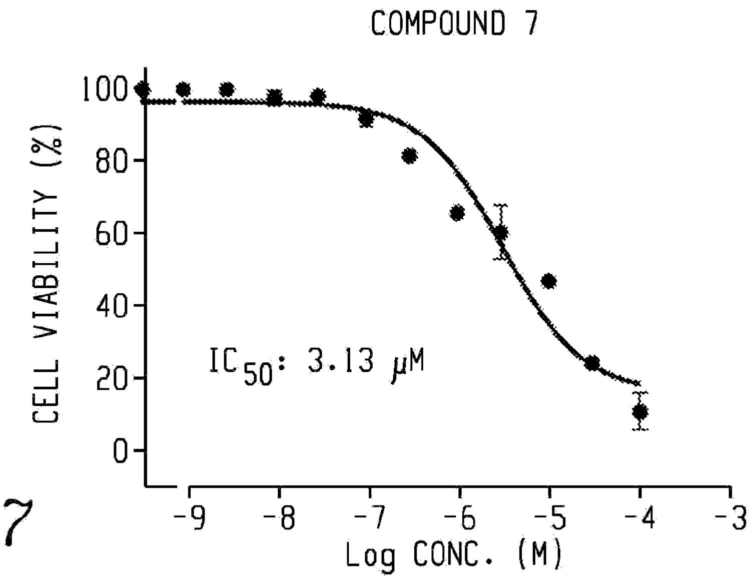
FIG. 7 shows a graph of Percentage Relative Cell Viability versus Log Molar Concentration illustrating macrophage activity of Compound 7 with IC50 of 3.13 μM.

FIG. 7 shows IC50 of 3.13 μM for Compound 7.

Example 46

Synthesis of 4-(6-phenylimidazo[1,5-a]pyrazin-3-yl)-N-(pyrazin-2-ylmethyl)benzamide (Compound 20)

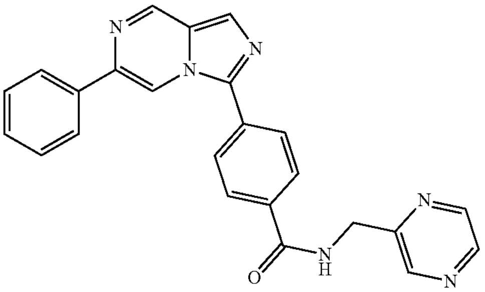 [SMILES: O=C(NCc1cnccn1)c1ccc(-c2ncc3cnc(-c4ccccc4)cn23)cc1]

A solution of 4-(6-phenylimidazo[1,5-a]pyrazin-3-yl) benzoic acid (0.05 g, 0.159 mmol) and HATU (0.066 g, 0.174 mmol) in DMF (0.5 ml) was treated with DIPEA (0.033 ml, 0.190 mmol). To the solution was added pyrazin-2-ylmethanamine (0.017 g, 0.159 mmol). The solution was stirred at room temperature for 18 h. The solution was introduced into a 24 g silica gel column equilibrated with EtOAc. Elution was done with a gradient (EtOAc to 10% MeOH/EtOAc). Desired fractions were combined, concentrated and dried in vacuo to give the desired compound (0.045 g, 74%). (LCMS, ESI pos.) Calculated for $C_{24}H_{18}N_6O$: 407.5 (M+H), Measured: 407.2. $^1$H NMR (400 MHz, Chloroform-d) δ 9.10 (d, J=1.6 Hz, 1H), 8.68 (d, J=1.5 Hz, 1H), 8.56-8.48 (m, 2H), 8.42 (t, J=1.3 Hz, 1H), 8.08-8.01 (m, 2H), 7.96-7.90 (m, 3H), 7.88-7.81 (m, 2H), 7.53 (t, J=5.3 Hz, 1H), 7.48-7.34 (m, 3H), 4.84 (d, J=5.1 Hz, 2H).

Example 47

Synthesis of 1-(4-(4-(6-phenylimidazo[1,5-a] pyrazin-3-yl)benzoyl)piperazin-1-yl)ethan-1-one (Compound 21)

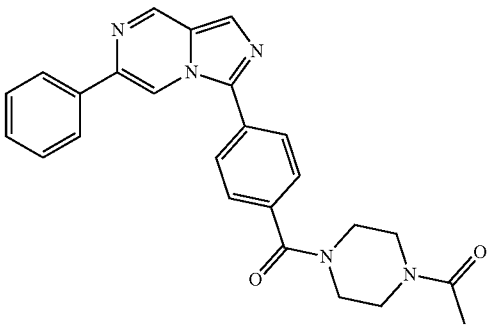 [SMILES: CC(=O)N1CCN(C(=O)c2ccc(-c3ncc4cnc(-c5ccccc5)cn34)cc2)CC1]

A solution of 4-(6-phenylimidazo[1,5-a]pyrazin-3-yl) benzoic acid (0.05 g, 0.159 mmol) and HATU (0.066 g, 0.174 mmol) in DMF (0.5 ml) was treated with 1-(piperazin-1-yl)ethan-1-one (0.020 g, 0.159 mmol). The solution was stirred at room temperature for 18 hrs. The solution was introduced into a 24 g silica gel column equilibrated with EtOAc. Elution was done with a gradient (EtOAc to 10% MeOH/EtOAc). Desired fractions were combined, concentrated and dried in vacuo to give the desired compound (0.045 g, 74%). (LCMS, ESI pos.) Calculated for $C_{25}H_{23}N_5O_2$: 426.5 (M+H), Measured: 426.1. $^1$H NMR (400 MHz, Chloroform-d) δ 9.12 (d, J=1.6 Hz, 1H), 8.49-8.36 (m, 1H), 7.96-7.90 (m, 3H), 7.90-7.84 (m, 2H), 7.65-7.60 (m, 2H), 7.51-7.44 (m, 2H), 7.44-7.38 (m, 1H), 3.93-3.33 (m, 8H), 2.13 (s, 3H).

Example 48

Synthesis of N-(2-methoxyethyl)-4-(6-phenylimidazo[1,5-a]pyrazin-3-yl)benzamide (Compound 22)

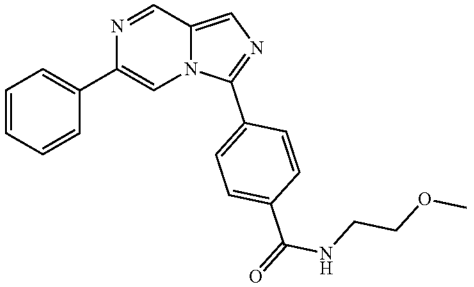 [SMILES: COCCNC(=O)c1ccc(-c2ncc3cnc(-c4ccccc4)cn23)cc1]

A solution of 4-(6-phenylimidazo[1,5-a]pyrazin-3-yl) benzoic acid (0.05 g, 0.159 mmol) and HATU (0.066 g, 0.174 mmol) in DMF (0.5 ml) was treated with DIPEA (0.033 ml, 0.190 mmol). The solution was stirred for 15 minutes. To the solution was added 2-methoxyethan-1-amine (0.014 ml, 0.159 mmol). The solution was stirred at room temperature for 18 hrs. The solution was introduced into a 24 g silica gel column equilibrated with EtOAc. Elution was done with a gradient (EtOAc to 10% MeOH/EtOAc). Desired fractions were combined, concentrated and dried in vacuo to give the desired compound (0.040 g, 68%). (LCMS, ESI pos.) Calculated for $C_{22}H_{20}N_4O_2$: 373.4 (M+H), Measured: 372.9. $^1$H NMR (400 MHz, Chloroform-d) δ 9.12 (d, J=1.6 Hz, 1H), 8.44 (t, J=1.2 Hz, 1H), 8.02-7.92 (m, 5H), 7.90-7.85 (m, 2H), 7.47 (dd, J=8.3, 6.5 Hz, 2H), 7.44-7.38 (m, 1H), 6.60 (s, 1H), 3.69 (q, J=5.2 Hz, 2H), 3.59 (t, J=5.0 Hz, 2H), 3.40 (s, 3H).

Example 49

Synthesis of N-methyl-1-(4-(6-phenylimidazo[1,5-a] pyrazin-3-yl)benzoyl)piperidine-4-carboxamide (Compound 23)

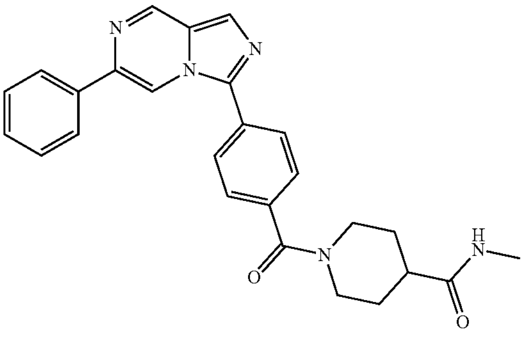 [SMILES: CNC(=O)C1CCN(C(=O)c2ccc(-c3ncc4cnc(-c5ccccc5)cn34)cc2)CC1]

A solution of 4-(6-phenylimidazo[1,5-a]pyrazin-3-yl) benzoic acid (0.05 g, 0.159 mmol) and HATU (0.066 g, 0.174 mmol) in DMF (0.5 ml) was treated with DIPEA (0.033 ml, 0.190 mmol). The solution was stirred at room temperature for 15 minutes. N-methylpiperidine-4-carboxamide (0.023 g, 0.159 mmol) was added to the solution. The reaction solution was stirred at room temperature for 18 hrs. The solution was introduced into a 24 g silica gel column equilibrated with EtOAc. Elution was done with a gradient (EtOAc to 10% MeOH/EtOAc). Desired fractions were combined, concentrated and dried in vacuo to give the desired compound (0.033 g, 47%). (LCMS, ESI pos.) Calculated for $C_{26}H_{25}N_5O_2$: 440.5 (M+H), Measured: 439.9. $^1$H NMR (400 MHz, Chloroform-d) δ 9.08 (d, J=1.5 Hz, 1H), 8.39 (p, J=0.7 Hz, 1H), 7.90 (d, J=0.9 Hz, 1H), 7.88-7.80 (m, 4H), 7.61-7.52 (m, 2H), 7.44 (dd, J=8.3, 6.5 Hz, 2H), 7.41-7.34 (m, 1H), 5.84 (q, J=4.9 Hz, 1H), 4.67 (s, 1H), 3.84 (s, 1H), 3.17-2.81 (m, 2H), 2.78 (d, J=4.8 Hz, 3H), 2.35 (tt, J=11.1, 4.1 Hz, 1H), 1.83 (d, J=51.1 Hz, 4H).

Example 50

Synthesis of N-(4-hydroxycyclohexyl)-4-(6-phenylimidazo[1,5-a]pyrazin-3-yl)benzamide (Compound 24)

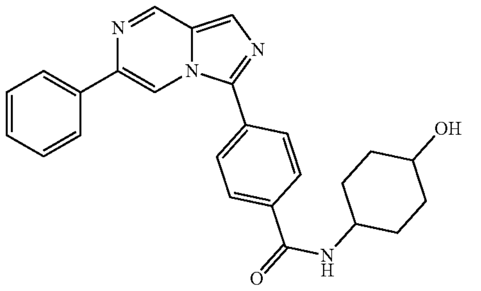 [SMILES: O=C(NC1CCC(O)CC1)c1ccc(-c2ncc3cnc(-c4ccccc4)cn23)cc1]

A solution of 4-(6-phenylimidazo[1,5-a]pyrazin-3-yl) benzoic acid (0.05 g, 0.159 mmol) and HATU (0.066 g, 0.174 mmol) in DMF (0.5 ml) was treated with DIPEA (0.033 ml, 0.190 mmol). The solution was stirred at room temperature. After 10 minutes 4-aminocyclohexan-1-ol (0.018 g, 0.159 mmol) was added. The solution was stirred at room temperature for 18 hrs. The solution was introduced into a 24 g silica gel column equilibrated with EtOAc. Elution was done with a gradient (EtOAc to 10% MeOH/EtOAc). Desired fractions were combined, concentrated and dried in vacuo to give the desired compound (0.032 g, 49%). (LCMS, ESI pos.) Calculated for $C_{25}H_{24}N_4O_2$: 413.5 (M+H), Measured: 412.9. $^1$H NMR (400 MHz, Chloroform-d) δ 9.11 (d, J=1.6 Hz, 1H), 8.42 (t, J=1.3 Hz, 1H), 7.94 (dd, J=3.4, 1.1 Hz, 5H), 7.89-7.83 (m, 2H), 7.50-7.43 (m, 2H), 7.43-7.37 (m, 1H), 6.00 (d, J=7.9 Hz, 1H), 4.00 (tdt, J=11.5, 8.0, 4.1 Hz, 1H), 3.66 (tt, J=10.3, 4.1 Hz, 1H), 2.22-2.10 (m, 2H), 2.04 (dd, J=12.0, 3.8 Hz, 2H), 1.58-1.41 (m, 2H), 1.34 (qd, J=12.8, 3.1 Hz, 2H).

Example 51

Synthesis of 4-(6-(3-fluorophenyl)imidazo[1,5-a]pyrazin-3-yl)-N-(3-(2-oxopyrrolidin-1-yl)propyl) benzamide (Compound 29)

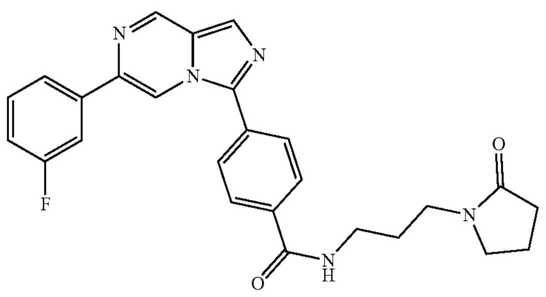 [SMILES: O=C(NCCCN1CCCC1=O)c1ccc(-c2ncc3cnc(-c4cccc(F)c4)cn23)cc1]

A mixture of 4-(6-(3-fluorophenyl)imidazo[1,5-a]pyrazin-3-yl)benzoic acid (0.022 g, 0.066 mmol) and HATU (0.028 g, 0.073 mmol) in DMF (0.220 ml) was treated with DIPEA (0.014 ml, 0.079 mmol). The solution was stirred at room temperature. After 10 min 1-(3-aminopropyl)pyrrolidin-2-one (9.39 mg, 0.066 mmol) was added. The solution was stirred at room temperature. The solution was stirred at room temperature for 3 hrs. The solution was introduced into a 24 g silica gel column equilibrated with EtOAc. Elution was done with a gradient (EtOAc to 10% MeOH/EtOAc). Desired fractions were combined, concentrated and dried in vacuo to give the desired compound (0.007 g, 23%). (LCMS, ESI pos.) Calculated for $C_{26}H_{24}FN_5O_2$: 458.5 (M+H), Measured: 458.1. $^1$H NMR (400 MHz, Chloroform-d) δ 9.11 (d, J=1.6 Hz, 1H), 8.46 (t, J=1.3 Hz, 1H), 8.24-8.14 (m, 2H), 8.06 (t, J=6.4 Hz, 1H), 8.02-7.91 (m, 3H), 7.72-7.60 (m, 2H), 7.43 (td, J=8.2, 5.9 Hz, 1H), 7.10 (tdd, J=8.3, 2.6, 1.0 Hz, 1H), 3.46 (ddt, J=9.2, 6.1, 2.9 Hz, 6H), 2.57-2.42 (m, 2H), 2.23-2.05 (m, 2H), 1.90-1.77 (m, 2H).

Example 52

Synthesis of 4-(6-(3-fluorophenyl)imidazo[1,5-a]pyrazin-3-yl)benzamide (Compound 8)

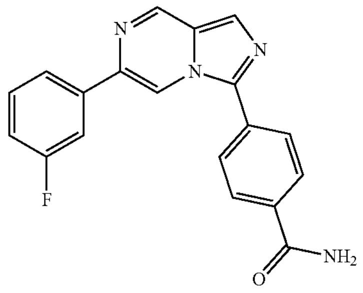 [SMILES: NC(=O)c1ccc(-c2ncc3cnc(-c4cccc(F)c4)cn23)cc1]

A mixture of 4-(6-(3-fluorophenyl)imidazo[1,5-a]pyrazin-3-yl)benzoic acid (0.02 g, 0.060 mmol) and HATU (0.025 g, 0.066 mmol) in DMF (0.200 ml) was treated with DIPEA (0.013 ml, 0.072 mmol). The solution was stirred at room temperature for 10 min. To the solution was added ammonia (8.57 μl, 0.060 mmol). The solution was stirred at room temperature for 18 hrs. The solution was filtered. The solid was triturated with EtOAc/MeOH 1:1. The solution was decanted. The solid was dried in vacuo to give desired compound (7.7 mg, 39%). (LCMS, ESI pos.) Calculated for $C_{19}H_{13}FN_4O$: 333.3 (M+H), Measured: 333.1. $^1$H NMR (400 MHz, Chloroform-d) δ 8.96 (t, J=1.2 Hz, 1H), 8.38 (d, J=1.5 Hz, 1H), 7.90 (d, J=8.1 Hz, 2H), 7.82 (d, J=1.0 Hz, 1H), 7.74 (d, J=8.1 Hz, 1H), 7.70 (d, J=5.7 Hz), 7.53-7.47 (m, 2H), 7.20 (td, J=7.9, 5.8 Hz, 1H), 6.91-6.82 (m, 1H), 6.76 (s, 1H).

Figure 20:
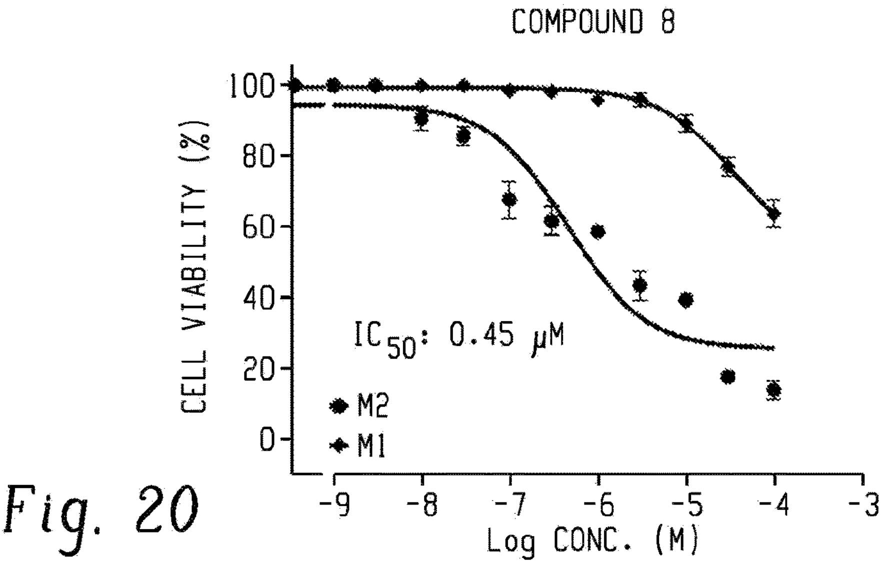
FIG. 20 shows a graph of Percentage Relative Cell Viability versus Log Molar Concentration illustrating macrophage activity of Compound 8 with IC50 of 0.45 μM.

FIG. 20 shows IC50 of 0.45 μM for Compound 8.

Example 53

Synthesis of N-(3-(1H-imidazol-1-yl)propyl)-4-(6-(3-fluorophenyl)imidazo[1,5-a]pyrazin-3-yl)benzamide (Compound 25)

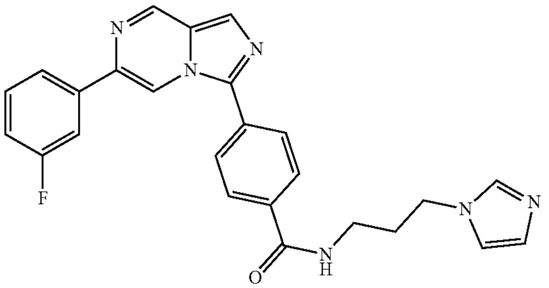 [SMILES: O=C(NCCCn1ccnc1)c1ccc(-c2ncc3cnc(-c4cccc(F)c4)cn23)cc1]

A solution of 4-(6-(3-fluorophenyl)imidazo[1,5-a]pyrazin-3-yl)benzoic acid (0.02 g, 0.060 mmol) and HATU (0.025 g, 0.066 mmol) in DMF (0.200 ml) was treated with DIPEA (0.013 ml, 0.072 mmol). The solution was stirred at room temperature for 10 min. To the solution was added 3-(1H-imidazol-1-yl)propan-1-amine (7.51 mg, 0.060 mmol). The solution was stirred at room temperature for 18 hrs. The solution was introduced into a 24 g silica gel column equilibrated with EtOAc. Elution was done with a gradient (EtOAc to 10% MeOH/EtOAc). Desired fractions were combined, concentrated and dried in vacuo to give the desired compound (0.005 g, 19%). (LCMS, ESI pos.) Calculated for $C_{25}H_{21}FN_6O$: 441.5 (M+H), Measured: 441.1. $^1H$ NMR (400 MHz, Chloroform-d) δ 9.08 (t, J=1.2 Hz, 1H), 8.40 (dt, J=1.6, 1.0 Hz, 1H), 8.02 (dd, J=7.5, 1.3 Hz, 2H), 7.99-7.85 (m, 4H), 7.78 (s, 1H), 7.61 (dt, J=8.8, 1.6 Hz, 2H), 7.48-7.36 (m, 1H), 7.09 (tdd, J=6.4, 2.9, 1.5 Hz, 2H), 7.01 (s, 1H), 4.20-4.05 (m, 2H), 3.51 (q, J=6.4 Hz, 2H), 2.18 (p, J=6.6 Hz, 2H).

Example 54

Synthesis of 4-(6-(3-fluorophenyl)imidazo[1,5-a]pyrazin-3-yl)-N-(2-methoxyethyl)benzamide (Compound 13)

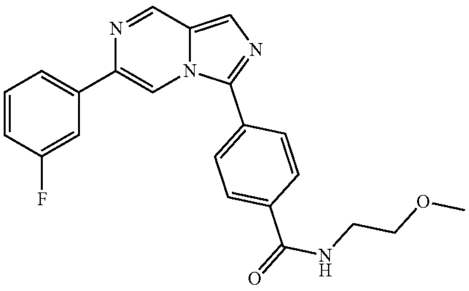 [SMILES: COCCNC(=O)c1ccc(-c2ncc3cnc(-c4cccc(F)c4)cn23)cc1]

A solution of 4-(6-(3-fluorophenyl)imidazo[1,5-a]pyrazin-3-yl)benzoic acid (0.02 g, 0.060 mmol) and HATU (0.025 g, 0.066 mmol) in DMF (0.200 ml) was treated with DIPEA (0.013 ml, 0.072 mmol). The solution was stirred at room temperature for 10 min. To the solution was added 2-methoxyethan-1-amine (5.22 μl, 0.060 mmol). The solution was stirred at room temperature for 18 hrs. The solution was introduced into a 24 g silica gel column equilibrated with EtOAc. Elution was done with a gradient (EtOAc to 10% MeOH/EtOAc). Desired fractions were combined, concentrated and dried in vacuo to give the desired compound (0.009 g, 39%). (LCMS, ESI pos.) Calculated for $C_{22}H_{19}FN_4O_2$: 391.4 (M+H), Measured: 391.2. $^1H$ NMR (400 MHz, Chloroform-d) δ 9.12 (d, J=1.6 Hz, 1H), 8.44 (dd, J=1.6, 1.0 Hz, 1H), 8.04-7.97 (m, 3H), 7.97-7.88 (m, 2H), 7.67-7.59 (m, 2H), 7.43 (td, J=8.2, 6.0 Hz, 1H), 7.16-7.05 (m, 1H), 6.60 (s, 1H), 3.69 (td, J=5.6, 4.3 Hz, 2H), 3.63-3.55 (m, 2H), 3.40 (d, J=0.9 Hz, 3H).

Example 55

Synthesis of 4-(6-(3-fluorophenyl)imidazo[1,5-a]pyrazin-3-yl)-N-(3-hydroxypropyl)benzamide (Compound 9)

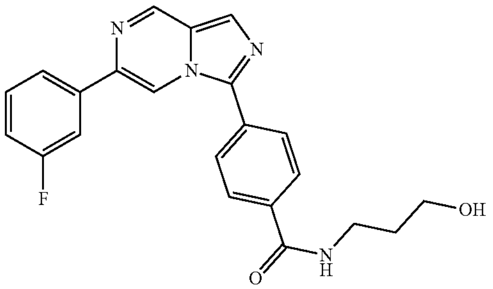 [SMILES: O=C(NCCCO)c1ccc(-c2ncc3cnc(-c4cccc(F)c4)cn23)cc1]

A mixture of 4-(6-(3-fluorophenyl)imidazo[1,5-a]pyrazin-3-yl)benzoic acid (0.02 g, 0.060 mmol) and HATU (0.025 g, 0.066 mmol) in DMF (0.200 ml) was treated with DIPEA (0.013 ml, 0.072 mmol). The solution was stirred at room temperature for 10 min. To the solution was added 3-aminopropan-1-ol (4.56 μl, 0.060 mmol). The solution was stirred at room temperature for 18 hrs. The solution was introduced into a 24 g silica gel column equilibrated with EtOAc. Elution was done with a gradient (EtOAc to 10% MeOH/EtOAc). Desired fractions were combined, concentrated and dried in vacuo to give the desired compound (0.002 g, 9%). (LCMS, ESI pos.) Calculated for $C_{22}H_{19}FN_4O_2$: 391.4 (M+H), Measured: 391.2. $^1H$ NMR (400 MHz, Chloroform-d) δ 9.14 (d, J=1.6 Hz, 1H), 8.43 (t, J=1.3 Hz, 1H), 8.04-7.97 (m, 3H), 7.97-7.89 (m, 2H), 7.68-7.59 (m, 2H), 7.43 (td, J=8.2, 5.9 Hz, 1H), 7.15-7.06 (m, 1H), 6.96 (d, J=10.7 Hz, 1H), 3.78 (t, J=5.5 Hz, 2H), 3.68 (q, J=6.0 Hz, 2H), 1.85 (p, J=5.6 Hz, 2H).

Figure 21:
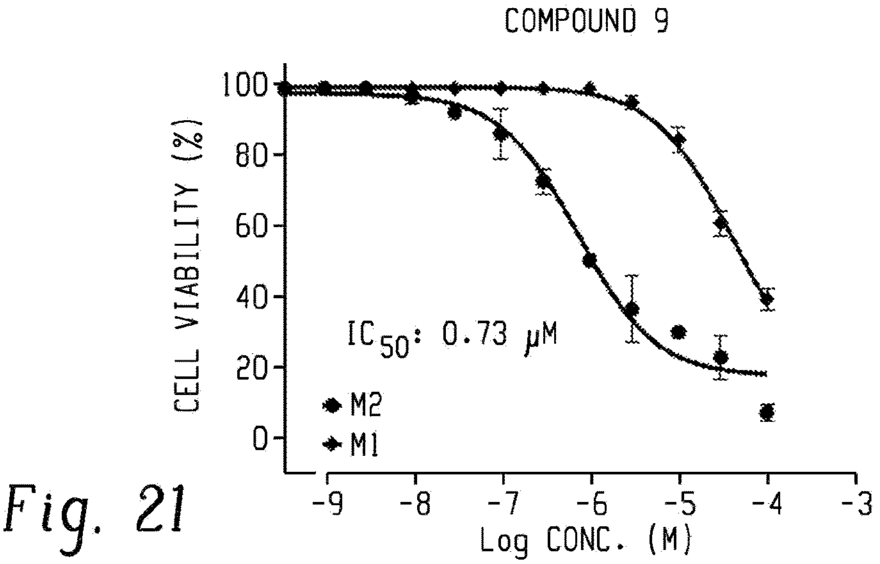
FIG. 21 shows a graph of Percentage Relative Cell Viability versus Log Molar Concentration illustrating macrophage activity of Compound 9 with IC50 of 0.73 μM.

FIG. 21 shows IC50 of 0.73 μM for Compound 9.

Example 56

Synthesis of tert-butyl (3-(4-(6-(3-fluorophenyl)imidazo[1,5-a]pyrazin-3-yl)benzamido)propyl)carbamate (Compound 12)

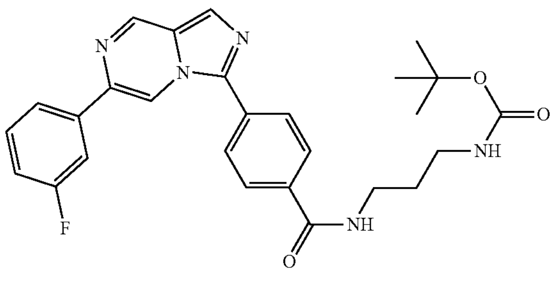 [SMILES: CC(C)(C)OC(=O)NCCCNC(=O)c1ccc(-c2ncc3cnc(-c4cccc(F)c4)cn23)cc1]

A mixture of 4-(6-(3-fluorophenyl)imidazo[1,5-a]pyrazin-3-yl)benzoic acid (0.02 g, 0.060 mmol) and HATU (0.025 g, 0.066 mmol) in DMF (0.200 ml) was treated with DIPEA (0.013 ml, 0.072 mmol). The solution was stirred at room temperature for 10 min. To the solution was added tert-butyl (3-aminopropyl)carbamate (10.45 mg, 0.060 mmol). The solution was stirred at room temperature for 18 hrs. The solution was introduced into a 24 g silica gel column equilibrated with EtOAc. Elution was done with a gradient (EtOAc to 10% MeOH/EtOAc). Desired fractions were combined, concentrated and dried in vacuo to give the desired compound (0.002 g, 7%). (LCMS, ESI pos.) Calculated for $C_{27}H_{28}FN_5O_3$: 490.6 (M+H), Measured: 490.3. $^1H$ NMR (400 MHz, Chloroform-d) δ 9.10 (d, J=1.6 Hz, 1H), 8.45 (t, J=1.3 Hz, 1H), 8.08 (d, J=8.1 Hz, 2H), 7.97-7.90 (m, 3H), 7.68-7.61 (m, 2H), 7.51 (d, J=12.0 Hz, 1H), 7.42 (td, J=8.2, 6.0 Hz, 1H), 7.09 (tdd, J=8.3, 2.5, 1.1 Hz, 1H), 4.86 (s, 1H), 3.54 (q, J=6.1 Hz, 2H), 3.28 (q, J=6.4 Hz, 2H), 1.74 (p, J=6.1 Hz, 2H), 1.45 (s, 9H).

Example 57

Synthesis of N-(2-acetamidoethyl)-4-(6-(3-fluorophenyl)imidazo[1,5-a]pyrazin-3-yl)benzamide (Compound 10)

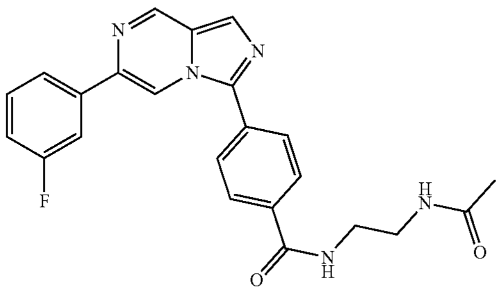 [SMILES: CC(=O)NCCNC(=O)c1ccc(-c2ncc3cnc(-c4cccc(F)c4)cn23)cc1]

A solution of 4-(6-(3-fluorophenyl)imidazo[1,5-a]pyrazin-3-yl)benzoic acid (0.02 g, 0.060 mmol) and HATU (0.025 g, 0.066 mmol) in DMF (0.200 ml) was treated with DIPEA (0.013 ml, 0.072 mmol). The solution was stirred at room temperature. After 10 min the solution was treated with N-(2-aminoethyl)acetamide (6.13 mg, 0.060 mmol). The solution was stirred at room temperature. The solution was filtered. The solid was triturated with EtOAc/MeOH 1:1. The solution was decanted. The solid was dried in vacuo to give desired compound (2.4 mg, 10%). (LCMS, ESI pos.) Calculated for $C_{23}H_{20}FN_5O_2$: 418.4 (M+H), Measured: 417.8. $^1H$ NMR (400 MHz, Chloroform-d) δ 9.19 (d, J=1.5 Hz, 1H), 8.43-8.39 (m, 1H), 8.26 (s, 1H), 8.11-8.05 (m, 2H), 7.90 (d, J=8.1 Hz, 2H), 7.64-7.52 (m, 3H), 7.40-7.33 (m, 1H), 7.04 (td, J=8.4, 2.2 Hz, 1H), 3.51 (d, J=5.7 Hz, 2H), 3.39 (d, J=8.1 Hz, 2H), 1.96-1.91 (m, 3H).

Figure 22:
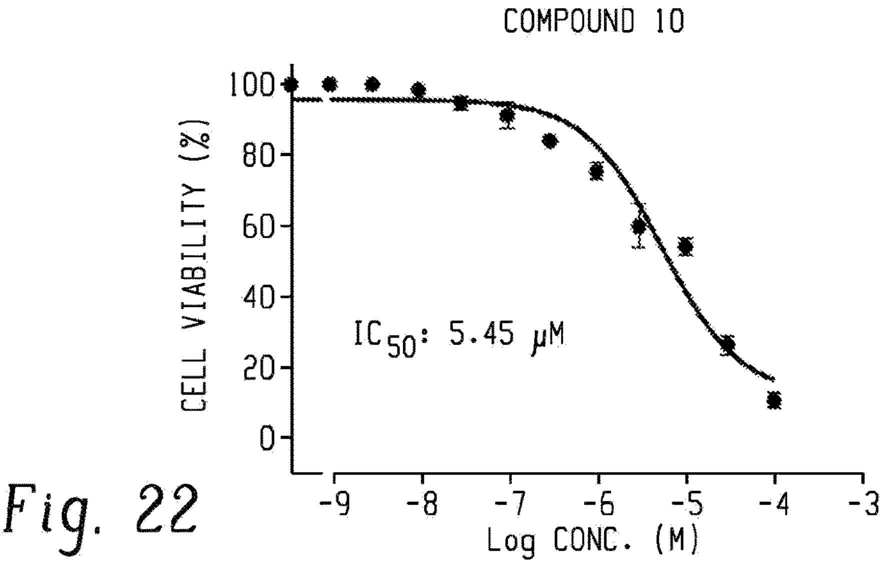
FIG. 22 shows a graph of Percentage Relative Cell Viability versus Log Molar Concentration illustrating macrophage activity of Compound 10 with IC50 of 5.45 μM.

FIG. 22 shows IC50 of 5.45 μM for Compound 10.

Example 58

Synthesis of N-(2-(1H-imidazol-5-yl)ethyl)-4-(6-(3-fluorophenyl)imidazo[1,5-a]pyrazin-3-yl)benzamide (Compound 11)

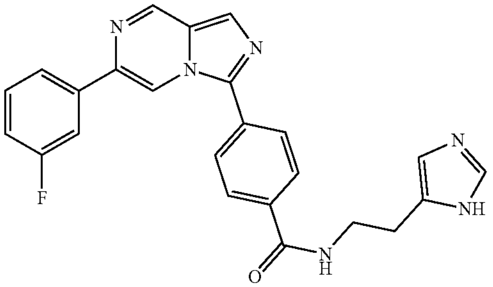 [SMILES: O=C(NCCc1cnc[nH]1)c1ccc(-c2ncc3cnc(-c4cccc(F)c4)cn23)cc1]

A mixture of 4-(6-(3-fluorophenyl)imidazo[1,5-a]pyrazin-3-yl)benzoic acid (0.04 g, 0.120 mmol) and HATU (0.050 g, 0.132 mmol) in DMF (0.400 ml) was treated with DIPEA (0.025 ml, 0.144 mmol). The solution was stirred at room temperature for 10 min. To the solution was added 2-(1H-imidazol-5-yl)ethan-1-amine (0.013 g, 0.120 mmol). The solution was stirred at room temperature for 18 hrs. The solution was introduced into a 24 g silica gel column equilibrated with EtOAc. Elution was done with a gradient (EtOAc to 10% MeOH/EtOAc). Desired fractions were combined, concentrated and dried in vacuo to give the desired compound (0.005 g, 10%). (LCMS, ESI pos.) Calculated for $C_{24}H_{19}FN_6O$: 427.5 (M+H), Measured: 427.1. $^1H$ NMR (400 MHz, Chloroform-d) δ 9.33 (d, J=1.5 Hz, 1H), 8.87 (t, J=1.3 Hz, 1H), 8.78 (t, J=5.6 Hz, 1H), 8.52 (dd, J=4.3, 1.4 Hz, 1H), 8.34 (dd, J=8.4, 1.4 Hz, 1H), 8.18-8.06 (m, 4H), 8.01-7.93 (m, 1H), 7.66 (d, J=1.3 Hz, 1H), 7.57 (td, J=8.2, 6.2 Hz, 1H), 7.34 (dd, J=8.4, 4.3 Hz, 1H), 7.29 (ddd, J=10.4, 8.1, 2.6 Hz, 1H), 6.91 (s, 1H), 3.58 (td, J=7.4, 5.5 Hz, 1H), 2.84 (t, J=7.4 Hz, 1H).

Example 59. Enzymatic Assays

Assays were conducted in a 96-well black solid-bottom plate with a final assay volume of 100 μL. As shown in Table 2, Compounds 1-3 show IC50 values that activate CD206 and selectively target M2 macrophages.

TABLE 2

| Compound | $IC_{50}$ (μM) | M2 Selectivity | |
|---|---|---|---|
| 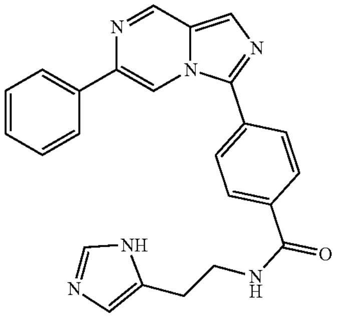 Compound 1 | 2.86 | Yes | (LCMS, ESI pos.) Calculated for $C_{24}H_{20}N_6O$: 409.5 (M + H), Measured: 409.2 $^1H$ NMR (400 MHz, DMSO-$d_6$) δ 11.87 (s, 1H), 9.33 (d, J = 1.5 Hz, 1H), 8.84-8.71 (m, 2H), 8.22-8.03 (m, 7H), 7.69-7.40 (m, 4H), 6.90 (s, 1H), 3.57 (td, J = 7.5, 5.5 Hz, 2H), 2.83 (s, 2H). |
| 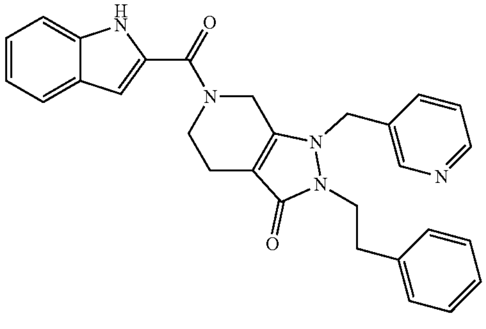 Compound 2 | 4.591 | Yes | LCMS, ESI pos.) Calculated for $C_{29}H_{27}N_5O_2$: 478.6 (M + H), Measured: 478.1 $^1H$ NMR (400 MHz, DMSO-d6) δ 11.71 (d, J = 2.0 Hz, 1H), 8.52 (dd, J = 4.6, 1.3 Hz, 1H), 8.47 (s, 1H), 7.68 (dq, 7 = 8.0, 0.8 Hz, 1H), 7.56 (s, 1H), 7.48 (dq, J = 8.3, 0.9 Hz, 1H), 7.37-7.16 (m, 7H), 7.11 (ddd, J = 8.0, 7.0, 1.0 Hz, 1H), 6.98-6.91 (m, 1H), 4.99 (s, 2H), 4.86 (s, 3H), 3.93 (dd, J = 16.7, 9.1 Hz, 5H), 2.77-2.67 (m, 1H), 2.43-2.31 (m, 1H). |
| 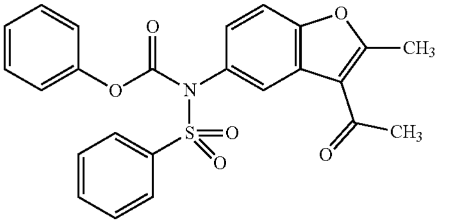 Compound 3 | 3.879 | Yes | (LCMS, ESI pos.) Calculated for $C_{24}H_{19}NO_6S$: 450.5 (M + H), Measured: 450.0 $^1H$ NMR (400 MHz, DMSO-d6) δ 8.12 (d, J = 2.2 Hz, 1H), 8.10-8.03 (m, 2H), 7.93-7.85 (m, 1H), 7.84-7.73 (m, 3H), 7.55 (dd, J = 8.7, 2.3 Hz, 1H), 7.39 (dd, J = 8.5, 7.2 Hz, 2H), 7.32-7.25 (m, 1H), 7.09-7.02 (m, 2H), 2.87 (s, 3H), 2.67 (s, 3H). |

Figure 1B:
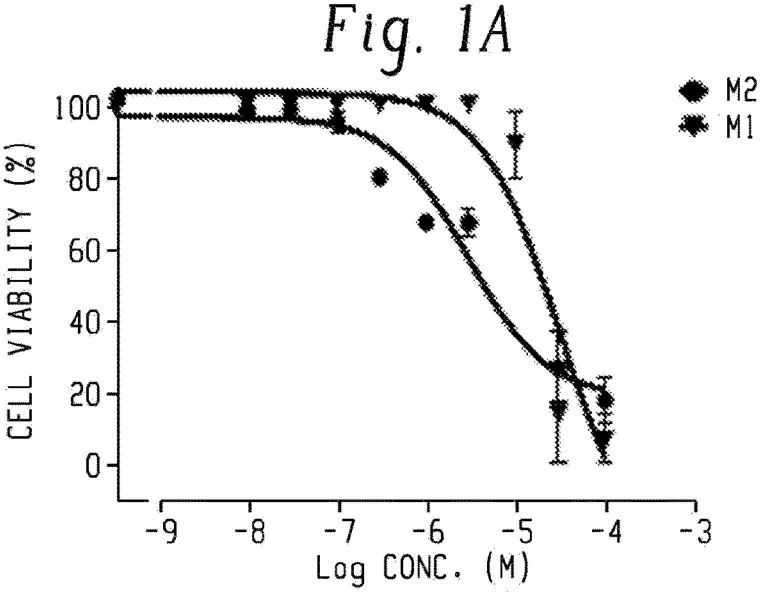
FIG. 1B shows a graph of Percentage Relative Cell Viability versus Log Molar Concentration illustrating anti-cell viability screening for Compound 2.
Figure 1C:
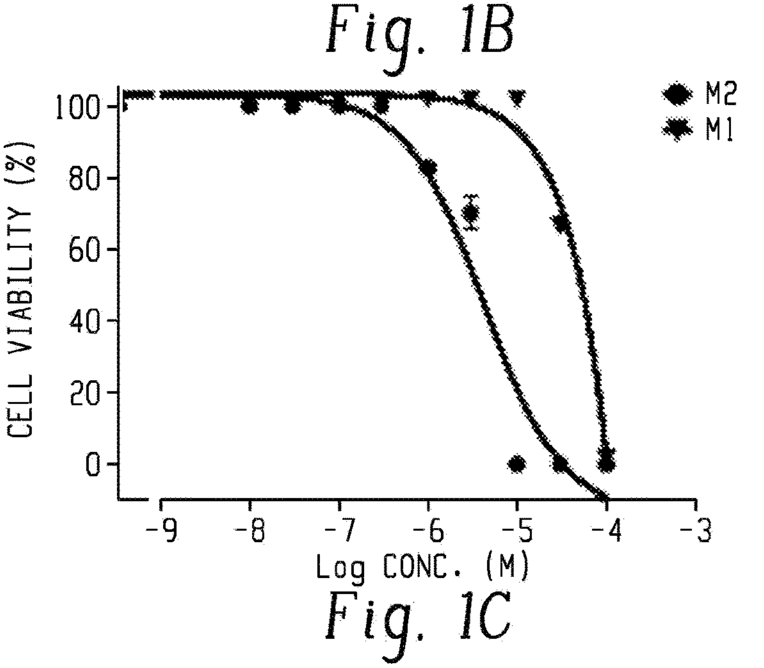
FIG. 1C shows a graph of Percentage Relative Cell Viability versus Log Molar Concentration illustrating anti-cell viability screening for Compound 3.

FIG. 1A-1C shows a graph of Percentage Relative Cell Viability versus Log Molar Concentration illustrating the selective anti-M2 macrophage activity determined by reduction of M2 macrophage cell viability for Compound 1-3 respectively.

Figure 11A:
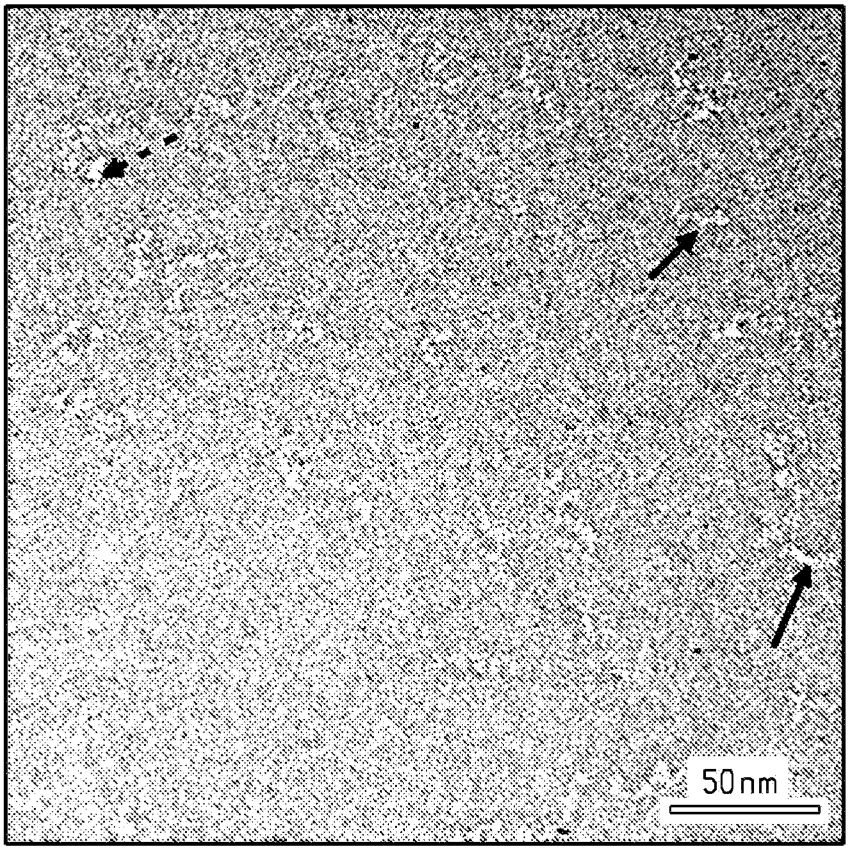
FIG. 11A shows a representative Electron microscopy image of recombinant human CD206 protein (UniProt ID P22897-1 NCBI ID: NP_002429.1) incubated with vehicle versus Compound 1 for 30 minutes at 1 micromolar (μM) illustrating that Example 38 induces the closed conformation of the CD206 receptor (solid arrow indicates open conformation of the CD206 receptor; dotted arrow indicates closed conformation)
Figure 11B:
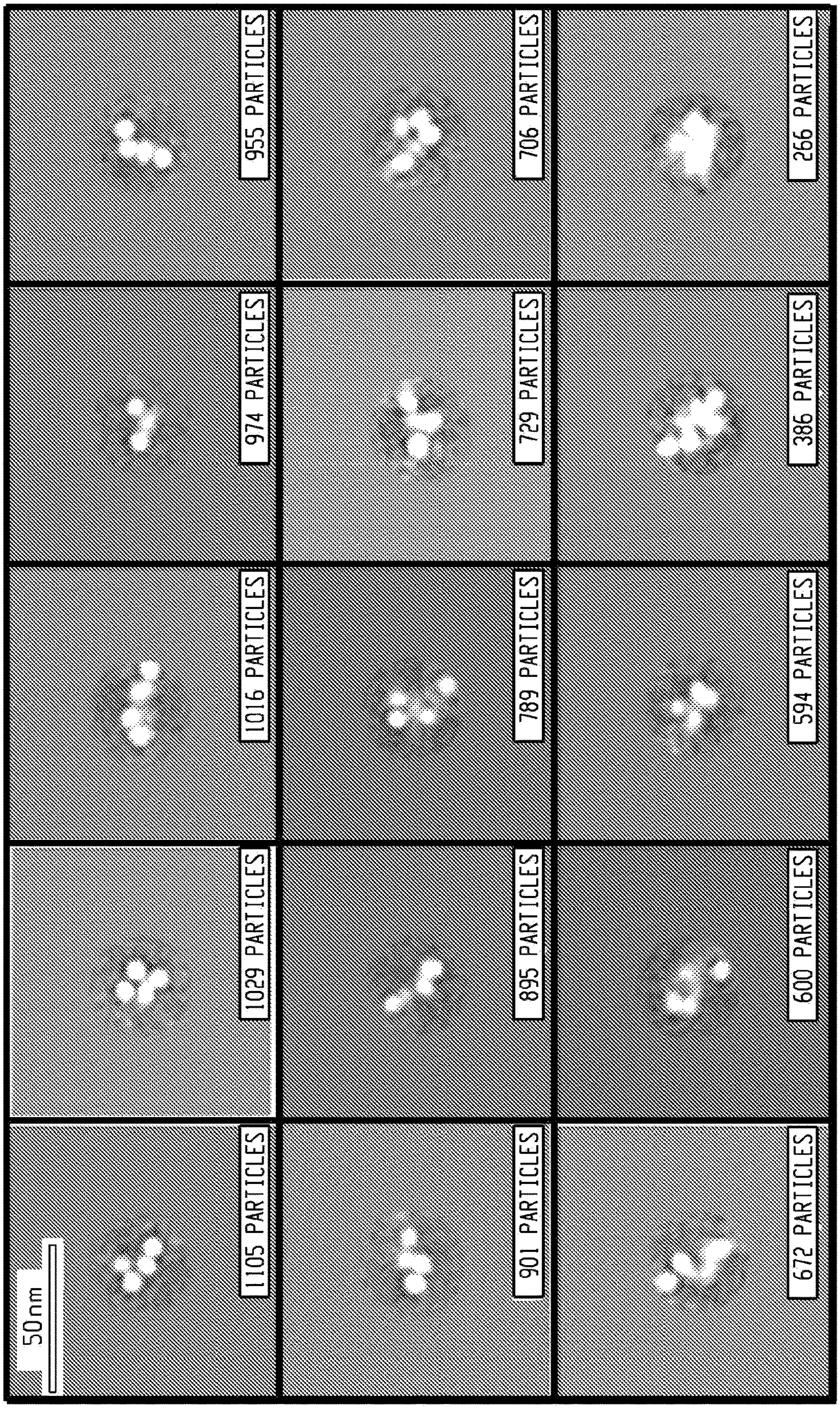
FIG. 11B shows a representative sequential series of scanned Electron microscopy images of recombinant CD206 incubated with vehicle versus Compound 1 for 30 minutes at 1 μM scored as closed versus open. The number of CD206 particles within a series were scored as closed vs open as indicated on the bottom, showing in summary that 48% of the CD206 particles are in a closed state (thick bordered square) and 52% are in open state (borderless squares) illustrating that Compound 1 binds to CD206 and induces a conformational switch of the receptor.
Figure 12A:
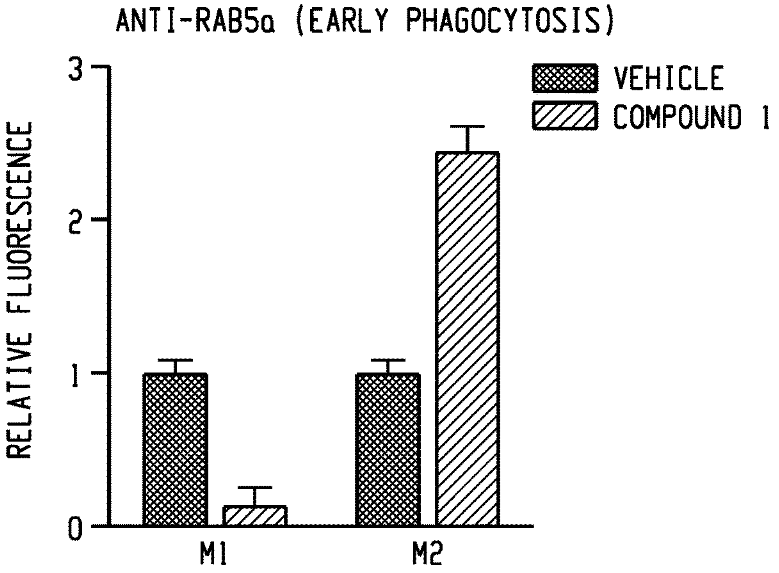
FIG. 12A shows graph of quantitative relative fluorescence obtained in murine M1 macrophages and M2 macrophages to indicate induction of early phagocytosis, illustrating that Compound 1 induces early phagocytosis in M2 but not in M1 macrophages.
Figure 12B:
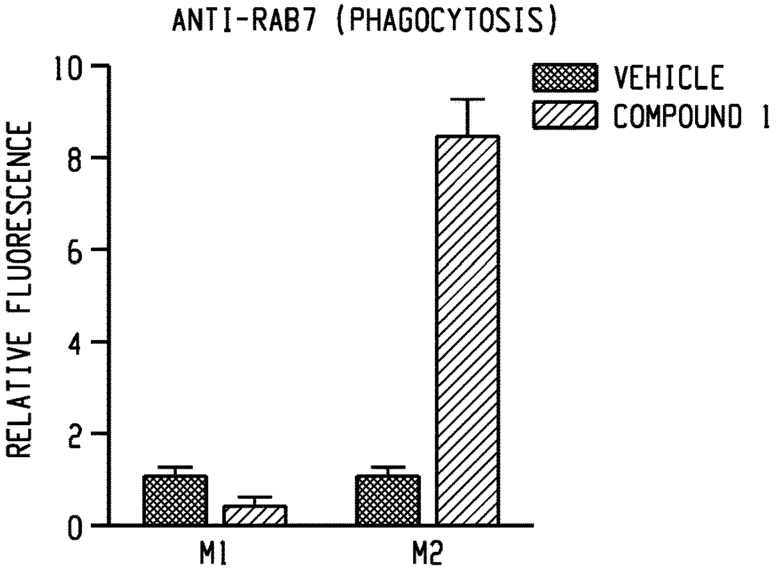
FIG. 12B shows graph of quantitative relative fluorescence obtained in murine M1 macrophages and M2 macrophages to indicate induction of phagocytosis, illustrating that Compound 1 induces phagocytosis in M2 but not in M1 macrophages.
Figure 12C:
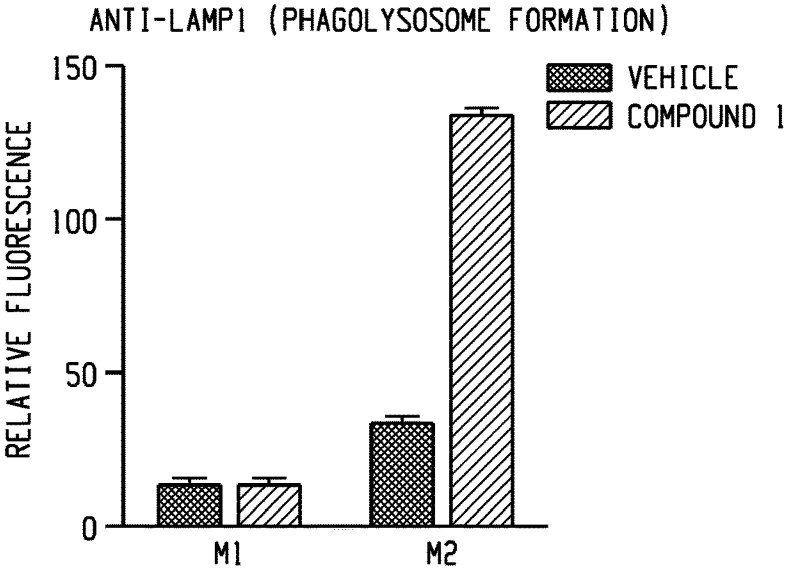
FIG. 12C shows graph of quantitive relative fluorescence obtained in murine M1 macrophages and M2 macrophages to indicate induction of phagolysosome formation, illustrating that Compound 1 induces phagolysosome formation in M2 but not in M1 macrophages.
Figure 12D:
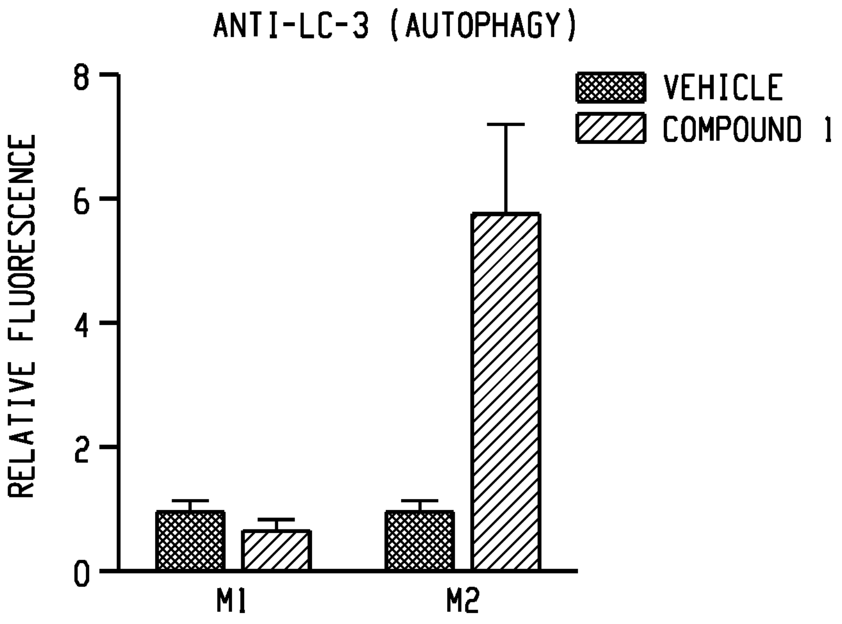
FIG. 12D shows graph of quantitive relative fluorescence obtained in murine M1 macrophages and M2 macrophages to indicate induction of autophagy, illustrating that Compound 1 induces autophagy in M2 but not in M1 macrophages.
Figure 12E:
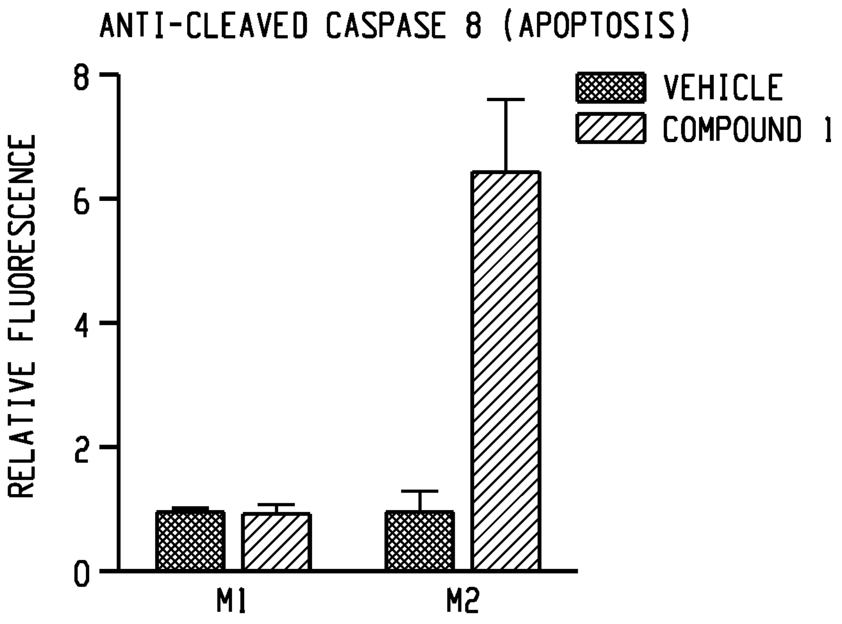
FIG. 12E shows graph of quantitive relative fluorescence obtained in murine M1 macrophages and M2 macrophages to indicate induction of apoptosis illustrating that Compound 1 induces apoptosis in M2 but not in M1 macrophages.

When recombinant CD206 was incubated with Compound 1 the electron microscopy studies showed that Compound 1 binds to CD206 and induces a conformational switch of the receptor. FIGS. 11A and 11B illustrate conformational change on CD206 when incubated with Compound 1.

Figure 2A:
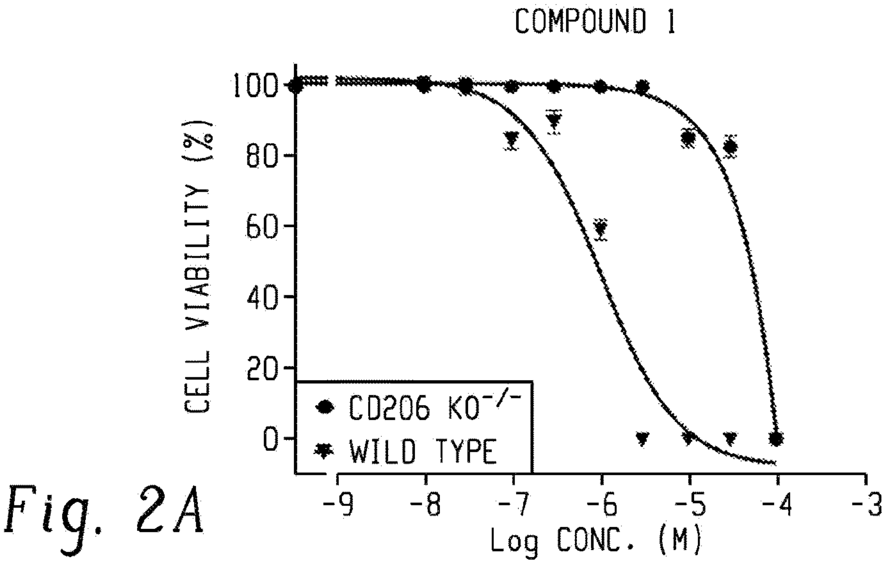
FIG. 2A is a graph of Percentage Relative Cell Viability versus Log Molar Concentration showing cell viabilities in M2 polarized macrophages with intact CD206 (wild type) versus isogenic M2 polarized macrophages lacking the CD206 receptor, illustrating that macrophage activity of Compound 1 is CD206 dependent.
Figure 2B:
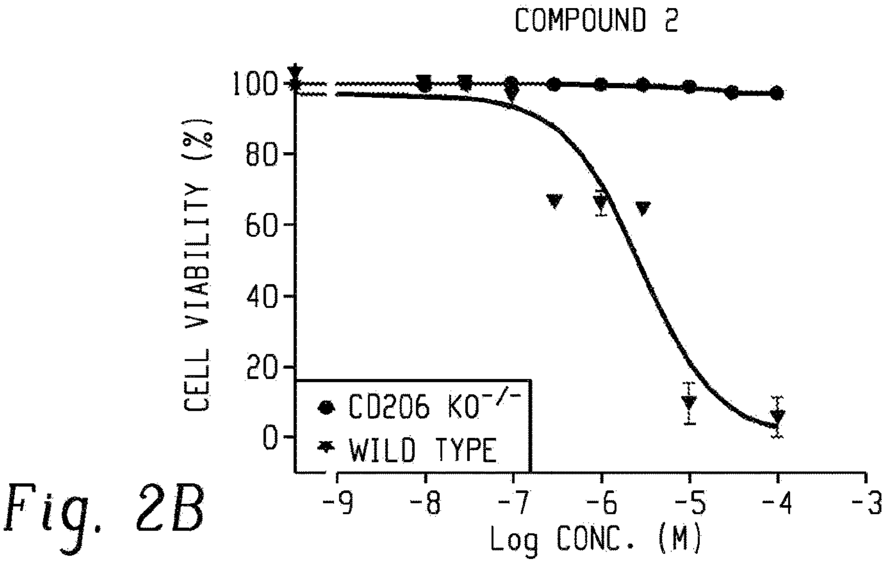
FIG. 2B is a graph of Percentage Relative Cell Viability versus Log Molar Concentration showing cell viabilities in M2 polarized macrophages with intact CD206 (wild type) versus isogenic M2 polarized macrophages lacking the CD206 receptor, illustrating that macrophage activity of Compound 2 is CD206 dependent.
Figure 2C:
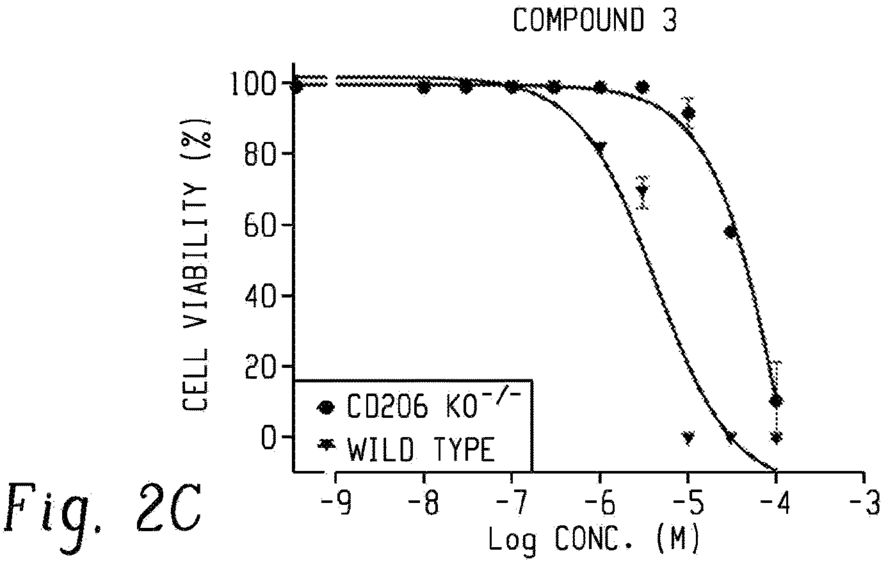
FIG. 2C shows a graph of Percentage Relative Cell Viability versus Log Molar Concentration showing cell viabilities in M2 polarized macrophages with intact CD206 (wild type) versus isogenic M2 polarized macrophages lacking the CD206 receptor, illustrating that macrophage activity of Compound 3 is CD206 dependent.

Similar to the activity of M2 macrophage selective synthetic peptide RP-182, the anti-M2 macrophage activity of Compounds 1-3 is also CD206 dependent. FIGS. 2A-2C show a graph of Percentage Relative Cell Viability versus Log Molar Concentration illustrating macrophage activity of Compounds 1-3 respectively are CD206 dependent.

Example 60. Cell-Based Assays

Cell-based 2HG quantification assays were conducted in 96-well clear plates with a final assay volume of 100 μL.

Figure 13A:
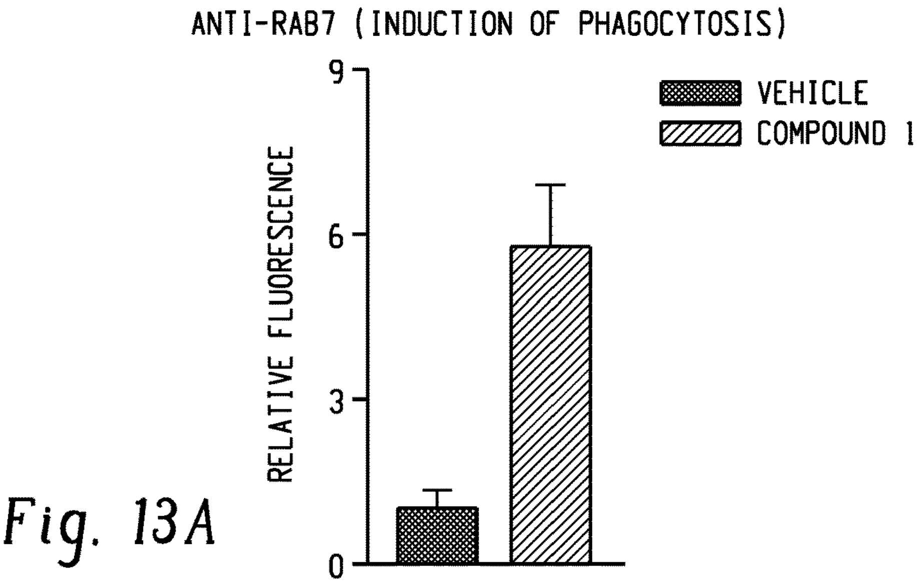
FIG. 13A shows graphs of quantitative relative fluorescence obtained in a second murine in vitro macrophage model, RAW264.7 macrophages polarized into M1 and M2, to indicate induction of phagocytosis in RAW264.7 macrophages treated with Compound 1 compared to RAW264.7 macrophages treated with vehicle only, illustrating that Compound 1 induces phagocytosis in M2 macrophages.
Figure 13B:
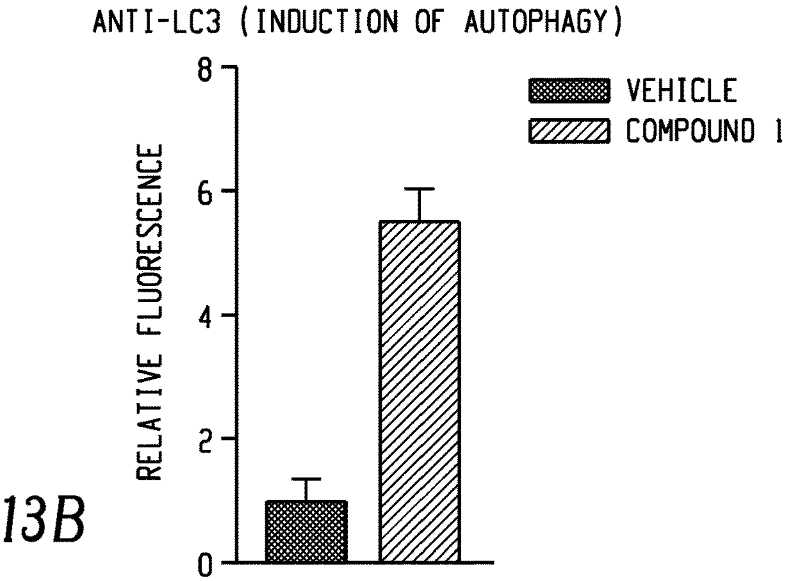
FIG. 13B shows graphs of quantitive relative fluorescence obtained in a second murine in vitro macrophage model, RAW264.7 macrophages polarized into M1 and M2, to indicate induction of autophagy in RAW264.7 macrophages treated with Compound 1 compared to RAW264.7 macrophages treated with vehicle only, illustrating that Compound 1 induces autophagy in M2 macrophages.
Figure 13C:
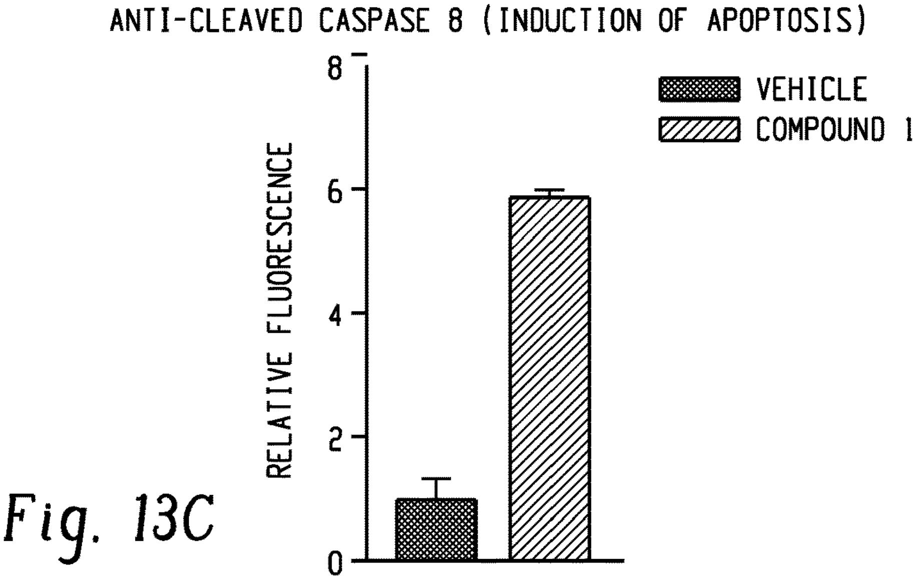
FIG. 13C shows graphs of quantitive relative fluorescence obtained in a second murine in vitro macrophage model, RAW264.7 macrophages polarized into M1 and M2, to indicate induction of apoptosis in RAW264.7 macrophages treated with Compound 1 compared to RAW264.7 macrophages treated with vehicle only, illustrating that Compound 1 induces apoptosis in M2 macrophages.
Figure 14A:
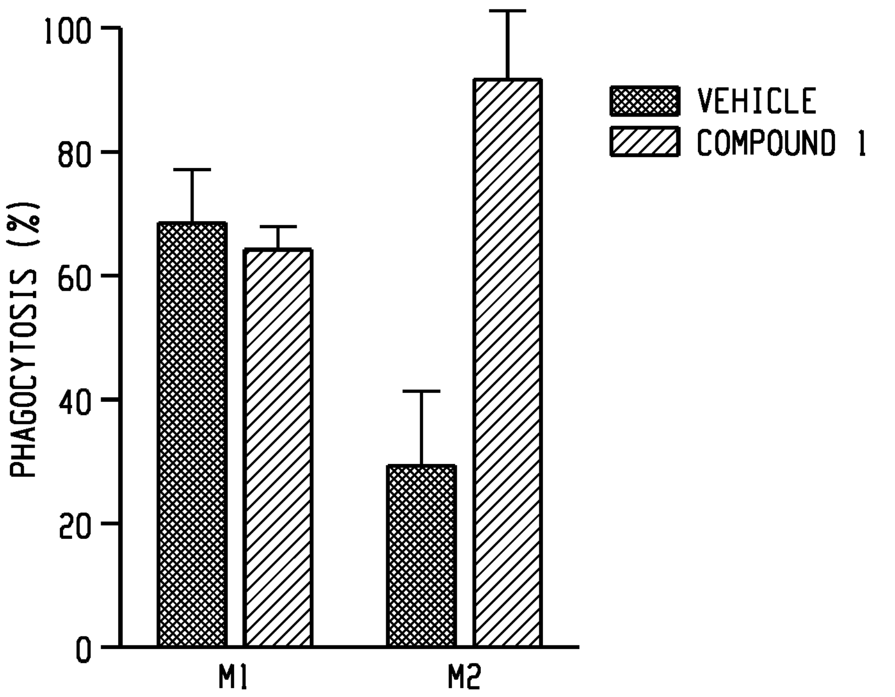
FIG. 14A shows graph of relative quantitative fluorescence to indicate selective induction of cancer cell phagocytosis in M2 macrophages induced by Compound 1 illustrating that Compound 1 increases cancer cell phagocytosis in M2 but not in M1 macrophages.
Figure 14B:
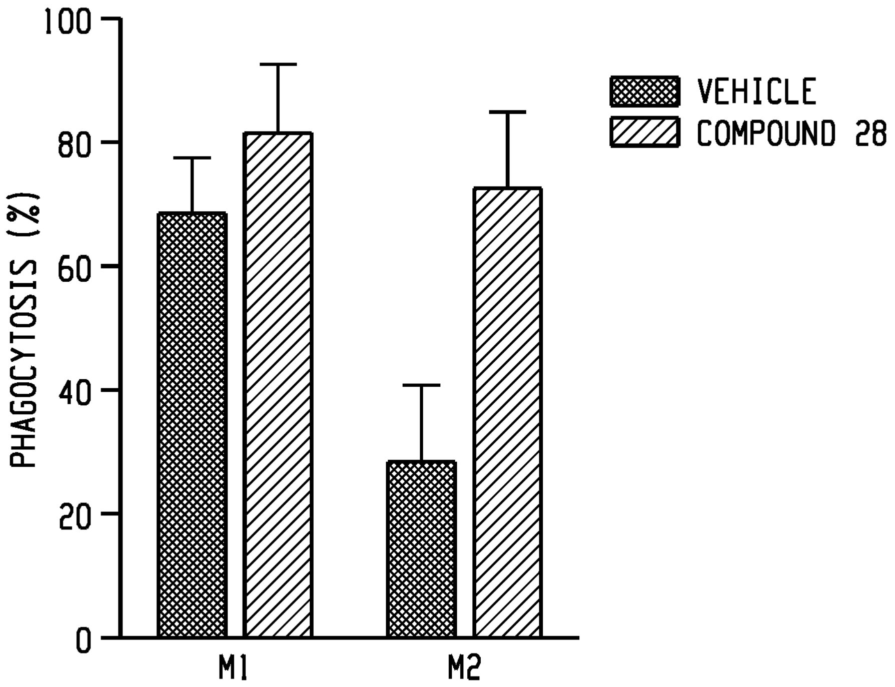
FIG. 14B shows graph of relative quantitative fluorescence to indicate selective induction of cancer cell phagocytosis in M2 macrophages induced by Compound 28 illustrating that Compound 28 increases cancer cell phagocytosis in M2 but not in M1 macrophages.
Figure 16:
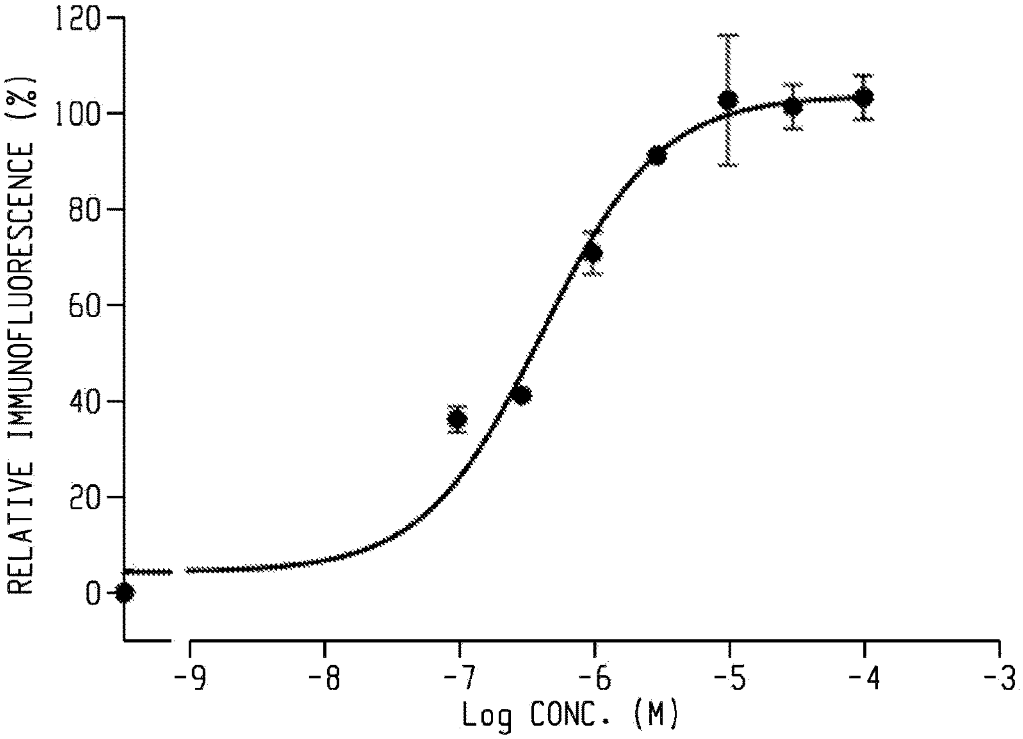
FIG. 16 shows a graph of Percentage Relative Induced Immunofluorescence measuring induced phagocytosis versus Log Molar Concentration in murine M2 macrophages treated with Compound 1 for 24 hours illustrating concentration-dependent induction of phagocytosis by Compound 1.

Induction of phagocytosis, autophagy, and apoptosis was studied in two in vitro models using M1 and M2 macrophages. First in a Bone marrow derived macrophages (BMDM) in vitro model, Compound 1 showed excellent selectivity to induce phagocytosis, autophagy, and apoptosis in M2 but not in M1 macrophages. FIGS. 12A to 12E illustrate this selectivity. In a RAW264.7 cell in vitro model, Compound 1 also showed excellent selectivity to induce phagocytosis, autophagy, and apoptosis in M2 but not in M1 macrophages. FIGS. 13A to 13C illustrate this selectivity Compound 1 selectively increases cancer cell phagocytosis in M2 but not in M1 macrophages. FIGS. 14A to 14B illustrate this selectivity towards M2 macrophages. Also, as showed in FIG. 16, Compound 1 showed full dose response in induction of phagocytosis.

Figure 8:
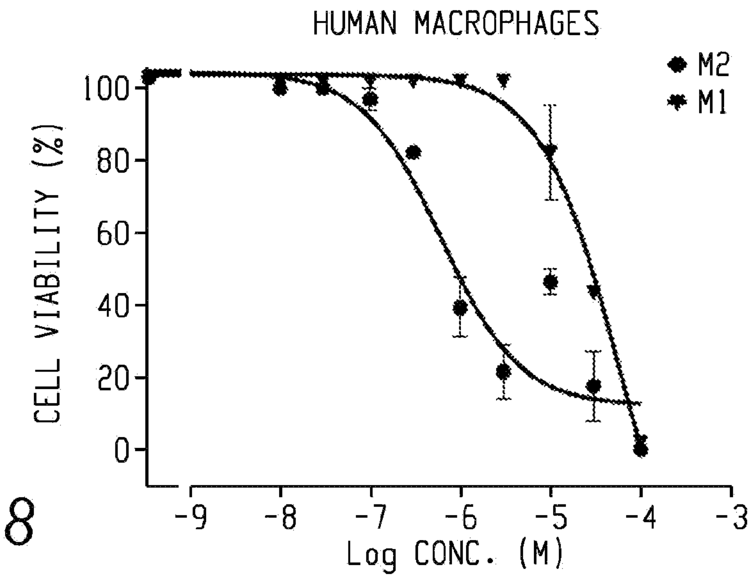
FIG. 8 shows a graph of Percentage Relative Cell Viability versus Log Molar Concentration in a cell viability assay of human macrophages for Compound 1 illustrating that Compound 1 is active in human CD206-$^{high}$ M2 macrophages isolated from healthy volunteers.
Figure 9A:
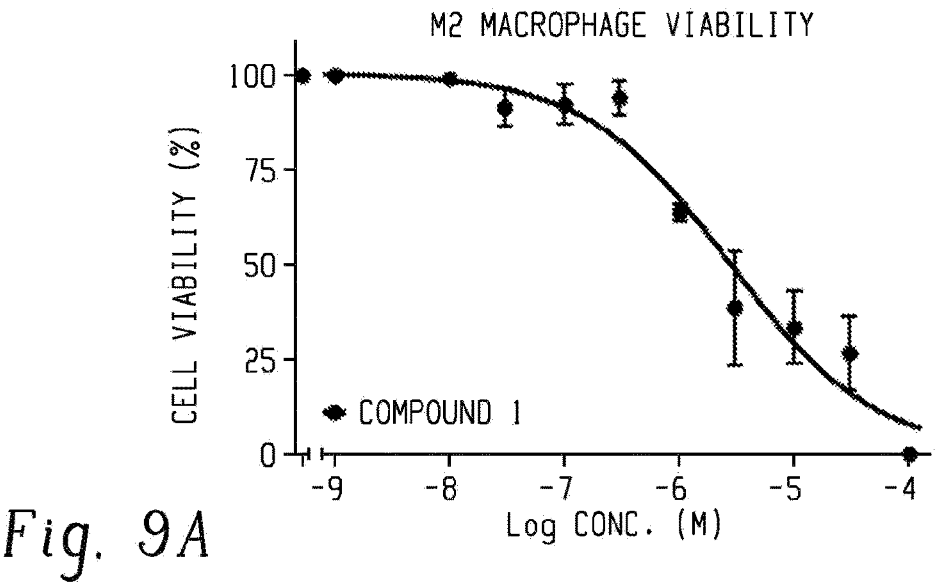
FIG. 9A shows a graph of Percentage Relative Cell Viability versus Log Molar Concentration in a panel of CD206 negative control cell lines illustrating activity of Compound 1 towards CD206$^{high}$ M2 macrophages.
Figure 9B:
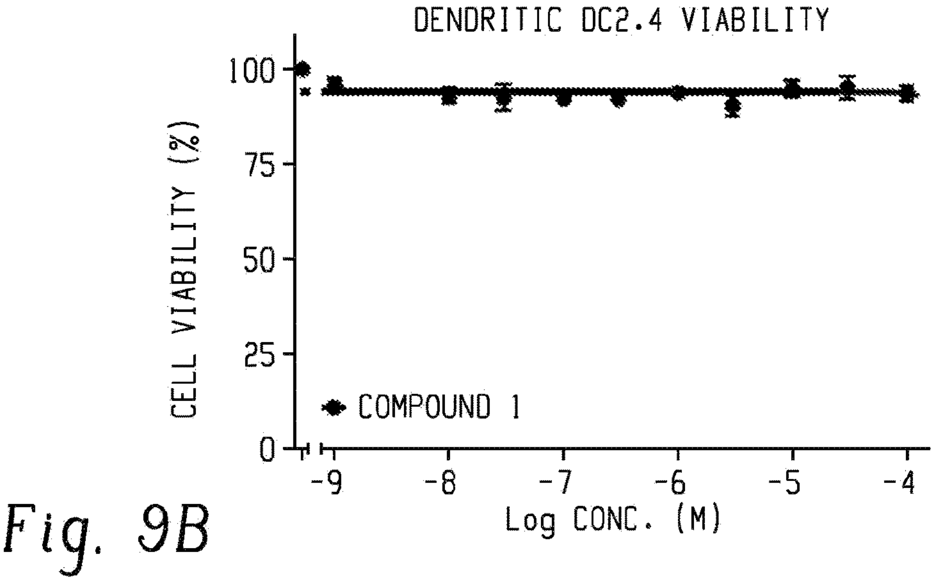
FIG. 9B shows a graph of Percentage Relative Cell Viability versus Log Molar Concentration in a panel of dendritic cell DC2.4 for Compound 1, illustrating selectivity of Compound 1 towards CD206$^{high}$ M2 macrophages.
Figure 9C:
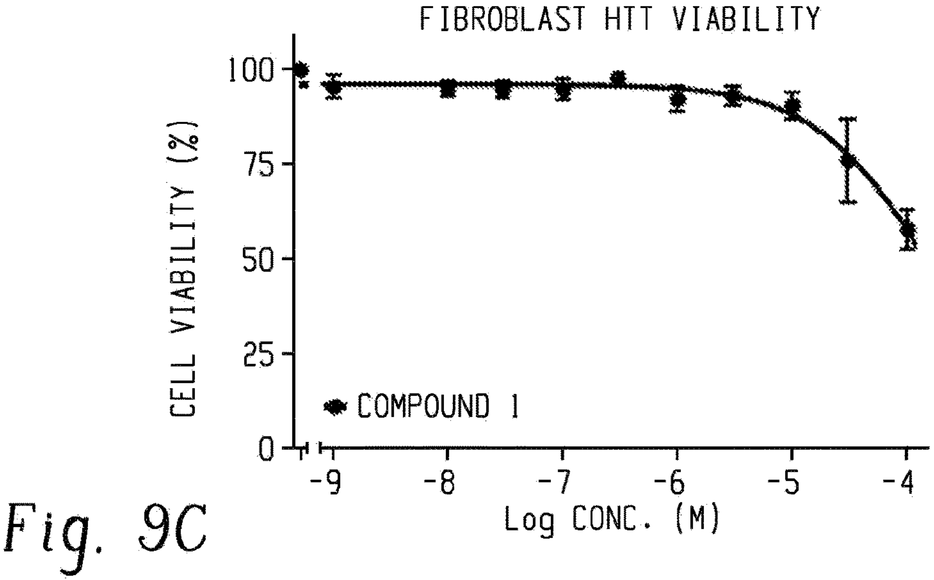
FIG. 9C shows a graph of Percentage Relative Cell Viability versus Log Molar Concentration in a panel of fibroblast HTT for Compound 1, illustrating selectivity of Compound 1 towards CD206$^{high}$ M2 macrophages.
Figure 9D:
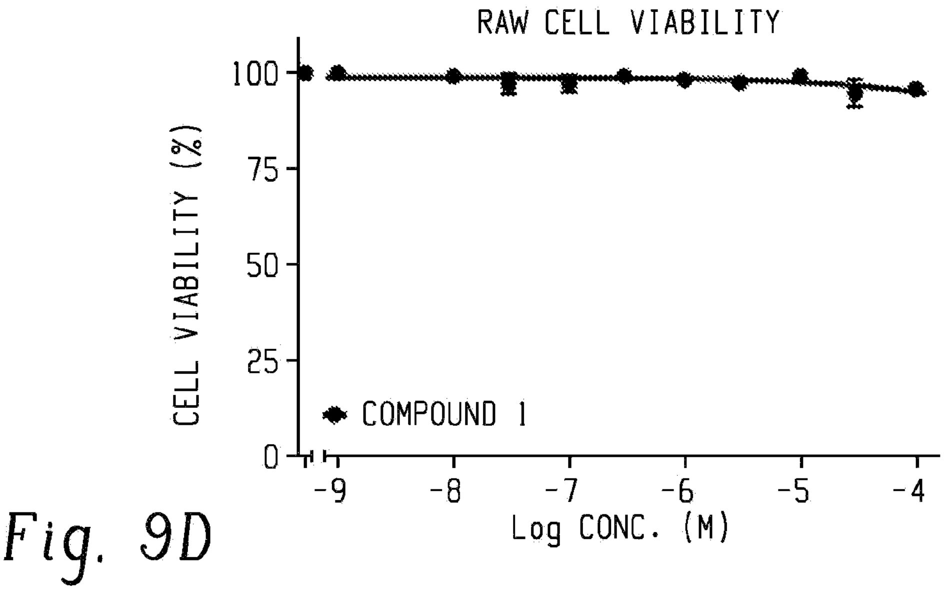
FIG. 9D shows a graph of Percentage Relative Cell Viability versus Log Molar Concentration in a panel of non-polarized RAW264.7 cells for Compound 1, illustrating selectivity of Compound 1 towards CD206$^{high}$ M2 macrophages.
Figure 9E:
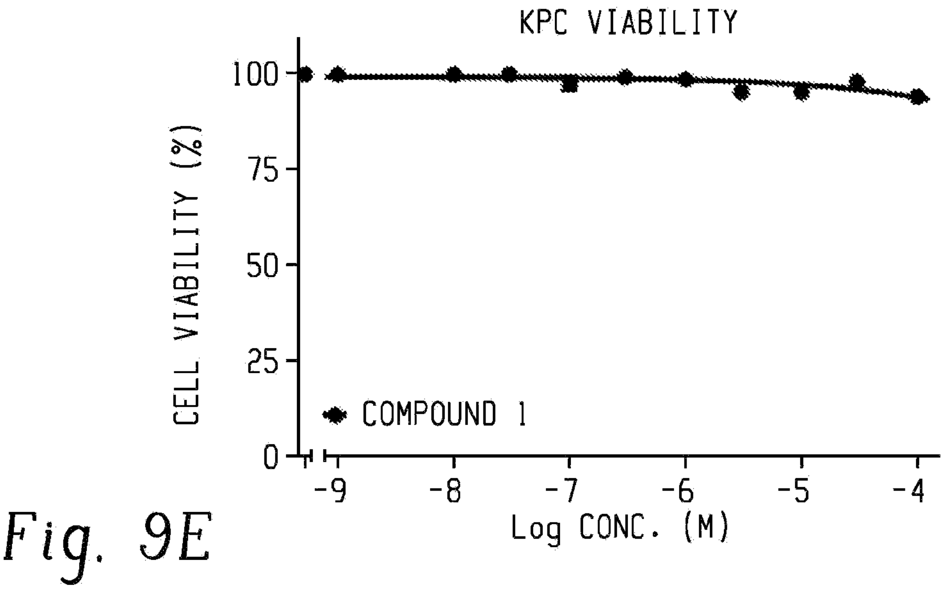
FIG. 9E shows a graph of Percentage Relative Cell Viability versus Log Molar Concentration in a panel of KPC cancer cells (murine pancreatic cancer cells) for Compound 1, illustrating selectivity of Compound 1 towards CD206$^{high}$ M2 macrophages.

As shown in FIG. 8, Compound 1 is active in human $CD206^{high}$ M2 macrophages derived from healthy volunteers compared to M1-like macrophages. Screening with a panel of CD206 negative control cell lines show that the activity of Compound 1 is selective for the $CD206^{high}$ M2 macrophages (FIG. 9A). Similar selectivity is observed in dendritic cell DC2.4 viability (FIG. 9B), fibroblast HTT viability (FIG. 9C), RAW cell viability (FIG. 9D), and KPC viability (FIG. 9E).

FIG. 14A shows a graph of relative quantitative fluorescence to indicate selective induction of cancer cell phagocytosis in M2 macrophages induced by Compound 1, illustrating that Compound 1 increases cancer cell phagocytosis in M2 but not in M1 macrophages.

FIG. 14B shows a graph of relative quantitative fluorescence to indicate selective induction of cancer cell phagocytosis in M2 macrophages induced by Compound 28, illustrating that Compound 28 increases cancer cell phagocytosis in M2 but not in M1 macrophages.

Figure 17:
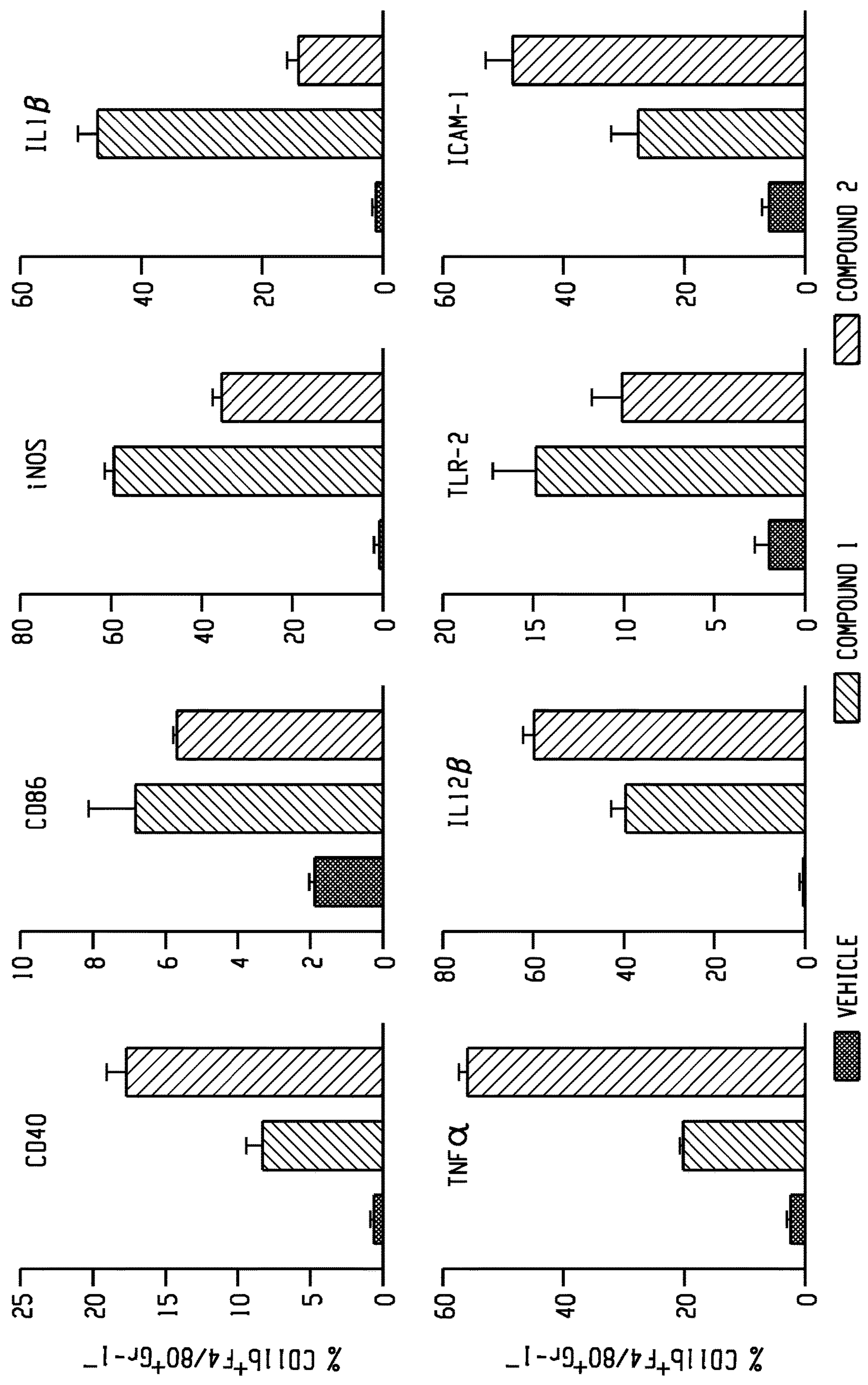
FIG. 17 shows graphs of percent positive cell fractions for M1 markers measured by quantitative flow cytometry of murine M2 macrophages treated with vehicle, 20 μM Compound 1, and 20 μM Compound 2 for 2 hours illustrating induction of M1 markers in M2 macrophages.

FIG. 17 show graphs of percent positive cell fractions for M1 markers measured by quantitative flow cytometry of murine M2 macrophages treated with vehicle, 20 μM Compound 1, and 20 μM Compound 2 for 2 hours, illustrating induction of M1 markers in M2 macrophages

What is claimed is:

1. A method of treating a cancer selected from non-small cell lung cancer, prostate cancer, cholangiocarcinoma, hepatocellular cancer, colon cancer, breast cancer, renal cell cancer, pancreatic cancer, melanoma, sarcoma, and endometrial cancer in a human patient having the cancer and in need of treatment thereof, the method comprising administering to the human patient a therapeutic agent that is a compound of the formula:

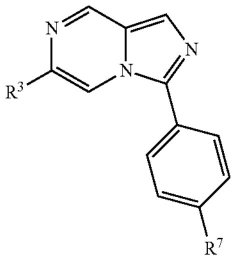

or a pharmaceutically acceptable salt thereof, wherein $R^3$ is phenyl optionally substituted by halo, trifluoromethyl, difluoromethyl, 2-fluoroethyl, or penta-fluoroethyl;

$R^7$ is —C(O)$NR^5R^6$ or —C(O)—$NR^8$—($C_0$-$C_6$alkyl)$NR^5R^6$;

each $R^5$ is independently chosen at each occurrence from hydrogen, $C_1$-$C_6$alkyl, $C_1$-$C_6$hydroxyalkyl, $C_1$-$C_6$alkoxy, an unsubstituted-($C_0$-$C_6$alkyl)cycloalkyl, —($C_0$-$C_6$alkyl)phenyl, —($C_0$-$C_6$alkyl) heteroaryl, —C(O)$C_1$-$C_6$alkyl, and —($C_0$-$C_6$alkyl)cycloalkyl substituted with one or more groups selected from halogen, cyano, hydroxyl, amino, nitro, oxo, azido, $C_2$-$C_6$ alkanoyl, $C_1$-$C_4$ alkoxy, $C_1$-$C_4$ alkyl, $C_1$-$C_4$ alkylthio, and mono- and di-aminoalkyl groups in which alkyl groups have 1-4 carbon atoms; and each $R^6$ is hydrogen or $C_1$-$C_6$alkyl; or $R^5$ and $R^6$ are taken together to form a 4- to 7-membered monocyclic heterocycloalkyl ring, which heterocycloalkyl ring contains 0, 1, or 2 additional heteroatoms chosen from N, O, S, S(O), and $SO_2$ which heterocycloalkyl ring is optionally substituted at any carbon or hetero ring atom with oxo, hydroxy, $C_1$-$C_6$alkyl, $CO_2C_1$-$C_6$alkyl, —C(O) $NR^8R^9$, $NR^8R^9$, or —C(O)$C_1$-$C_6$alkyl; and $R^8$ and $R^9$ are each independently chosen at each occurrence from hydrogen, $C_1$-$C_6$ alkyl, and —C(O)$C_1$-$C_6$alkyl.

2. The method of claim 1, wherein the compound is a compound represented by at least one of Compound 1, and Compound 4 to Compound 29:

Compound 1

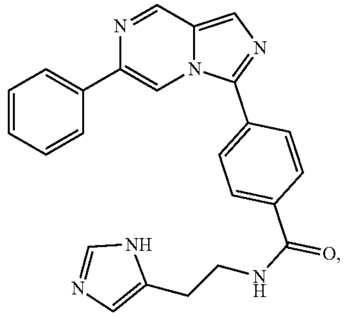

Compound 4

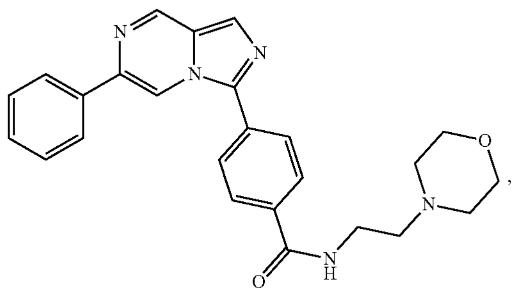

Compound 5

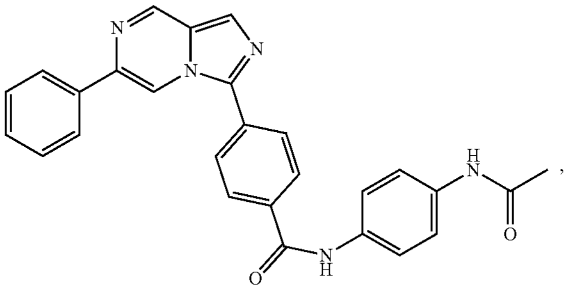

Compound 6

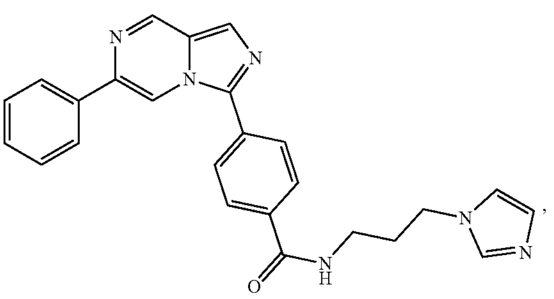

Compound 7
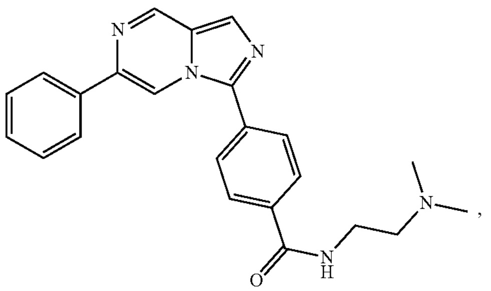
Compound 8
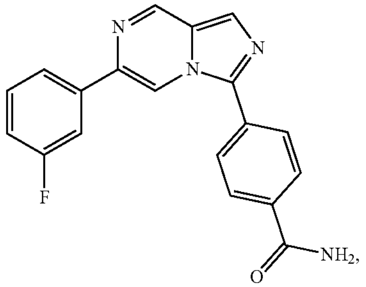
Compound 9
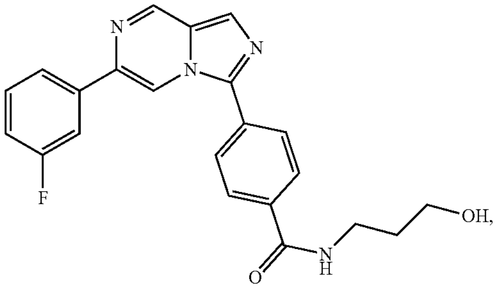
Compound 10
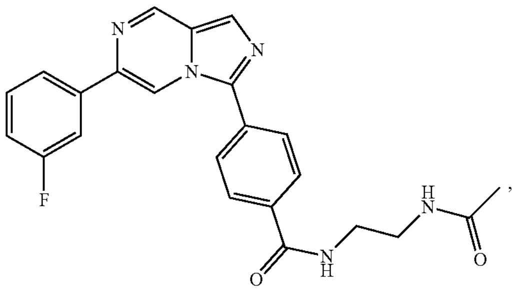
Compound 11
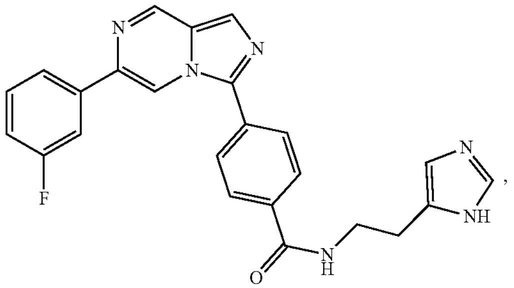
Compound 13
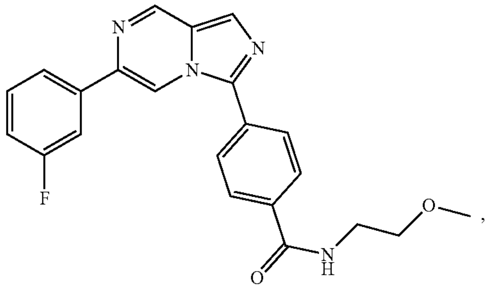
Compound 14
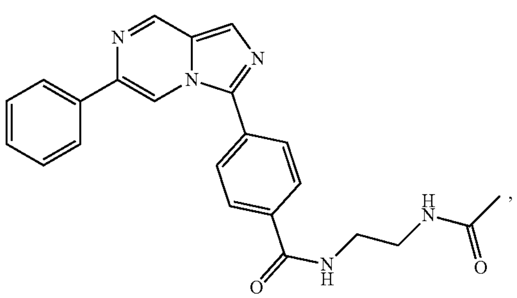
Compound 15
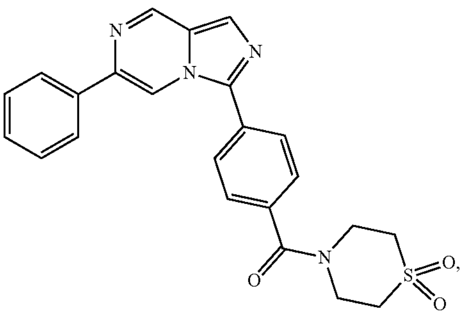
Compound 16
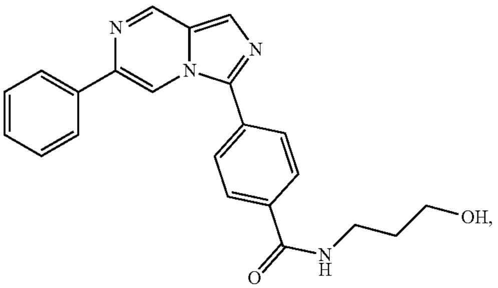
Compound 17
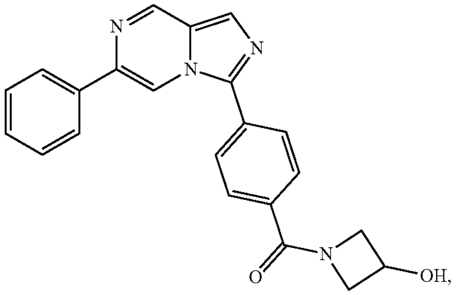

-continued
Compound 18
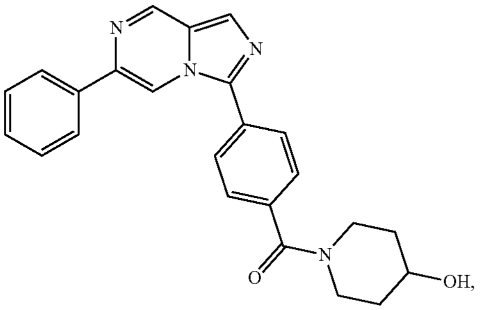
Compound 19
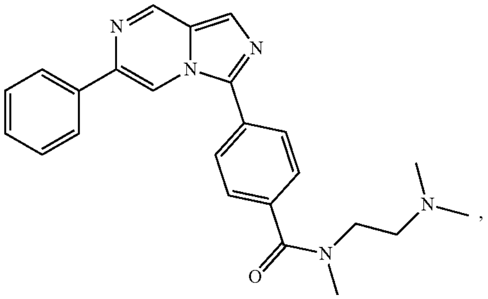
Compound 20
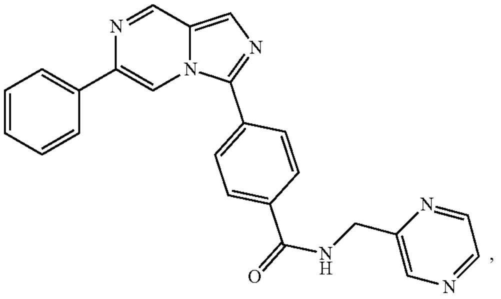
Compound 21
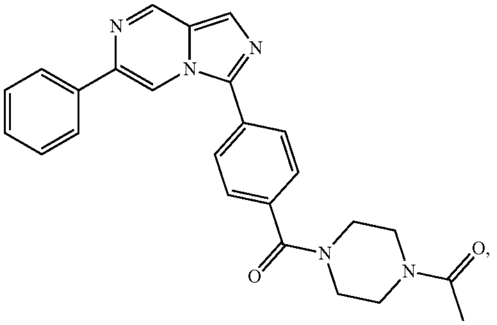
Compound 22
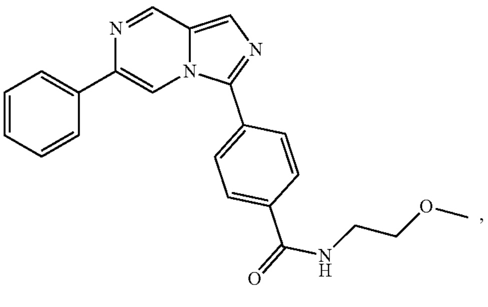
-continued
Compound 23
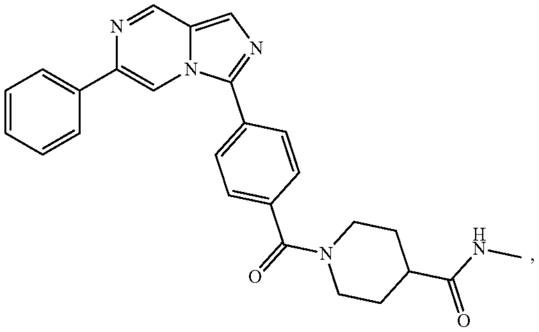
Compound 24
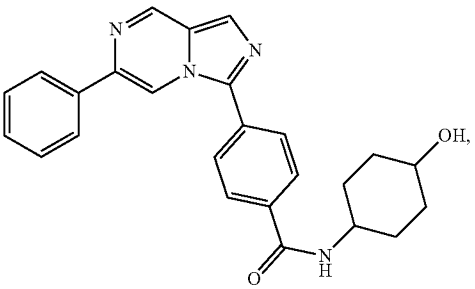
Compound 25
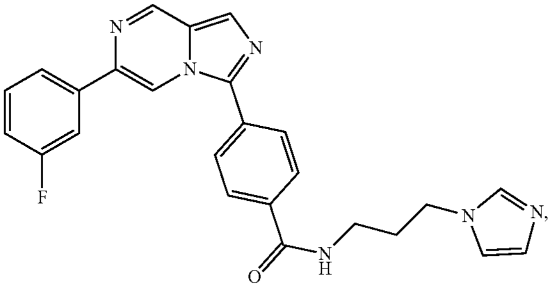
Compound 26
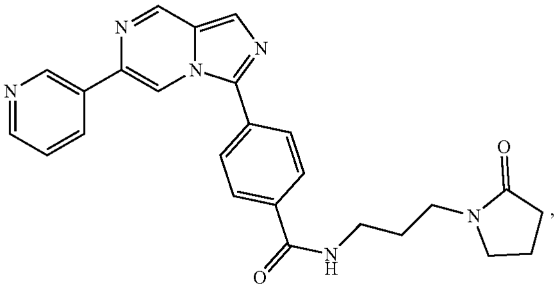
Compound 27
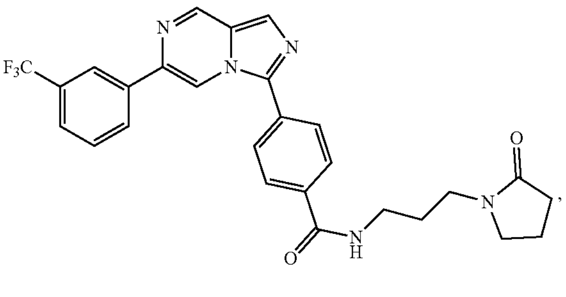

-continued

Compound 28

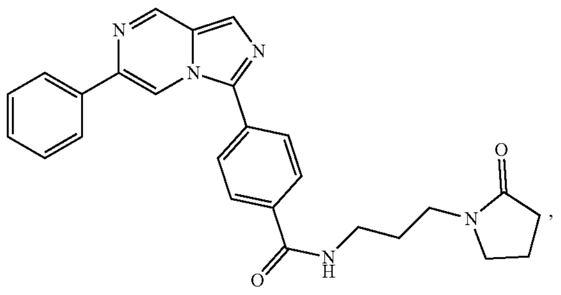

Compound 29

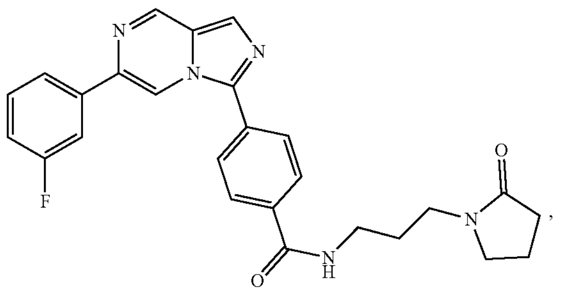

or a pharmaceutically acceptable salt thereof.

3. The method of claim 1, wherein the cancer is associated with CD206-positive tumor-associated macrophages.

4. The method of claim 1, wherein the method further comprises administering to the human patient at least one additional therapeutic agent.

5. The method of claim 1, wherein the compound is compound 1:

Compound 1

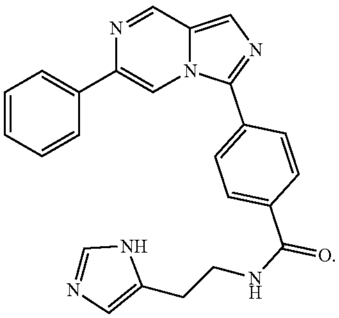

6. The method of claim 1, wherein the compound is any of compounds 1, 4-7, 20-22 and 28:

Compound 1

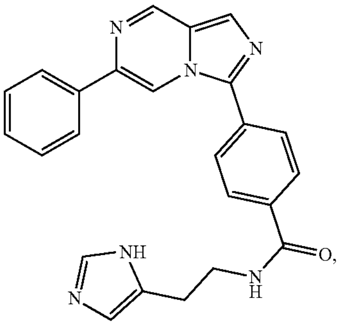

Compound 4

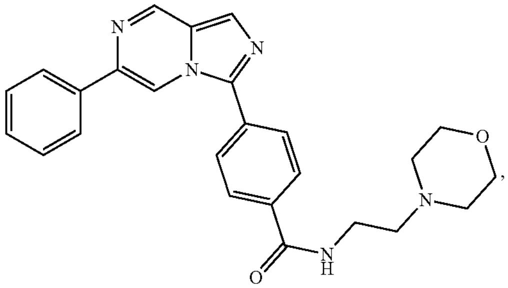

Compound 5

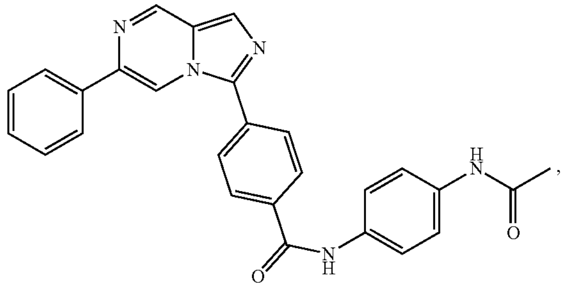

Compound 6

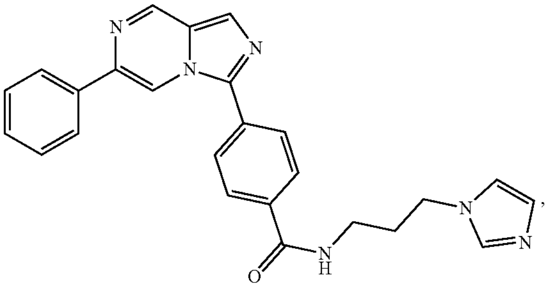

Compound 7

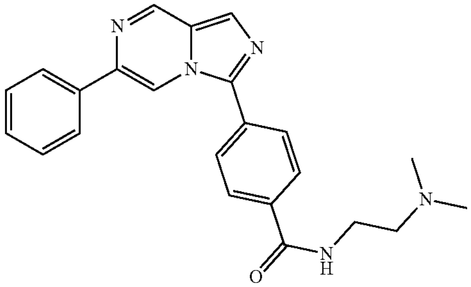

-continued

Compound 20

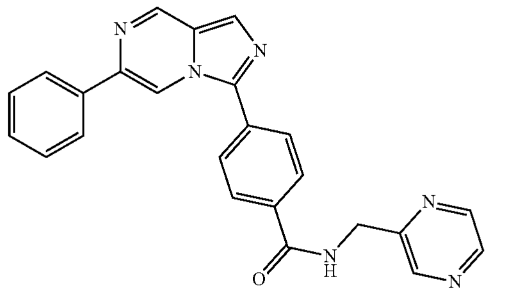

Compound 21

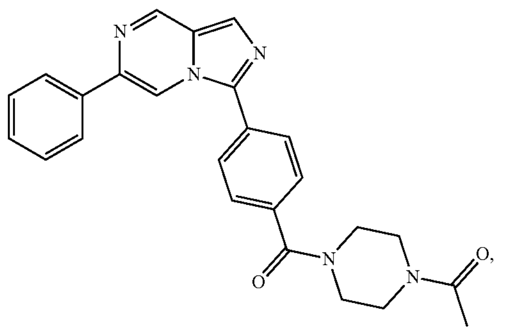

Compound 22

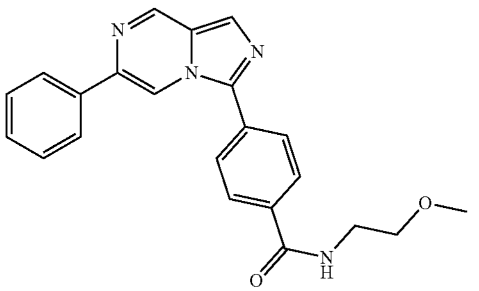

Compound 28

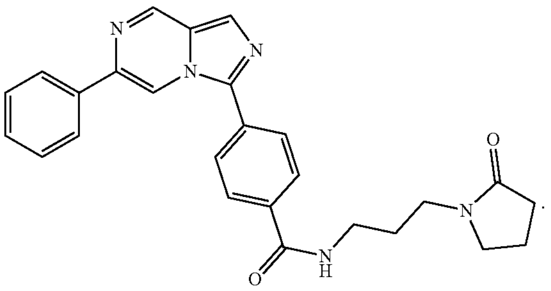

7. The method of claim 1, wherein $R^3$ is phenyl optionally substituted by halo or $C_1$-$C_6$haloalkyl;

$R^7$ is —C(O) $NR^5R^6$;

each $R^5$ is independently chosen at each occurrence from $C_1$-$C_6$hydroxyalkyl, —($C_0$-$C_6$alkyl)cycloalkyl, —($C_0$-$C_6$alkyl)phenyl, —($C_0$-$C_6$alkyl)heteroaryl; and each $R^6$ is hydrogen or $C_1$-$C_6$alkyl; or $R^5$ and $R^6$ are taken together to form a 4- to 7-membered monocyclic heterocycloalkyl ring, which heterocycloalkyl ring contains 0, 1, or 2 additional heteroatoms chosen from N, O, S, S(O), and $SO_2$ which heterocycloalkyl ring is optionally substituted at any carbon or hetero ring atom with oxo, hydroxy, $C_1$-$C_6$alkyl, $CO_2C_1$-$C_6$alkyl, —C(O)$NR^8R^9$, $NR^8R^9$, or —C(O)$C_1$-$C_6$alkyl; and $R^8$ and $R^9$ are each independently chosen at each occurrence from hydrogen, $C_1$-$C_6$ alkyl, and —C(O)$C_1$-$C_6$alkyl.

8. The method of claim 7, wherein the cancer is associated with CD206-positive tumor-associated macrophages.

9. The method of claim 1, wherein $R^3$ is phenyl optionally substituted by halo or $C_1$-$C_6$haloalkyl;

$R^7$ is —C(O)—$NR^8$—($C_1$-$C_3$alkyl) $NR^5R^6$;

each $R^5$ is independently chosen at each occurrence from $C_1$-$C_6$alkyl, $C_1$-$C_6$hydroxyalkyl, —($C_0$-$C_6$alkyl)phenyl, —($C_0$-$C_6$alkyl)heteroaryl, —C(O)$C_1$-$C_6$alkyl; and each $R^6$ is hydrogen or $C_1$-$C_6$alkyl; or $R^5$ and $R^6$ are taken together to form a 4- to 7-membered monocyclic heterocycloalkyl ring, which heterocycloalkyl ring contains 0, 1, or 2 additional heteroatoms chosen from N, O, S, S(O), and $SO_2$ which heterocycloalkyl ring is optionally substituted at any carbon or hetero ring atom with oxo, hydroxy, $C_1$-$C_6$alkyl, $CO_2C_1$-$C_6$alkyl, —C(O)$NR^8R^9$, $NR^8R^9$, or —C(O)$C_1$-$C_6$alkyl; and $R^8$ and $R^9$ are each independently chosen at each occurrence from hydrogen, $C_1$-$C_6$ alkyl, and —C(O)$C_1$-$C_6$alkyl.

10. The method of claim 1, wherein the cancer is pancreatic cancer or melanoma.

11. The method of claim 10, wherein:

$R^3$ is phenyl optionally substituted by halo or $C_1$-$C_6$haloalkyl;

$R^7$ is —C(O)—$NR^8$—($C_1$-$C_3$alkyl)$NR^5R^6$;

each $R^5$ is independently chosen at each occurrence from $C_1$-$C_6$alkyl, $C_1$-$C_6$hydroxyalkyl, —($C_0$-$C_6$alkyl)phenyl, —($C_0$-$C_6$alkyl) heteroaryl, —C(O)$C_1$-$C_6$alkyl; and each $R^6$ is hydrogen or $C_1$-$C_6$alkyl; or $R^5$ and $R^6$ are taken together to form a 4- to 7-membered monocyclic heterocycloalkyl ring, which heterocycloalkyl ring contains 0, 1, or 2 additional heteroatoms chosen from N, O, S, S(O), and $SO_2$ which heterocycloalkyl ring is optionally substituted at any carbon or hetero ring atom with oxo, hydroxy, $C_1$-$C_6$alkyl, $CO_2C_1$-$C_6$alkyl, —C(O)$NR^8R^9$, $NR^8R^9$, or —C(O)$C_1$-$C_6$alkyl; and $R^8$ and $R^9$ are each independently chosen at each occurrence from hydrogen, $C_1$-$C_6$ alkyl, and —C(O)$C_1$-$C_6$alkyl.

12. The method of claim 11, wherein the cancer is associated with CD206-positive tumor-associated macrophages.

13. The method of claim 11, wherein the cancer is pancreatic cancer.

14. The method of claim 1, wherein the cancer is associated with CD206-positive tumor-associated M2 macrophages.

15. A method of treating a cancer selected from pancreatic cancer and melanoma in a human patient having the cancer and in need of treatment thereof, the method comprising administering to the human patient a therapeutic agent that is a compound of the formula:

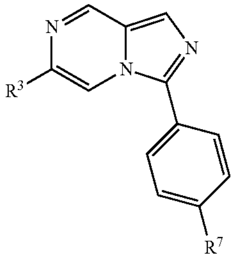

or a pharmaceutically acceptable salt thereof, wherein $R^3$ is phenyl optionally substituted by halo or fluoro $C_1$-$C_6$alkyl;

(a) $R^7$ is —C(O)$NR^5R^6$, in which each $R^5$ is independently chosen at each occurrence from $C_1$-$C_6$hydroxyalkyl, ($C_0$-$C_6$alkyl)cycloalkyl, —($C_0$-$C_6$alkyl)phenyl, —($C_0$-$C_6$alkyl) heteroaryl; and each $R^6$ is hydrogen or $C_1$-$C_6$alkyl; or $R^5$ and $R^6$ are taken together to form a 4- to 7-membered monocyclic heterocycloalkyl ring, which heterocycloalkyl ring contains 0, 1, or 2 additional heteroatoms chosen from N, O, S, S(O), and $SO_2$ which heterocycloalkyl ring is optionally substituted at any carbon or hetero ring atom with oxo, hydroxy, $C_1$-$C_6$alkyl, $CO_2C_1$-$C_6$alkyl, —C(O)$NR^8R^9$, $NR^8R^9$, or —C(O)$C_1$-$C_6$alkyl; and $R^8$ and $R^9$ are each independently chosen at each occurrence from hydrogen, $C_1$-$C_6$ alkyl, and —C(O)$C_1$-$C_6$alkyl; or (b) $R^7$ is —C(O)—$NR^8$—($C_1$-$C_3$alkyl) $NR^5R^6$, in which each $R^5$ is independently chosen at each occurrence from $C_1$-$C_6$alkyl, $C_1$-$C_6$hydroxyalkyl, —($C_0$-$C_6$alkyl)phenyl, —($C_0$-$C_6$alkyl) heteroaryl, —C(O)$C_1$-$C_6$alkyl; and each $R^6$ is hydrogen or $C_1$-$C_6$alkyl; or $R^5$ and $R^6$ are taken together to form a 4- to 7-membered monocyclic heterocycloalkyl ring, which heterocycloalkyl ring contains 0, 1, or 2 additional heteroatoms chosen from N, O, S, S(O), and $SO_2$ which heterocycloalkyl ring is optionally substituted at any carbon or hetero ring atom with oxo, hydroxy, $C_1$-$C_6$alkyl, $CO_2C_1$-$C_6$alkyl, —C(O)$NR^8R^9$, $NR^8R^9$, or —C(O)$C_1$-$C_6$alkyl; and $R^8$ and $R^9$ are each independently chosen at each occurrence from hydrogen, $C_1$-$C_6$ alkyl, and —C(O)$C_1$-$C_6$alkyl.

16. The method of claim 15, wherein the cancer is associated with CD206-positive tumor-associated M2 macrophages.

17. The method of claim 15, wherein the cancer is pancreatic cancer.

* * * * *